(12) United States Patent
McMichael-Phillips et al.

(10) Patent No.: US 6,413,521 B1
(45) Date of Patent: *Jul. 2, 2002

(54) HELMINTH PARASITE ANTIGEN WITH AMINOPEPTIDASE-LIKE ACTIVITY

(75) Inventors: Danielle McMichael-Phillips; Edward Albert Munn, both of Cambridge (GB)

(73) Assignee: The Barbraham Institute, Cambridge (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/637,670

(22) PCT Filed: Nov. 3, 1994

(86) PCT No.: PCT/GB94/02414

§ 371 (c)(1),
(2), (4) Date: Jun. 26, 1996

(87) PCT Pub. No.: WO95/12671

PCT Pub. Date: May 11, 1995

(30) Foreign Application Priority Data

Nov. 3, 1993 (GB) ................................................ 9322702

(51) Int. Cl.[7] ................................................ A61K 39/12
(52) U.S. Cl. ................................................ 424/199.1
(58) Field of Search .......................... 424/265.1, 266.1, 424/94.1, 184.1, 191.1, 94.63, 94.2, 151.1, 185.1, 94.65, 94.67; 530/350, 300, 403, 412; 435/69.1, 183, 212; 536/23.1, 23.2, 23.5

(56) References Cited

U.S. PATENT DOCUMENTS 4,879,213 A * 11/1989 Fox et al.

FOREIGN PATENT DOCUMENTS

| EP | 0434909 A2 | * 9/1990 |
|---|---|---|
| WO | 8602839 | 5/1986 |
| WO | 8800835 | 2/1988 |
| WO | 9323542 | 11/1993 |
| WO | 9418320 | 8/1994 |

OTHER PUBLICATIONS

Munn et al., *Parasitology*, 94(1987), pp. 385–397.

Fire, *The EMBO Journal*, 5, pp. 2673–2680 (1986).

Huang et al., *Proc. Natl. Acad. Sci. USA*, 86, pp. 8640–8644, Nov. 1989.

Aoyagi et al., *The Journal of Antibiotics*, vol. XLIII, No. 2, pp. 143–148 (Feb. 1990).

Lazar et al. Mol. & Cell. Biol. 1988, vol. 8, No. 3, 1247–1252.*

Burges et al. J. Cell. Biol. 1990, vol. 111, 2129–2138.*

Mallet et al. Annales De Recherches Veterinaires 1987 18 (3), 275–8.*

* cited by examiner

Primary Examiner—Jeffrey Stucker
Assistant Examiner—Ulrike Winkler
(74) Attorney, Agent, or Firm—Rothwell, Figg, Ernst & Manbeck

(57) ABSTRACT

A protective helminth parasite antigen which is characterized by processing aminopeptidase-like activity and which, in native form, is an integral membrane protein associated with the gut microvilli of a non-obligate blood feeding helminth parasite, or a functionally-equivalent variant, antigenic fragment or precursor thereof methods for its perparation, vaccine compositions containing it and its use in stimulating an immune response against hellminth parasites in a human or non-human animal.

19 Claims, 33 Drawing Sheets

```
   1 GGTTTAATTA CCCAAGTTTG AGATGACAGC ACAATGGGCT AAAAGGACAG
  51 TGTTACGGTT TACGCCCATC AGCCTTCTCG TCGCTTCATT AGCAATGGCT
 101 CTAGCAATCG CTCTCTCCAT AGGTCTCACT TATCACTTCG TGCGAAATGC
 151 TTATGACACT TCACACAATG AAAGGATCA CCCTGGAGGT GATGACAATT
 201 CTCCTTCTGC AGAAGAACTA CGTCTTCCGA GAAGCGTAAT ACCGTTGCTA
 251 TACGACTTGA GCATCAAAAC GTATCTGCCC AATTACGTGG ATTTCCCGCC
 301 AGAGAAGAAT CTCACCTTTG ATGGGCAAGT GGAAATCTCC ATGGTAGTGA
 351 TGGAACCAAC TAGAAGTATT GTACTAAATG CGAAGAATAT TACTGTGATA
 401 CCAGAGAAAT GCGAGGTGTT TTCGGGCGAT GAAAAACTGG AAATTGAAAG
 451 TGTGATGGAG CATGAGCGGC TTGAGAAGCT GGAATTCCTG TTGAAGAAGC
 501 GGTTAGAAAA AGATCAAAAA GTTCTGCTCA AGGTAATCTA CATCGGCCTT
 551 ATTAGCAACA CCCTTGG7GG ACTGTACCAA GCTACTTATA CACACACGGA
 601 TGGAACCACC AAAATTGCTG CAGCTICTCA AATGGAACCA ACAGATGCCC
 651 GTCGAATGGT GCCATGTCTA GACGAACCCA ACTATAAAGC TAATTGGACA
 701 GTCACTGTGA TTCACCCGAA AGGCACAAGG GCCGTATCGA ATGGTATIGA
 751 AACGAACGGC GAAGGGGATA TCAATGGCGA CTGGATCATA TCGAAGTTCG
 801 AAACCACTCC ACGGATGTCC TCCTATCTAC TGGCAGTTAT TGTCTCGGAA
 851 TTCGACTTCA TCGAAGGCAA CACGACAAGT GGTGTGCGGT TCCGAATATG
 901 GTCACGCCCT GAAGCGAAGA ATATGACACA ATATGCCTTA GACGCCGGCA
 951 TCAGATGTTT AGAGTTTTAC GAGAGCTTCT TCGGCATAAA ATTCCCTTTA
1001 CAAAAGCAAG ATATGGTIGC GCTTCCTGAC TTCTCTGCAG GAGCCATGGA
1051 AAACTGGGGC CT
```

(SEQ ID NO:19)

FIG.19a

```
   1 GGTTTAATTA CCCAAGTTTG AGATGGAGGA GCCGAGGGCA CGGAGGCGGA
  51 CAGTGCTACG GCTCACGCCC ATCACCCTTT CGATCGCTTT GTTAGGCATA
 101 GCAGTTGCCG TTGCGCTCTC TATTGGTCTC ACCTATCTCT TCACACGAAA
 151 TGCCTACGAT ACGTCGCGGA AACCGAAGGA ACCAGATCAC CCCGGAGGCG
 201 GGGATGACAA TCCTCCTICT GCAGAAGAAT TACGTCTCCC ACAAACATA
 251 AAGCCGTTAC TGTACAATTT GACCATCAAA ACGTATCTGC CCGGTTACGT
 301 GGATTTCCCA TCGGAGAAGA ATCTCACCTT CGATGCTCAA GTGCTAATTT
 351 CCATGGTGGT AGTGGAGCCA ACCAAAAGTA TCGTGCTGAA TGCCAAGAAA
 401 ATCACGGCGC TACCGAAAGA ATGCGAGGTG TTCGCAGGCG ATCAAAAACT
 451 GGACATTGAA AGTGTGACGG ATCATGAAAG GCTGGAGAAG CTGGAGTTCA
 501 CTCTGAAGCA ACAACTAGAA AAAGACCAGA AAATCCAGCT CAAGGTTGTC
 551 TATAGCGGCC TCATTAGCGA CACCCTTGGT GGACTGTATC AAGCTACTTA
 601 CAAAGACACG GATGGAACGA CCAAAATCGT CGCAGTCTCT CAAATGGAGC
 651 CAACAGACGC TCGTCGAATG GTGCCGTGTT TTGACGAGCC GAGTTTCAAA
 701 GCCAACTGGA CAGTAACAAT AATTCATCCA AGAGGTACAA CAGCCGCATC
 751 GAATGGCATA GAAACTAACG GTGAAGGAGA ACCCGACGGT GATTGGATCA
 801 CATCAAAATT CAAAACCACT CCACGAATGT CTTCTTATCT GCTGGCCGTT
 851 ATTGTCTCAG AATTCAAATA TATTGAAGGG CGCACGAAAA GCGGTGTGCG
 901 GTTCCGAATA TGGTCACGTC CAGAGGCGGT AAAAATGACG AAATTCGCGT
 951 TAGACGCCGG TGTCAGATGT TTGGAATTCT ATGAAAAGTT TTTCGACATT
1001 CGATTTCCTC TTGAGAAGCA AGATATGGTT GCTCTTCCTG ATTTCTCAGC
1051 AGGAGCCATG GAGAACTGGG GCCT
```

(SEQ ID NO:20)

FIG.19b

```
   1 GGTGCGATGG AGAATTGGGG GCTCATCACT TACAGAGAGA ATTCCTTGTT
  51 GTACGATGAA AGATACTATG CACCGTTGAA CAAGGAACGG GTTGCCATCG
 101 TGGTTGCTCA TGAACTTGCC CATCAGTGGT TCGGTAATCT TGTCACGTTG
 151 AAGTGGTGGG ATGATTTGTG GCTGAACGAA GGTTTCGCAA CATTTGTTGA
 201 ATTCATCGGT GCAGATCATA TCAGCAATGG AACCTTTAGA ATGAAGGACT
 251 ATTTTCGATT GGATGCACTT GTAGACGCCT TGGAGGCTGA TGCGGTAGCT
 301 TCAAGCCATC CGCTATCATT CAAAATCGAT AAAGCTTCAG AAGTTTACGA
 351 AGCTTTCGAC GCTATCACGT ACTCCAAAGG AGCGTCAGTT CTCACAATGT
 401 TGCAAGCGTT GATTGGTGAA GAAAATTTCA ACAAGCCGT AACGCAATAC
 451 CTCAATAAGT TTTCGTTCGA CAACGCGAAA GCGTCCGATC TTTGGGGTGT
 501 CTTCGATGAA GTTGTTAAGG ACGTCAAGGG CCCCGACGGT AATCCTATGA
 551 AAACCACTGA ATTCGCTTAT CAGTGGACGA CTCAGATGGG CTACCCAATA
 601 GTCACAGTGG AAACGTTCAA CGCAACTTCT TTGAAAGTCT CACAAAACCG
 651 ATACAAGACG AATAAGGACG CCCAGGAGCC GGAAAAGTAC CGTCATCCAA
 701 AATATGGGTT CAAGTGGGAT GTTCCTTTAT GGTATCAAGA AGGCGAAAGC
 751 AACGAAATAA AGCAGACCTG GTTGACCAGA GGCGAGCCCC TTTATTTGCA
 801 CGTGAGCAGT TCTGATGATT CCATTGTGGT GAACGCCGAT CGGCATGGAT
 851 TTTACAGGCA AAACTACGAT GCCAACGGTT GGCGAAAGAT TATCAGACAA
 901 CTCAAGGATA ATCATGAGGT CTACAGTCCA AGGACACGGA ACGCGATCAT
 951 AAGTGACGCA TTTGCGGCAG CACTGCTTGA CAATGGGCTC AAGTATGAGA
1001 CTGTTTTCGA ACTATTGGAA TACGCAAAGA ACGAACAGGA ATATCTTCCA
1051 TGGGATGAAA TCATTTCTGG ATTCTATTCA ATTCTTGAAT TCTTTGGCAA
1101 CGAGCCAGAG TCAAAATGGG CTAAAAGCTA TATGATGAAC ATATTGAAGC
1151 CGATGTATGA CAATAGCAGT ATGCAGTACA TCGCTGACAA CTACAAAAAC
1201 GATTCCCTAT TTTTCGAAAA CAATCTCCAA AAAGCGGTCA TTGATGCGTA
1251 CTGTCGCCTT GGATCAAAAG ATTGCATAGG AAAGTATAAG GATCTCTTCA
1301 TTAAAGAAGT CATGGAAAAA TGCGAGGATG ATGAAGAGGC AAGCAAATGC
1351 GTGACGGTTG CCGCTCCTCT GCGATCGAGG GTTTACTGCT ATGGTGTGAA
1401 AGAGGGCGGA GACGATGCTT TCGACAAGGT TATGGGGCTG TACAGTGCAG
1451 AAAATGTTCA GCTGGAGAAG GACATTCTGC TTCGAGCGCT AGGATGTCAC
1501 CGAGATATCA CAGCTCTAAA AGGGTTACTT CTGCGAGCGC TGGATCGGAA
1551 TTCGTCGTTT GTTCGCCTTC AAGATGTGTC TGACGTCTTT ATGGCTGTAT
1601 CTGGAAAGCC CGTGGGCGAG GAATTCATGT CAACTTCCT TCTAGAGAGA
1651 TGGGAAGAAA TAGTCGAAAG CTTACCGTCG GAACACACTT CAGTTGAAAA
1701 AGTGATCAGG GACTGTTCTA CAGGCATTCG ATCCGAGCAA CAAATAGAAC
1751 AGTTGAGAAA TCTTCACAAA AATGGCCGAA ATGCTCGAGA TTACGGTGCA
1801 TTCGACGAGG GAATCGAACG AGCAGAGCAC AAAGTCGACT GGATAAAA
```
(SEQ ID NO:21)

FIG.20a

```
   1 GGAGCGATGG AGAACTGGGG GCTTATCACT TACAGAGAAA CTGCTCTGTT
  51 GTACGATGAA AGACTCTACG CACCGGTTAA TAAGAAAAGA GTTGCTTCAG
 101 TGGTTGCTCA CGAACTTTCT CATCAATGGT TCGGCGATCT TGTTACAATG
 151 GAATGGTGGG ATAATCTGTG GTTGAATGAA GGTTTTGCAT CGTTCATGCA
 201 ATATATTGGC ACAAATGAGA TTACCCGCGA TAACTTTAAG ATGAAGGACT
 251 ATTTCCTGGT GGACTCGTTT GCGCAAGGCA TGGAAGCTGA CGTAGCTTCA
 301 AGCCATCCGC TATCCTTTAA AGTCGACAAG GCTGCAGATG TTGTTGAAGC
 351 TTTTGATGAT GTCACTTATC GTAAAGGAGC ATCGATTCTC ACAATGCTAC
 401 AAGCGTTAAT TGGTGAACAA AACTTCCAAC GGGCCATAAG GCAATACCTC
 451 ATAAAGTTCT CGTACAATAA TGCGAACGCT TCCGATCTCT GGAATGTTTT
 501 TGACGAAGTT GTCAAGGATG TTGCGGGACC TGACGGTAGC CGCATGAAAA
 551 CCTC7rAATT TGCCGATCAG TGGACGACTC AGATGGGCTA CCCAGTAGTT
 601 ACAGTGGAAA CGTTCAATGC AACTACCTTC AAAATATCAC AAAGTCGATA
 651 CAAGAAGAAC AAGAACGCTC AGGAGCCGGA AAAATATCGT CATCCAAAAT
 701 ATGGGTTTGA ATGGGATGTT CCTGTATGGT ACCAGGACAG CAAAAACAGC
 751 GATGTGAAGC GGATCTGGTT AACCAGGGAC AAGCCGACTT ATTTGCATGT
 801 GAACAGTTCC GATGCGTCCA TCGTTGTGAA CGCCGACAGG CATGGATTTT
 851 ACCGGCAAAA CTACGATGAA GATGGCTGGC GAAAGATTAT AAAGATACTC
 901 AAGGATAATC ATAAGTACTA TAGTCCGAGA ACCAGGAACG CTATCATAAG
 951 CGATGCGTTT GCAGCTGCCC TTATTGACAA ACTTGAGTAC GAGACTGTTT
1001 TTGATCTTCT GGAATACGCT AATCAAGAAG AGGAATTTCT ACCGTGGAAC
1051 GAGATTATAA CTGGATTCTA TTCAATTTTG GAGTACTTTG GCAGCGAGCC
1101 GGAATCAAAG TTCGCAAAGA ACTACATGAT GAGCATTCTG AAACCAATGT
1151 ACGACAAGAG CAGCGTTGAT TATATCGCCG AGAACTACAC GAACGATTCG
1201 CTATTTTTCG AAAACAATCT TCAAAAGGCA ATTATCGAGG CCTACTGCTA
1251 TTTTGGATCG AAGGGCTGTA TCCAAAAGTT TAAAGAACTC TTCGACAAAG
1301 AGGTTGTGCA GAAATGCAAG GGCGGTCACA AGGCAAGCAA ATGTGTGGAC
1351 GTTGCTGCTC CTCTTCGAGC GATGGTTTAC TGCTATGGTG TGAACGAAGG
1401 CGGAGATGAT GCATACGACA AGGTGATGGA GTTATATTAC GCAGAAACTG
1451 TTCAGTTGGA GAAGGACTAC CTTCTCGGAG CTTTAGCATG TCACAAAGAC
1501 ATCACAGCCT GAAAGGACT TCTTCTGCTG GCTCTGGATC GTAATTCGTC
1551 Gu11 TTCGC CTTCAAGATA TGGCCAACGT TTCT
```

(SEQ ID NO:22)

FIG.20b

```
   1 GGTGCGATGG AGAACTGGGG GCTCATCACT TACAGAGAAA ATTCCTTGCT
  51 GTACGATGAA AGATACTATG CACCGTTGAG CAAGGAACGG GTTGCCATTG
 101 TGGTTGCTCA TGAACTCGCC CATCAGTGGT TCGGCAACCT TGTCACGTTG
 151 AAGTGGTGGG ATGATTTGTG GCTAAACGAA GGTTTCGCAA CATTTGTTGA
 201 ATTCATCGGT GCAGATCATA TCAGCAACGG AACTTTCAGA ATGAAGGACT
 251 ATTTTCTATT GGATGCTCTT GTAGACGCTT TGGAGGCGGA TTCGGTAGCT
 301 TCAAGCCATC CGCTATCATT TAAAATCGAT AAAGCTTCGG AGGTTTACGA
 351 AGCTTTCGAC GCTATCACGT ACTCAAAAGG AGCGTCAGTT CTCACAATGC
 401 TGCAAGCTTT GATTGGTGAA GAAAACTTCA AGCGGGCTGT GACGCAATAT
 451 CTCAATAAGT TTTCGTTCGA TAACGCGAAA GCTTCCGATC TTTGGGGTGT
 501 CTTCGATGAA GTTGTAAAGG ATGTCAAGGG CCCCGACGGT AATCCTATGA
 551 AAATCACTGA ATTCGCTTAT CAGTGGACGA CTCAGATGGG CTACCCAATA
 601 GTCACAGTGG AAACGTTCAA CGCAACTTCT TTGAAAGTCT CACAAAACCG
 651 ATACAAGACC AATAAGGACG CCCAAGAGCC GGAAAAGTAC CGTCATCCGA
 701 AATATGGGTT CAAGTGGGAT GTTCCTCTAT GGTATCAAGA AGGCGAAAGC
 751 AAGGAAATAA AGCAGACCTG GTTGACTAGA GGAGAGCCCC TTTATTTGCA
 801 CGTGAGCAGT TCGGATGATT CCATTGTGGT GAACGCCCAT CGGCATGGAT
 851 TTTACAGGCA AAACTACGAT GCCAACGGTT GGCGAAAGAT TATCAGGCAA
 901 CTCAAGGAAA ATCATGAGGT CTACAGTCCA AGGACACGGA ACGCGATCAT
 951 AAGTGACGCA TTTGCGGCAG CACTGCTTGA CAATGGGCTC GAGTATGAGA
1001 CTGTTTTCGA ACTATTGGAA TACGCAAAGA ACGAACAGGA ATATCTTCCA
1051 TGGGATGAAA TCATTTCTGG ATTCTATTCA ATTCTTGAAT TCTTTGGCAA
1101 CGAGCCAGAG TCAAAATGGG CCAAAGCGTA TACGATGAGC ATATTGAAGC
1151 CGATGTATGA CAATAGCAGT ATGCAGTACA TCGCTGAAAA CTACAAGAAC
1201 GATTCTCTAT TTTTTGAAAA CAATCTCCAG AAAGCAGTCA TTGATGCGTA
1251 CTGTCGCCTT GGATCAAAAG ATTGCATAGG AAAGTATAAG GATCTCTTCG
1301 TCAAAGAAGT CATGGAAAAA TGCGAAGATG GTGAAGAGGC AAGCAAATGC
1351 GTGACGGTTG CCGCTCCTCT TCGATCGAGA GTTTACTGCT ATGGTGTGAA
1401 AGAGGGCGGA GACGATGCTT TCGACAAGGT TATGGGGCTT TACTCTGCAG
1451 AAAATGTTCA GCTGGAGAAG GACATTCTGC TTCGAGCGCT AGGATGTCAC
1501 CGAGATATCA CAGCTCTAAA AGGATTACTT CTTCGAGCGC TGGATCGGAA
1551 TTCGTCGTTT GTTCGCCTTC AAGATGTGTC TGACGTCTTT ATGGCTGTAT
1601 CAGGAAATCC CGTGGGCGAG GAATTCATGT TCAACTTCCT TCTAGAGAGA
1651 TGGGAAGAAA TAATCGAAAG CTTACCGTCG GAACACACTT CAGTTGAAAA
1701 AGTGATCAAG GACTGTTCTA CAGGCATTCG ATCCGAGCAA CAAATAGAAC
1751 AGTTGAGAAA TCTTCACAAA AATGGCCGAA ATGCTCGAGA TTACGGTGCA
1801 TTTGACGAGG GAATCGAACG AGCAGAGCAC AAAGTCGACT GGTACAAA
                                              (SEQ ID NO:23)
```

FIG.20c

```
  1 MTAQWAKRTV LRFTPISLLV ASLAMALAIA LSIGLTYHFV RNAYDTSHNG
 51 KDHPGGDDNS PSAEELRLPR SVIPLLYDLS IKTYLPNYVD FPPEKNLTFD
101 GQVEISMVVM EPTRSIVLNA KNITVIPEKC EVFSGDEKLE IESVMEHERL
151 EKLEFLLKKR LEKDQKVLLK VIYIGLISNT LGGLYQATYT HTDGTTKIAA
201 ASQMEPTDAR RMVPCLDEPN YKANWTVTVI HPKGTRAVSN GIETNGEGDI
251 NGDWIISKFE TTPRMSSYLL AVIVSEFDFI EGNTTSGVRF RIWSRPEAKN
301 MTQYALDAGI RCLEFYESFF GIKFPLQKQD MVALPDFSAG AMENWG
                                              (SEQ ID NO:24)
```

FIG.21a i

```
  1 MEEPRARRRT VLRLTPITLS IALLGIAVAV ALSIGLTYLF TRNAYDTSRK
 51 PKEPDHPGGG DDNPPSAEEL RLPTNIKPLL YNLTIKTYLP GYVDFPSEKN
101 LTFDAQVLIS MVVVEPTKSI VLNAKKITAL PKECEVFAGD QKLDIESVTD
151 HERLEKL£FT LKQQLEKDQK IQLKVVYSGL ISDTLGGLYQ ATYKDTDGTT
201 KIVAVSQMEP TDARRMVPCF DEPSFKANWT VTIIHPRGTT AASNGIETNG
251 EGEPDGDWIT SKFKTTPRMS SYLLAVIVSE FKYIEGRTKS GVRFRIWSRP
301 EAVKMTKFAL DAGVRCL£FY EKFFDIRFPL EKQDMVALPD FSAGAMENWG
                                              (SEQ ID NO:25)
```

FIG.21a ii

```
  1 GAMENWGLIT YRENSLLYDE RYYAPLNKER VAIVVAHELA HQWFGNLVTL
 51 KWWDDLWLNE GFATFVEFIG ADHISNGTFR MCDYFRLDAL VDALEADAVA
101 SSHPLSFKID KASEVYEAFD AITYSKGASV LTMLQALIGE ENFKQAVTQY
151 LNKFSFDNAK ASDLWGVFDE VVKDVKGPDG NPMKTTEFAY QWTTQMGYPI
201 VTVETFNATS LXVSQNRYKT NKDAQEPEKY RHPKYGFKWD VPLWYQEGES
251 NEIKQTWLTR GEPLYLHVSS SDDSIVUNAD RHGFYRQNYD ANGWRKIIRQ
301 LKDNHEVYSP RTRNAIISDA FAAALLDNGL KYETVFELLE YAKNEQEYLP
351 WDEIISGFYS ILEFFGNEPE SKWAKSYMMN ILKPMYDNSS MQYIADNYKN
401 DSLFFENNLQ KAVIDAYCRL GSKDCIGKYK DLFIKEVMEK C£DDEEASKC
451 VTVAAPLRSR VYCYGVKEGG DDAFDKVMGL YSAENVQLEK DILLRALGCH
501 RDITALKGLL LRALDRNSSF VRLQDVSDVF MAVSGKPVGE EFMFNFLLER
551 WE£IVESLPS EHTSVEKVIR DCSTGIRSEQ QIEQLRNLHK NGRNARDYGA
601 FDEGIER.AEH KVDWIK
```

(SEQ ID NO:26)

FIG.21a iii

```
  1 GAMENWGLIT YRETALLYDE RLYAPVNKKR VASVVAHELS HQWFGDLVTM
 51 EWWDNLWLNE GFASFMQYIG TNEITRDNFK MKDYFLVDSF AQGMEADVAS
101 SHPLSFKVDK AADVVEAFDD VTYRKGASIL TMLQALIGEQ NFQRAIRQYL
151 IKFSYNNANA SDLWNVFDEV VKDVAGPDGS RMKTSEFADQ WTTQMGYPVV
201 TVETFNATTF NISQSRYKKN KNAQEPEKYR HPKYGFEWDV PVWYQDSKNS
251 DVKRIWLTRD KPTYLHVNSS DASIWIJADR HGFYRQNYDE DGWRKIIKIL
301 KDNHKYYSPR TRNAIISDAF AAALIDKLEY ETVFDLLEYA NQEEEFLPWN
351 EIITGFYSIL EYFGSEPESK FAKQYMMSIL KPMYDKSSVD YIAENYTNDS
401 LFFENNLQKA IIEAYCYFGS KGCIQYFKEL FDKEVVQKCK GGHKASKCVD
451 VAAPLRAMVY CYGVNEGGDD AYDKVMELYY AETVQLEKDY LLGALACHKD
501 ITALKGLLLL ALDRNSSFVR LQDMANVS
```

(SEQ ID NO:27)

FIG.21a iv

```
  1 GAMENWGLIT YRENSLLYDE RYYAPLSKER VAIVVAHELA HQWFGNLVTL
 51 KWWDDLWLNE GFATFVEFIG ADHISNGTFR MCDYFLLDAL VDALEADSVA
101 SSHPLSFKID KASEVYEAFD AITYSKGASV LTMLQALIGE ENFKRAVTQY
151 LNKFSFDNAK ASDLWGVFDE VVKDVKGPDG NPMKITEFAY QWTTQMGYPI
201 VTVETFNATS LKVSQNRYKT NKDAQEPEKY RHPKYGFKWD VPLWYQEGES
251 KEIKQTWLTR GEPLYLHVSS SDDSIVVNAH RHGFYRQNYD ANGWRKIIRQ
301 LKENHEVYSP RTRNAIISDA FAAALLDNGL EYETVFELLE YAKNEQEYLP
351 WDEIISGFYS ILEFFGNEPE SKWAKAYTMS ILKPMYDNSS MQYIAENYKN
401 DSLFFENNLQ KAVIDAYCRL GSKDCIGKYK DLFVKEVMEK CEDGEEASKC
451 VTVAAPLRSR VYCYGVKEGG DDAFDKVMGL YSAENVQLEK DILLRALGCH
501 RDITALKGLL LRALDRNSSF VRLQDVSDVF MAVSGNPVGE EFMFNFLLER
551 WEEIIESLPS EHTSVEKVIK DCSTGIRSEQ QIEQLRNLHK NGRNARDYGA
601 FDEGIERAEH KVDWYK
```

(SEQ ID NO:28)

FIG.21a v

```
012 -1    AEELRLPSVIPPLLYDLS  (SEQ ID NO:41)
012 -2    AEELRLPTNIKPLLYNLT  (SEQ ID NO:42)
PepA      AEDLRLPTNIRPLIYDLT  (SEQ ID NO:1)
012 -1    AFELRLPSVIPPLLYDLS  (SEQ ID NO:42)
```

FIG.22

```
o 12-1    ----MTAQWAKRTV LRFTPISLLVASLAMALATALSIGLTYHFVRNAYD----      45
Rat_Amp   MAKGFYISKTLGILGILGVA--AVCTIIALSVVYAQEKNRAENSAIAP              48 o 12-1    ----TSHNGKDHPGGDDNSPSAEELRLPRSVIPLLYDLSIKTYLPNYVD              90
Rat_Amp   TLPGSTSATTSTTNPAIDESKPWNQYRLPKTLIPDSYQVTLRPYLT---              94 o 12-1    FPPEKNL-TFDGQVEISMVVMEPTRSTVLNAKNITVIPEKCE----VFS             134
Rat_Amp   -PNEQGLYIFKGSSTVRFTCNETTNVLIIHSKKLNYTNKGNHRVALRALG            143 o 12-1    GDEKLETESVMEHERLEKLEFLLKKRLEKDQKVLLKVIYIGLISNTLGGL            184
Rat_Amp   DTPAPNIDTTELVERTEYLVVHLQGSLVKGHQYEMDSEFQGELADDLAGF            193 o 12-1    YQATYTHTDGTTKIAAASQMEPTDARRMVPCLDEPNYKANWTVTVIHPKG            234
Rat_Amp   YRSEYME-GGNKKVVATTQMQAADARKSFPCFDEPAMKASFNITLIHPNN            242 o 12-1    TRAVSNGIETNCEG-DINGDWIISKFETTPRMSSYLLAVIVSEFDFIEGN            283
Rat_Amp   LTALSNMLPKDSRTLQEDPSWNVTEFHPTPKMSTYLLAYIVSEFKYVEAV            292 o 12-1    TTSGVRFRIWSRPEA--KNMTQYALDAGIRCLEFYESFFGIKFPLQKQDM            331
Rat_Amp   SPNRVQIRIWARPSAIDEGHGDYALQVTGPILNFFAQHYNTAYPLEKSDQ            342 o 12-1    VALPDFSAGAMENWG----  (SEQ ID NO:24)                           346
Rat_Amp   IALPDFNAGAMENWGLVTYR (SEQ ID NO:35)                           362
```

```
012-1       ---MTAQWAKRTVLRFTPISLLVA-SLAMALAIALSIGLTYHFVRNAYDT    46
Mouse_Apa   MNFAEEEPSKKKYCIKGKHVAIICGVVVAVGLIVGLSVGLIRSCEQDTTPA    50

012-1       ----------SHNGKDHPGGDDNSPSAEELRLPRSVIPLLYDLSIKT       83
Mouse_Apa   PSQPPPEASTALPPQDQNVCPDSEDESGEWKNFRLPDFINPVHYDLEVKA    100

012-1       YLPNYVDFPPEKNLTFDGQVEISMVVMEPTRSIVLNAKNITVIPEKCEVF   133
Mouse_Apa   LM----EEDRYTGIVTISVNLSKPTRDLWLHIRETKITKLPELRR        141

012-1       SGDEKLEIESVMEHERLEKLEFLLKKRLEK--DQKVLLKVIYIGLISNT    180
Mouse_Apa   PSGEQVPILRRCFEYKKQEYVVIQAAEDLAATSGDSVYRLTMEFKGWLNGS   191

012-1       LGGLYQATYTHTDGTTKIAAASQMEPTDARRMVPCLDEPNYKANWTVTVI   230
Mouse_Apa   LVGFYKTTYME-DGQIRSIAATDHEPTDARKSFPCFDEPNKKSTYSISII   240

012-1       HPKGTRAVSNGIETNGEGDINGDWIISKFETTPRMSSYLLAVIVSEFFDF   280
Mouse_Apa   HPKEYSALSNMPEEKSEM-VDDNWKKTTFVKSVPMSTYLVCFAVHREFTAI   289

012-1       EGNTTSGVRFRIWSRPEAKNMTQYALDAGIRCLEFYESFFGIKFPLQKQD   330
Mouse_Apa   ERKSRSGKPLKVYVQPNQKETAEYAANITQAVFDYFEDYFAMEYALPKLD   339

012-1       MVALPDFSAGAMENWG---- (SEQ ID NO:24)                 346
Mouse_Apa   KIAIPDFGTGAMENWGLVTY (SEQ ID NO:37)                 359
```

FIG.21b iii

FIG.21b iv

```
O12-1   MTAQWAKRTVLRFTPISLLVASLAMALAIALSIGLTYHFVRNAYDTSHN-    49
H11-3   MTSQGRTRTLLNLTPIRLIVALFLVAAVGLSIGLTYYFTRKAFDTSEKP     50

O12-1   GKDHPGG--DDNSPSAEELRLPRSVIPLLYDLSIKTYLPNYVDFPPEKNL    97
H11-3   GKDDTGGKDKDNSPSAAELLLPSNIKPLSYDLTIKTYLPGYVDFPPEKNL   100

O12-1   TFDGQVEISMVVMEPTRSIVLNAKNITVIPEKCEVFSGDEKLEIESVMEH   147
H11-3   TFDGRVEISMVVIEPTKSIVLNSKKISVIPQECELVSGDKKLEIESVKEH   150

O12-1   ERLEKLEFLLKKRLEKDQKVLLKVIYIGLISNTLGGLYQATYTHTDGTTK   197
H11-3   PRLEKVEFLIKSQLEKDQQILLKVGYIGLISNSFGGIYQTTYTTPDGTPK   200

O12-1   IAAASQMEPTDARRMVPCLDEPNYKANWTVTVIHPKGTRAVSNGIETNGE   247
H11-3   IAAVSQNEPIDARRMVPCMDEPKYKANWTVTVIHPKGTKAVSNGIEVNGD   250

O12-1   GDINGDWIISKFETTPRMSSYLLAVIVSEFDFIEGNTTSGVRFRIWSRPE   297
H11-3   GEISGDWITSKFLTTPRMSSYLLAVMVSEFEYIEGETIKTGVRFRIWSRPE  300

O12-1   AKNMTQYALDAGIRCLEFYESFFGIKFPLQKQDMVALPDFSAGAMENWG-   346
H11-3   AKKMTQYALQSGIKCIEFYEDFFDIRFPLKKQDMIALPDFSAGAMENWGL  350

(O12-1, SEQ ID NO:24, H11-3, SEQ ID NO:39)
```

FIG. 21b

```
O12-3  ---GAMENWGLITYRENSLLYDERYYAPLNKERVAIVVAHELAHQWFGNLVTLKWWDDLWLNEGFAIFVE         67
H11-3  FSAGAMENWGLITYRENSLLYDDRFYAPMNKQRIARIVAHELAHQWFGDLVTMKWWDNLWLNEGFARFTE         409

O12-3  FIGADHISNGTFRMKDYFRLDALVDALEADAVASSHPLSFKIDKASEVYEAFDAITYSKGASVLTMLQAL        137
H11-3  FIGAGQITQDDARMRNYFLIDVLERALKADSVASSHPLSFRIDKAAEVEEAFDDITYAKGASVLTMLRAL        479

O12-3  IGEENFKQAVTQYLNKFSFDNAKASDLWGVFDEVVKDVKGPDGNPMKTTEFAYQWTTQMGYPIVTVETFN        207
H11-3  IGEEKHKHAVSQYLKKFSYSNAEATDLWAVFDEVVTDVEGPDGKPMKTTEFASQWITQMGFPPVISVAEFN       549

O12-3  ATSLKVSQNRYKTNKDAQEPEKYRHPKYGFKWDVPLWYQEGESNEIKQTWLITRGEPLYLHVSSDDSIVV        277
H11-3  SITLKLTQSRYEANKDAVEKEKYRHPKYGFKWDIPLWYQEGDKKEIKRITWLRRDEPLYLHVSDAGPFVV       619

O12-3  NADRHGFYRQNYDANGWRKIIRQLKDNHEVYSPRTRNAIISDAFAAALLDNGLKYETVFELLEYAKNEQE        347
H11-3  NADRYGFYRQNHDANGWKKIIKQLKDNHEVYSPRTRNVLISDAFAAAATD-AIEYETVFELLNYAEKETE       688

O12-3  YLPWDEIISGFYSILEFFGNEPESKWAKSYMMNILKPMYDNSSMQYIADNYKNDSLFFENNLQKAVIDAY       417
H11-3  YLPLEIAMSGISSILKYFPTIEPEAKPAQTYMMNILKPMYEKSSIDFIANNYRNDKLFFQINLQKDVIDMF      758

O12-3  CRLGSKDCIGKYKDLFIKEVMEKCEDDEEASKCVTVAAPLRSRVYCYGVKEGGDDAFDKVMGLYSAENVQ       487
H11-3  CALGSQDCRKKYKKLFDDEVMNKCRDGQAATECVRIAAPLRSSVVYCYGVKEGGDDYASDKVMELYTAETLA     828

O12-3  LEKDILLRALGCHRDITALKGLLLRALDRNSSFVRLQDVSDVFMAVSGKPVGEEFMFNFLLERWEETIVES      557
H11-3  LEKDFLRLALGCHKDVTALKGLLLRALDRNSSFVRMQDIPSAFNDVAANPIGEEFIFNFLIERWPDIIES      898

O12-3  LPSEHTSVEKVIRDCSTGIRSEQQIEQLRNLHKNGRNARDYGAFDEGIERAEHKVDWIK--  (SEQ ID NO:26)  616
H11-3  IGTKHTYVEKVIPACTSGIRSQQQIDQLKNLQKNGMNARQFGAFDKALERAQNRVDWIKKH  (SEQ ID NO:40)  959
```

FIG.21b vi

SEQUENCE LISTING (1) GENERAL INFORMATION:

(iii) NUMBER OF SEQUENCES: 43

(2) INFORMATION FOR SEQ ID NO:1:

(i) SEQUENCE CHARACTERISTICS:
      (A) LENGTH: 18 amino acids

```
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:1:

Ala Glu Asp Leu Arg Leu Pro Thr Asn Ile Arg Pro Leu Ile Tyr Asp
1               5                   10                  15

Leu Thr (2) INFORMATION FOR SEQ ID NO:2:

(i) SEQUENCE CHARACTERISTICS:
            (A) LENGTH: 8 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:2:

Gly Ala Met Glu Asn Trp Gly Leu
1               5

(2) INFORMATION FOR SEQ ID NO:3:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:3:

GGWGCNATGG ARAAYTGGGG NCT                                        23

(2) INFORMATION FOR SEQ ID NO:4:

(i) SEQUENCE CHARACTERISTICS:
            (A) LENGTH: 23 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:4:

AGNCCCCART TYTCCATNGC WCC                                        23

(2) INFORMATION FOR SEQ ID NO:5:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:5:

GGTTTAATTA CCCAAGTTTG AG                                         22

(2) INFORMATION FOR SEQ ID NO:6:

(i) SEQUENCE CHARACTERISTICS:
            (A) LENGTH: 20 amino acids
```

(B) TYPE: amino acid
        (C) STRANDEDNESS:
        (D) TOPOLOGY: linear (ii) MOLECULE TYPE: peptide (xi) SEQUENCE DESCRIPTION: SEQ ID NO:6:

Glu Pro Leu Ala Pro Gly Ala Ala Asn Pro Lys Gly Val Ala Asn Asp
1               5                   10                  15

Thr Met Gln Phe
            20

(2) INFORMATION FOR SEQ ID NO:7:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:7:

Asp Xaa Glu Glu Glu Xaa Gln Pro Glu Asn Gly Xaa Arg Thr Arg Gly
1               5                   10                  15

Arg Xaa Pro Xaa
            20

(2) INFORMATION FOR SEQ ID NO:8:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:8:

Asp Glu Xaa Cys Ala Val Pro Glu Glu Ala Xaa Gly Val Asp Xaa Pro
1               5                   10                  15

Val Xaa Gly Glu
            20

(2) INFORMATION FOR SEQ ID NO:9:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:9:

Xaa Val Phe Pro Gly Thr Glu Tyr Gly Ala Leu Leu Gln Phe Ala Gln
1               5                   10                  15

Ala Asn Ala Gln Arg Gln Asn Leu Arg
            20                  25

(2) INFORMATION FOR SEQ ID NO:10:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:10:

Asp Val Pro Gly Ala Asp Asp Asn Gly Gln Asp Asn Asp Gly Glu
1               5                  10                  15

Phe Val Gly Glu
            20

(2) INFORMATION FOR SEQ ID NO:11:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:11:

Ala Pro Phe Glu Asp Asp Ala Pro Pro Ala Gly Gly Pro Lys Gly Leu
1               5                  10                  15

Leu Glu Xaa Leu Ser Ala Gly Leu Ala
            20                  25

(2) INFORMATION FOR SEQ ID NO:12:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:12:

Leu Gln Asn Gln Leu Pro Ala Phe
1               5

NFORMATION FOR SEQ ID NO:13:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:13:

Lys Xaa Asp Pro Gly Asp Gly Asn Tyr Gly Gly Xaa Gly Gly Phe
1               5                  10                  15

Gln Gly His Leu
            20

(2) INFORMATION FOR SEQ ID NO:14:

(i) SEQUENCE CHARACTERISTICS:
        (A) LENGTH: 25 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:14:

Ser Ile Pro Asn Gly Asp Thr Gly Pro Xaa Xaa Asn Gly Tyr Xaa Ala

```
                   1               5              10              15
Glu Asn Tyr Asn Gln Gly Gly Xaa Glu
             20              25

(2) INFORMATION FOR SEQ ID NO:15:

(i) SEQUENCE CHARACTERISTICS:
        (A) LENGTH: 21 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:15:

Asp Xaa Glu Pro Gly Pro Arg Glu Pro Gly Gly Ser Glu Gly Glu Arg
1               5                   10                  15
Gln Pro Glu Glu Gly
             20

(2) INFORMATION FOR SEQ ID NO:16:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:16:

Xaa Ala Glu Asp Leu Arg Leu Pro Thr Asn Ile Arg Pro Leu Ile Tyr
1               5                   10                  15
Asp Leu Thr Arg
             20

(2) INFORMATION FOR SEQ ID NO:17:

(i) SEQUENCE CHARACTERISTICS:
        (A) LENGTH: 20 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:17:

Arg Gly Val Val Xaa Pro Val Asp Xaa Xaa Gln Thr Pro Val Pro Gly
1               5                   10                  15
Gln Pro Val Asn
             20

(2) INFORMATION FOR SEQ ID NO:18:

(i) SEQUENCE CHARACTERISTICS:
        (A) LENGTH: 10 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:18:

Xaa Xaa Gln Gly Ser Pro Tyr Asp Xaa Xaa
1               5                   10
```

(2) INFORMATION FOR SEQ ID NO:19:

(i) SEQUENCE CHARACTERISTICS:
        (A) LENGTH: 1062 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

```
GGTTTAATTA CCCAAGTTTG AGATGACAGC ACAATGGGCT AAAAGGACAG TGTTACGGTT      60
TACGCCCATC AGCCTTCTCG TCGCTTCATT AGCAATGGCT CTAGCAATCG CTCTCTCCAT     120
AGGTCTCACT TATCACTTCG TGCGAAATGC TTATGACACT TCACACAATG GAAAGGATCA     180
CCCTGGAGGT GATGACAATT CTCCTTCTGC AGAAGAACTA CGTCTTCCGA GAAGCGTAAT     240
ACCGTTGCTA TACGACTTGA GCATCAAAAC GTATCTGCCC AATTACGTGG ATTTCCCGCC     300
AGAGAAGAAT CTCACCTTTG ATGGGCAAGT GGAAATCTCC ATGGTAGTGA TGGAACCAAC     360
TAGAAGTATT GTACTAAATG CGAAGAATAT TACTGTCATA CCAGAGAAAT GCGAGGTGTT     420
TTCGGGCGAT GAAAAACTGG AAATTGAAAG TGTGATGGAG CATGAGCGGC TTGAGAAGCT     480
GGAATTCCTG TTGAAGAAGC GGTTAGAAAA AGATCAAAAA GTTCTGCTCA AGGTAATCTA     540
CATCGGCCTT ATTAGCAACA CCCTTGGTGG ACTGTACCAA GCTACTTATA CACACACGGA     600
TGGAACCACC AAAATTGCTG CAGCTTCTCA AATGGAACCA ACAGATGCCC GTCGAATGGT     660
GCCATGTCTA GACGAACCCA ACTATAAAGC TAATTGGACA GTCACTGTGA TTCACCCGAA     720
AGGCACAAGG GCCGTATCGA ATGGTATTGA ACGAACGGC GAAGGGGATA TCAATGGCGA      780
CTGGATCATA TCGAAGTTCG AAACCACTCC ACGGATGTCC TCCTATCTAC TGGCAGTTAT     840
TGTCTCGGAA TTCGACTTCA TCGAAGGCAA CACGACAAGT GGTGTGCGGT TCCGAATATG     900
GTCACGCCCT GAAGCGAAGA ATATGACACA ATATGCCTTA GACGCCGGCA TCAGATGTTT     960
AGAGTTTTAC GAGAGCTTCT TCGGCATAAA ATTCCCTTTA CAAAAGCAAG ATATGGTTGC    1020
GCTTCCTGAC TTCTCTGCAG GAGCCATGGA AAACTGGGGC CT                      1062
```

(2) INFORMATION FOR SEQ ID NO:20:

(i) SEQUENCE CHARACTERISTICS:
        (A) LENGTH: 1074 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:20:

```
GGTTTAATTA CCCAAGTTTG AGATGGAGGA GCCGAGGGCA CGGAGGCGGA CAGTGCTACG      60
GCTCACGCCC ATCACCCTTT CGATCGCTTT GTTAGGCATA GCAGTTGCCG TTGCGCTCTC     120
TATTGGTCTC ACCTATCTCT TCACACGAAA TGCCTACGAT ACGTCGCGGA AACCGAAGGA     180
ACCAGATCAC CCCGGAGGCG GGGATGACAA TCCTCCTTCT GCAGAAGAAT TACGTCTCCC     240
CACAAACATA AAGCCGTTAC TGTACAATTT GACCATCAAA ACGTATCTGC CCGGTTACGT     300
GGATTTCCCA TCGAGAAGA ATCTCACCTT CGATGCTCAA GTGCTAATTT CCATGGTGGT      360
AGTGGAGCCA ACCAAAAGTA TCGTGCTGAA TGCCAAGAAA ATCACGGCGC TACCGAAAGA     420
ATGCGAGGTG TTCGCAGGCG ATCAAAAACT GGACATTGAA AGTGTGACGG ATCATGAAAG     480
GCTGGAGAAG CTGGAGTTCA CTCTGAAGCA ACAACTAGAA AAAGACCAGA AAATCCAGCT     540
```

-continued

| | | |
|---|---|---|
| CAAGGTTGTC TATAGCGGCC TCATTAGCGA CACCCTTGGT GGACTGTATC AAGCTACTTA | 600 |
| CAAAGACACG GATGGAACGA CCAAAATCGT CGCAGTCTCT CAAATGGAGC AACAGACGC | 660 |
| TCGTCGAATG GTGCCGTGTT TTGACGAGCC GAGTTTCAAA GCCAACTGGA CAGTAACAAT | 720 |
| AATTCATCCA AGAGGTACAA CAGCCGCATC GAATGGCATA GAAACTAACG GTGAAGGAGA | 780 |
| ACCCGACGGT GATTGGATCA CATCAAAATT CAAAACCACT CCACGAATGT CTTCTTATCT | 840 |
| GCTGGCCGTT ATTGTCTCAG AATTCAAATA TATTGAAGGG CGCACGAAAA GCGGTGTGCG | 900 |
| GTTCCGAATA TGGTCACGTC CAGAGGCGGT AAAAATGACG AAATTCGCGT TAGACGCCGG | 960 |
| TGTCAGATGT TTGGAATTCT ATGAAAAGTT TTTCGACATT CGATTTCCTC TTGAGAAGCA | 1020 |
| AGATATGGTT GCTCTTCCTG ATTTCTCAGC AGGAGCCATG GAGAACTGGG GCCT | 1074 |

(2) INFORMATION FOR SEQ ID NO:21:

(i) SEQUENCE CHARACTERISTICS:
        (A) LENGTH: 1848 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

| | | |
|---|---|---|
| GGTGCGATGG AGAATTGGGG GCTCATCACT TACAGAGAGA ATTCCTTGTT GTACGATGAA | 60 |
| AGATACTATG CACCGTTGAA CAAGGAACGG GTTGCCATCG TGGTTGCTCA TGAACTTGCC | 120 |
| CATCAGTGGT TCGGTAATCT TGTCACGTTG AAGTGGTGGG ATGATTTGTG GCTGAACGAA | 180 |
| GGTTTCGCAA CATTTGTTGA ATTCATCGGT GCAGATCATA TCAGCAATGG AACCTTTAGA | 240 |
| ATGAAGGACT ATTTTCGATT GGATGCACTT GTAGACGCCT GGAGGCTGA TGCGGTAGCT | 300 |
| TCAAGCCATC CGCTATCATT CAAAATCGAT AAAGCTTCAG AAGTTTACGA AGCTTTCGAC | 360 |
| GCTATCACGT ACTCCAAAGG AGCGTCAGTT CTCACAATGT TGCAAGCGTT GATTGGTGAA | 420 |
| GAAAATTTCA AACAAGCCGT AACGCAATAC CTCAATAAGT TTTCGTTCGA CAACGCGAAA | 480 |
| GCGTCCGATC TTTGGGGTGT CTTCGATGAA GTTGTTAAGG ACGTCAAGGG CCCCGACGGT | 540 |
| AATCCTATGA AAACCACTGA ATTCGCTTAT CAGTGGACGA CTCAGATGGG CTACCCAATA | 600 |
| GTCACAGTGG AAACGTTCAA CGCAACTTCT TTGAAATGCT CACAAAACCG ATACAAGACG | 660 |
| AATAAGGACG CCCAGGAGCC GGAAAAGTAC CGTCATCCAA AATATGGGTT CAAGTGGGAT | 720 |
| GTTCCTTTAT GGTATCAAGA AGGCGAAAGC AACGAAATAA AGCAGACCTG GTTGACCAGA | 780 |
| GGCGAGCCCC TTTATTTGCA CGTGAGCAGT TCTGATGATT CCATTGTGGT GAACGCCGAT | 840 |
| CGGCATGGAT TTTACAGGCA AAACTACGAT GCCAACGGTT GGCGAAAGAT TATCAGACAA | 900 |
| CTCAAGGATA ATCATGAGGT CTACAGTCCA AGGACACGGA ACGCGATCAT AAGTGACGCA | 960 |
| TTTGCGGCAG CACTGCTTGA CAATGGGCTC AAGTATGAGA CTGTTTTCGA ACTATTGGAA | 1020 |
| TACGCAAAGA ACGAACAGGA ATATCTTCCA TGGGATGAAA TCATTTCTGG ATTCTATTCA | 1080 |
| ATTCTTGAAT TCTTTGGCAA CGAGCCAGAG TCAAATGGG CTAAAAGCTA TATGATGAAC | 1140 |
| ATATTGAAGC CGATGTATGA CAATAGCAGT ATGCAGTACA TCGCTGACAA CTACAAAAAC | 1200 |
| GATTCCCTAT TTTTCGAAAA CAATCTCCAA AAAGCGGTCA TTGATGCGTA CTGTCGCCTT | 1260 |
| GGATCAAAAG ATTGCATAGG AAAGTATAAG GATCTCTTCA TTAAACAAGT CATGGAAAAA | 1320 |
| TGCGAGGATG ATGAAGAGGC AAGCAAATGC GTGACGGTTG CCGCTCCTCT GCGATCGAGG | 1380 |
| GTTTACTGCT ATGGTGTGAA AGAGGGCGGA GACGATGCTT CGACAAGGT TATGGGGCTG | 1440 |

-continued

```
TACAGTGCAG AAAATGTTCA GCTGGAGAAG GACATTCTGC TTCGAGCGCT AGGATGTCAC    1500

CGAGATATCA CAGCTCTAAA AGGGTTACTT CTGCGAGCGC TGGATCGGAA TTCGTCGTTT    1560

GTTCGCCTTC AAGATGTGTC TGACGTCTTT ATGGCTGTAT CTGGAAAGCC CGTGGGCGAG    1620

GAATTCATGT TCAACTTCCT TCTAGAGAGA TGGGAAGAAA TAGTCGAAAG CTTACCGTCG    1680

GAACACACTT CAGTTCAAAA AGTGATCAGG GACTGTTCTA CAGGCATTCG ATCCGAGCAA    1740

CAAATAGAAC AGTTGAGAAA TCTTCACAAA AATGGCCGAA ATGCTCGAGA TTACGGTGCA    1800

TTCGACGAGG GAATCGAACG AGCAGAGCAC AAAGTCGACT GGATAAAA              1848
```

(2) INFORMATION FOR SEQ ID NO:22:

(i) SEQUENCE CHARACTERISTICS:
        (A) LENGTH: 1584 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:22:

```
GGAGCGATGG AGAACTGGGG GCTTATCACT TACAGAGAAA CTGCTCTGTT GTACGATGAA      60

AGACTCTACG CACCGGTTAA TAAGAAAAGA GTTGCTTCAG TGGTTGCTCA CGAACTTTCT     120

CATCAATGGT TCGGCGATCT TGTTACAATG GAATGGTGGG ATAATCTGTG GTTGAATGAA     180

GGTTTTGCAT CGTTCATGCA ATATATTGGC ACAAATGAGA TTACCCGCGA TAACTTTAAG     240

ATGAAGGACT ATTTCCTGGT GGACTCGTTT GCGCAAGGCA TGGAAGCTGA CGTAGCTTCA     300

AGCCATCCGC TATCCTTTAA AGTCGACAAG GCTGCAGATG TTGTTGAAGC TTTTGATGAT     360

GTCACTTATC GTAAAGGAGC ATCGATTCTC ACAATGCTAC AAGCGTTAAT TGGTGACAAA     420

ACTTCCAACG GGGCCATAAG GCAATACCTC ATAAAGTTCT CGTACAATAA TGCGAACGCT     480

TCCGATCTCT GGAATGTTTT TGACGAAGTT GTCAAGGATG TTGCGGGACC TGACGGTAGC     540

CGCATGAAAA CCTCTGAATT TGCCGATCAG TGGACGACTC AGATGGGCTA CCCAGTAGTT     600

ACAGTGGAAA CGTTCAATGC AACTACCTTC AAAATATCAC AAAGTCGATA CAAGAAGAAC     660

AAGAACGCTC AGGAGCCGGA AAAATATCGT CATCCAAAAT ATGGGTTTGA ATGGGATGTT     720

CCTGTATGGT ACCAGGACAG CAAAAACAGC GATGTGAAGC GGATCTGGTT AACCAGGGAC     780

AAGCCGACTT ATTTGCATGT GAACAGTTCC GATGCGTCCA TCGTTGTGAA CGCCGACAGG     840

CATGGATTTT ACCGGCAAAA CTACGATGAA GATGGCTGGC GAAAGATTAT AAAGATACTC     900

AAGGATAATC ATAAGTACTA TAGTCCGAGA ACCAGGAACG CTATCATAAG CGATGCGTTT     960

GCAGCTGCCC TTATTGACAA ACTTGAGTAC GAGACTGTTT TTGATCTTCT GGAATACGCT    1020

AATCAAGAAG AGGAATTTCT ACCGTGGAAC GAGATTATAA CTGGATTCTA GGCAATTTTG    1080

GAGTACTTTG GCAGCGAGCC GGAATCAAAG TTCGCAAAGA ACTACATGAT GAGCATTCTG    1140

AAACCAATGT ACGACAAGAG CAGCGTTGAT TATATCGCCG AGAACTACAC GAACGATTCG    1200

CTATTTTTCG AAAACAATCT TCAAAAGGCA ATTATCGAGG CCTACTGCTA TTTTGGATCG    1260

AAGGGCTGTA TCCAAAAGTT TAAAGAACTC TTCGACAAAG AGGTTGTGCA GAAATGCAAG    1320

GGCGGTCACA AGGCAAGCAA ATGTGTGGAC GTTGCTGCTC CTCTTCGAGC GATGGTTTAC    1380

TGCTATGGTG TGAACGAAGG CGGAGATGAT GCATACGACA AGGTGATGGA GTTATATTAC    1440

GCAGAAACTG TTCAGTTGGA GAAGGACTAC CTTCTCGGAG CTTTAGCATG TCACAAAGAC    1500

ATCAACAGCC TTGAAAGGAC TCTTCTGCTG GCTCTGGATC GTAATTCGTC GTTTGTTCGC    1560
```

CTTCAAGATA TGGCCAACGT TTCT          1584

(2) INFORMATION FOR SEQ ID NO:23:

(i) SEQUENCE CHARACTERISTICS:
        (A) LENGTH: 1848 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:23:

```
GGTGCGATGG AGAACTGGGG GCTCATCACT TACAGAGAAA ATTCCTTGCT GTACGATGAA    60

AGATACTATG CACCGTTGAG CAAGGAACGG GTTGCCATTG TGGTTGCTCA TGAACTCGCC   120

CATCAGTGGT TCGGCAACCT TGTCACGTTG AAGTGGTGGG ATGATTTGTG GCTAAACGAA   180

GGTTTCGCAA CATTTGTTGA ATTCATCGGT GCAGATCATA TCAGCAACGG AACTTTCAGA   240

ATGAAGGACT ATTTTCTATT GGATGCTCTT GTAGACGCTT TGGAGGCGGA TTCGGTAGCT   300

TCAAGCCATC CGCTATCATT TAAAATCGAT AAAGCTTCGG AGGTTTACGA AGCTTTCGAC   360

GCTATCACGT ACTCAAAAGG AGCGTCAGTT CTCACAATGC TGCAAGCTTT CATTGGTGAA   420

GAAAACTTCA GCGGGCTGT GACGCAATAT CTCAATAAGT TTTCGTTCGA TAACGCGAAA   480

GCTTCCGATC TTTGGGGTGT CTTCGATGAA GTTGTAAAGG ATGTCAAGGG CCCCGACGGT   540

AATCCTATGA AAATCACTGA ATTCGCTTAT CAGTGGACGA CTCAGATGGG CTACCCAATA   600

GTCACAGTGG AAACGTTCAA CGCAACTTCT TTGAAACTCT CACAAAACCG ATACAAGACC   660

AATAAGGACG CCCAAGAGCC GGAAAAGTAC CGTCATCCGA AATATGGGTT CAAGTGGGAT   720

GTTCCTCTAT GGTATCAAGA AGGCGAAAGC AAGGAAATAA AGCAGACCTG GTTGACTAGA   780

GGAGAGCCCC TTTATTTGCA CGTGAGCAGT TCGGATGATT CCATTGTGGT GAACGCCCAT   840

CGGCATGGAT TTTACAGGCA AAACTACGAT GCCAACGGTT GGCGAAAGAT TATCAGGCAA   900

CTCAAGGAAA ATCATGAGGT CTAGAGTCCA AGGACACGGA ACGCGATCAT AAGTGACGCA   960

TTTGCGGCAG CACTGCTTGA CAATGGGCTC GAGTATGAGA CTGTTTTCGA ACTATTGGAA  1020

TACGCAAAGA ACGAACAGGA ATATCTTCCA TGGGATGAAA TCATTTCTGG ATTCTATTCA  1080

ATTCTTGAAT TCTTTGGCAA CGAGCCAGAG TCAAAATGGG CCAAAGCGTA TACGATGAGC  1140

ATATTGAAGC CGATGTATGA CAATAGCAGT ATGCAGTACA TCGCTGAAAA CTACAAGAAC  1200

GATTCTCTAT TTTTTGAAAA CAATCTCCAG AAAGCAGTCA TTGATGCGTA CTGTCGCCTT  1260

GGATCAAAAG ATTGCATAGG AAAGTATAAG GATCTCTTCG TCAAAGAAGT CATGGAAAAA  1320

TGCGAAGATG GTGAAGAGGC AAGCAAATGC GTGACGGTTG CCGCTCCTCT TCGATCGAGA  1380

GTTTACTGCT ATGGTGTGAA AGAGGGCGGA GACGATGCTT TCGACAAGGT TATGGGGCTT  1440

TACTCTGCAG AAAATCTTCA GCTGGAGAAG GACATTCTGC TTCGAGCGCT AGGATGTCAC  1500

CGAGATATCA CAGCTCTAAA AGGATTACTT CTTCGAGCGC TGGATCGGAA TTCGTCGTTT  1560

GTTCGCCTTC AAGATGTGTC TGACGTCTTT ATGGCTGTAT CAGGAAATCC CGTGGGCGAG  1620

GAATTCATGT TCAACTTCCT TCTAGAGAGA TGGGAAGAAA TAATCGAAAG CTTACCGTCG  1680

GAACACACTT CAGTTGAAAA AGTGATCAAG GACTGTTCTA CAGGCATTCG ATCCGAGCAA  1740

CAAATAGAAC AGTTGAGAAA TCTTCACAAA AATGGCCGAA ATGCTCGAGA TTACGGTGCA  1800

TTTGACGAGG GAATCGAACG AGCAGAGCAC AAAGTCGACT GGTACAAA           1848
```

(2) INFORMATION FOR SEQ ID NO:24:

(i) SEQUENCE CHARACTERISTICS:
        (A) LENGTH: 346 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

```
Met Thr Ala Gln Trp Ala Lys Arg Thr Val Leu Arg Phe Thr Pro Ile
  1               5                  10                  15

Ser Leu Leu Val Ala Ser Leu Ala Met Ala Leu Ala Ile Ala Leu Ser
             20                  25                  30

Ile Gly Leu Thr Tyr His Phe Val Arg Asn Ala Tyr Asp Thr Ser His
         35                  40                  45

Asn Gly Lys Asp His Pro Gly Gly Asp Asn Ser Pro Ser Ala Glu
     50                  55                  60

Glu Leu Arg Leu Pro Arg Ser Val Ile Pro Leu Leu Tyr Asp Leu Ser
 65                  70                  75                  80

Ile Lys Thr Tyr Leu Pro Asn Tyr Val Asp Phe Pro Pro Glu Lys Asn
                 85                  90                  95

Leu Thr Phe Asp Gly Gln Val Glu Ile Ser Met Val Val Met Glu Pro
                100                 105                 110

Thr Arg Ser Ile Val Leu Asn Ala Lys Asn Ile Thr Val Ile Pro Glu
            115                 120                 125

Lys Cys Glu Val Phe Ser Gly Asp Lys Leu Glu Ile Glu Ser Val
        130                 135                 140

Met Glu His Glu Arg Leu Glu Lys Leu Glu Phe Leu Leu Lys Lys Arg
145                 150                 155                 160

Leu Glu Lys Asp Gln Lys Val Leu Leu Lys Val Ile Tyr Ile Gly Leu
                165                 170                 175

Ile Ser Asn Thr Leu Gly Gly Leu Tyr Gln Ala Thr Tyr Thr His Thr
            180                 185                 190

Asp Gly Thr Thr Lys Ile Ala Ala Ser Gln Met Glu Pro Thr Asp
        195                 200                 205

Ala Arg Arg Met Val Pro Cys Leu Asp Glu Pro Asn Tyr Lys Ala Asn
210                 215                 220

Trp Thr Val Thr Val Ile His Pro Lys Gly Thr Arg Ala Val Ser Asn
225                 230                 235                 240

Gly Ile Glu Thr Asn Gly Glu Gly Asp Ile Asn Gly Glu Trp Ile Ile
                245                 250                 255 er Lys Phe Glu Thr Thr Pro Arg Met Ser Ser Tyr Leu Leu Ala Val
            260                 265                 270

Ile Val Ser Glu Phe Asp Phe Ile Glu Gly Asn Thr Thr Ser Gly Val
            275                 280                 285

Arg Phe Arg Ile Trp Ser Arg Pro Glu Ala Lys Asn Met Thr Gln Tyr
            290                 295                 300

Ala Leu Asp Ala Gly Ile Arg Cys Leu Glu Phe Tyr Glu Ser Phe Phe
305                 310                 315                 320

Gly Ile Lys Phe Pro Leu Gln Lys Gln Asp Met Val Ala Leu Pro Asp
                325                 330                 335

Phe Ser Ala Gly Ala Met Glu Asn Trp Gly
                340                 345
```

(2) INFORMATION FOR SEQ ID NO:25:

(i) SEQUENCE CHARACTERISTICS:
        (A) LENGTH: 350 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

```
Met Glu Glu Pro Arg Ala Arg Arg Thr Val Leu Arg Leu Thr Pro
 1               5                  10                  15

Ile Thr Leu Ser Ile Ala Leu Leu Gly Ile Ala Val Ala Val Ala Leu
                20                  25                  30

Ser Ile Gly Leu Thr Tyr Leu Phe Thr Arg Asn Ala Tyr Asp Thr Ser
                35                  40                  45

Arg Lys Pro Lys Glu Pro Asp His Pro Gly Gly Asp Asp Asn Pro
 50                  55                  60

Pro Ser Ala Glu Glu Leu Arg Leu Pro Thr Asn Ile Lys Pro Leu Leu
 65                  70                  75                  80

Tyr Asn Leu Thr Ile Lys Thr Tyr Leu Pro Gly Tyr Val Asp Phe Gln
                85                  90                  95

Ser Glu Lys Asn Leu Thr Phe Asp Ala Gln Val Leu Ile Ser Met Val
                100                 105                 110

Val Val Glu Pro Thr Lys Ser Ile Val Leu Asn Ala Lys Lys Ile Thr
                115                 120                 125

Ala Leu Pro Lys Glu Cys Glu Val Phe Ala Gly Asp Gln Lys Leu Asp
 130                 135                 140

Ile Glu Ser Val Thr Asp His Glu Arg Leu Glu Lys Leu Glu Phe Thr
 145                 150                 155                 160

Leu Lys Gln Gln Leu Glu Lys Asp Gln Lys Ile Gln Leu Lys Val Val
                165                 170                 175

Tyr Ser Gly Leu Ile Ser Asp Thr Leu Gly Gly Leu Tyr Gln Ala Thr
                180                 185                 190

Tyr Lys Asp Thr Asp Gly Thr Thr Lys Ile Val Ala Val Ser Gln Met
                195                 200                 205

Glu Pro Thr Asp Ala Arg Arg Met Val Pro Cys Phe Asp Glu Pro Ser
 210                 215                 220

Phe Lys Ala Asn Trp Thr Val Thr Ile Ile His Pro Arg Gly Thr Thr
 225                 230                 235                 240

Ala Ala Ser Asn Gly Ile Glu Thr Asn Gly Glu Gly Glu Pro Asp Gly
                245                 250                 255

Asp Trp Ile Thr Ser Lys Phe Lys Thr Thr Pro Arg Met Ser Ser Tyr
                260                 265                 270

Leu Leu Ala Val Ile Val Ser Glu Phe Lys Tyr Ile Glu Gly Arg Thr
                275                 280                 285

Lys Ser Gly Val Arg Phe Arg Ile Trp Ser Arg Pro Glu Ala Val Lys
                290                 295                 300

Met Thr Lys Phe Ala Leu Asp Ala Gly Val Arg Cys Leu Glu Phe Tyr
 305                 310                 315                 320

Glu Lys Phe Phe Asp Ile Arg Phe Pro Leu Glu Lys Gln Asp Met Val
                325                 330                 335

Ala Leu Pro Asp Phe Ser Ala Gly Ala Met Glu Asn Trp Gly
                340                 345                 350
```

(2) INFORMATION FOR SEQ ID NO:26:

(i) SEQUENCE CHARACTERISTICS:
        (A) LENGTH: 616 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

```
Gly Ala Met Glu Asn Trp Gly Leu Ile Thr Tyr Arg Glu Asn Ser Leu
  1               5                  10                  15

Leu Tyr Asp Glu Arg Tyr Tyr Ala Pro Leu Asn Lys Glu Arg Val Ala
             20                  25                  30

Ile Val Val Ala His Glu Leu Ala His Gln Trp Phe Gly Asn Leu Val
             35                  40                  45

Thr Leu Lys Trp Trp Asp Asp Leu Trp Leu Asn Glu Gly Phe Ala Thr
 50                  55                  60

Phe Val Glu Phe Ile Gly Ala Asp His Ile Ser Asn Gly Thr Phe Arg
 65                  70                  75                  80

Met Lys Asp Tyr Phe Arg Leu Asp Ala Leu Val Asp Ala Leu Glu Ala
             85                  90                  95

Asp Ala Val Ala Ser Ser His Pro Leu Ser Phe Lys Ile Asp Lys Ala
            100                 105                 110

Ser Glu Val Tyr Glu Ala Phe Asp Ala Ile Thr Tyr Ser Lys Gly Ala
            115                 120                 125

Ser Val Leu Thr Met Leu Gln Ala Leu Ile Gly Glu Glu Asn Phe Lys
            130                 135                 140

Gln Ala Val Thr Gln Tyr Leu Asn Lys Phe Ser Phe Asp Asn Ala Lys
145                 150                 155                 160

Ala Ser Asp Leu Trp Gly Val Phe Asp Glu Val Val Lys Asp Val Lys
                165                 170                 175

Gly Pro Asp Gly Asn Pro Met Lys Thr Thr Glu Phe Ala Tyr Gln Trp
            180                 185                 190

Thr Thr Gln Met Gly Tyr Pro Ile Val Thr Val Glu Thr Phe Asn Ala
            195                 200                 205

Thr Ser Leu Lys Val Ser Gln Asn Arg Tyr Lys Thr Asn Lys Asp Ala
            210                 215                 220

Gln Glu Pro Glu Lys Tyr Arg Pro Lys Tyr Gly Phe Lys Trp Asp
225                 230                 235                 240

Val Pro Leu Trp Tyr Gln Glu Gly Glu Ser Asn Glu Ile Lys Gln Thr
                245                 250                 255

Trp Leu Thr Arg Gly Glu Pro Leu Tyr Ser His Val Ser Ser Ser Asp
            260                 265                 270

Asp Ser Ile Val Val Asn Ala Asp Arg His Gly Phe Tyr Arg Gln Asn
            275                 280                 285

Tyr Asp Ala Asn Gly Trp Arg Lys Ile Ile Arg Gln Leu Lys Asp Asn
            290                 295                 300

His Glu Val Tyr Ser Pro Arg Thr Arg Asn Ala Ile Ile Ser Asp Ala
305                 310                 315                 320

Phe Ala Ala Ala Leu Leu Asp Asn Gly Leu Lys Tyr Glu Thr Val Phe
                325                 330                 335

Glu Leu Leu Glu Tyr Ala Lys Asn Glu Gln Glu Tyr Leu Pro Trp Asp
            340                 345                 350
```

```
Glu Ile Ile Ser Gly Phe Tyr Ser Ile Leu Glu Phe Phe Gly Asn Glu
        355                 360                 365

Pro Glu Ser Lys Trp Ala Lys Ser Tyr Met Met Asn Ile Leu Lys Pro
        370                 375                 380

Met Tyr Asp Asn Ser Ser Met Gln Tyr Ile Ala Asp Asn Tyr Lys Asn
385                     390                 395                 400

Asp Ser Leu Phe Phe Glu Asn Asn Leu Gln Lys Ala Val Ile Asp Ala
                405                 410                 415

Tyr Cys Arg Leu Gly Ser Lys Asp Cys Ile Gly Lys Tyr Lys Asp Leu
            420                 425                 430

Phe Ile Lys Glu Val Met Glu Lys Cys Glu Asp Asp Glu Glu Ala Ser
        435                 440                 445

Lys Cys Val Thr Val Ala Ala Pro Leu Arg Ser Arg Val Tyr Cys Tyr
    450                 455                 460

Gly Val Lys Glu Gly Gly Asp Asp Ala Phe Asp Lys Val Met Gly Leu
465                 470                 475                 480

Tyr Ser Ala Glu Asn Val Gln Leu Glu Lys Asp Ile Leu Leu Arg Ala
            485                 490                 495

Leu Gly Cys His Arg Asp Ile Thr Ala Leu Lys Gly Leu Leu Leu Arg
            500                 505                 510

Ala Leu Asp Arg Asn Ser Ser Phe Val Arg Leu Gln Lys Val Ser Asp
        515                 520                 525

Val Phe Met Ala Val Ser Gly Lys Pro Val Gly Glu Glu Phe Met Phe
        530                 535                 540

Asn Phe Leu Leu Glu Arg Trp Glu Glu Ile Val Glu Ser Leu Pro Ser
545                 550                 555                 560

Glu His Thr Ser Val Glu Lys Val Ile Arg Asp Cys Ser Thr Gly Ile
            565                 570                 575

Arg Ser Glu Gln Gln Ile Glu Gln Leu Arg Asn Leu His Lys Asn Gly
            580                 585                 590

Arg Asn Ala Arg Asp Tyr Gly Ala Phe Asp Glu Gly Ile Glu Arg Ala
        595                 600                 605

Glu His Lys Val Asp Trp Ile Lys
610                 615

(2) INFORMATION FOR SEQ ID NO:27:

(i) SEQUENCE CHARACTERISTICS:
        (A) LENGTH: 528 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Gly Ala Met Glu Asn Trp Gly Leu Ile Thr Tyr Arg Glu Thr Ala Leu
1               5                   10                  15

Leu Tyr Asp Glu Arg Leu Tyr Ala Pro Val Asn Lys Lys Arg Val Ala
            20                  25                  30

Ser Val Val Ala His Glu Leu Ser His Gln Trp Phe Gly Asp Leu Val
        35                  40                  45

Thr Met Glu Trp Trp Asp Asn Leu Asn Trp Leu Glu Gly Phe Ala Ser
    50                  55                  60

Gly Met Gln Tyr Ile Gly Thr Asn Glu Ile Thr Arg Asp Asn Phe Lys
65                  70                  75                  80
```

-continued

```
Met Lys Asp Tyr Phe Leu Val Asp Ser Phe Ala Gln Gly Met Glu Ala
                85                  90                  95

Asp Val Ala Ser Ser His Pro Leu Ser Phe Lys Val Asp Lys Ala Ala
            100                 105                 110

Asp Val Val Glu Ala Phe Asp Val Thr Tyr Arg Lys Gly Ala Ser
            115                 120                 125

Ile Leu Thr Met Leu Gln Ala Leu Ile Gly Glu Gln Asn Phe Gln Arg
    130                 135                 140

Ala Ile Arg Gln Tyr Leu Ile Lys Phe Ser Tyr Asn Asn Ala Asn Ala
145                 150                 155                 160

Ser Asp Leu Trp Asn Val Phe Asp Glu Val Val Lys Asp Val Ala Gly
                165                 170                 175

Pro Asp Gly Ser Arg Met Lys Thr Ser Glu Phe Ala Asp Gln Trp Thr
            180                 185                 190

Thr Gln Met Gly Tyr Pro Val Val Thr Val Glu Thr Phe Asn Ala Thr
            195                 200                 205

Thr Phe Lys Ile Ser Gln Ser Arg Tyr Lys Lys Asn Lys Asn Ala Gln
    210                 215                 220

Glu Pro Glu Lys Tyr Arg His Pro Lys Tyr Gly Phe Glu Trp Asp Val
225                 230                 235                 240

Pro Val Trp Tyr Gln Asp Ser Lys Asn Ser Asp Val Lys Arg Ile Trp
                245                 250                 255

Leu Thr Arg Asp Lys Pro Thr Tyr Leu His Val Asn Ser Ser Asp Ala
            260                 265                 270

Ser Ile Val Val Asn Ala Asp Arg His Gly Phe Tyr Arg Gln Asn Tyr
            275                 280                 285

Asp Glu Asp Gly Trp Arg Lys Ile Ile Lys Ile Leu Lys Asp Asn His
    290                 295                 300

Lys Tyr Tyr Ser Pro Arg Thr Arg Asn Ala Ile Ile Ser Asp Ala Phe
305                 310                 315                 320

Ala Ala Ala Leu Ile Asp Lys Leu Glu Tyr Glu Thr Val Phe Asp Leu
                325                 330                 335

Leu Glu Tyr Ala Asn Gln Glu Glu Glu Phe Leu Pro Trp Asn Glu Ile
            340                 345                 350

Ile Thr Gly Phe Tyr Ser Ile Leu Glu Tyr Phe Gly Ser Glu Pro Glu
            355                 360                 365

Ser Lys Phe Ala Lys Asn Tyr Met Met Ser Ile Leu Lys Pro Met Tyr
    370                 375                 380

Asp Lys Ser Ser Val Asp Tyr Ile Ala Glu Asn Tyr Thr Asn Asp Ser
385                 390                 395                 400

Leu Phe Phe Glu Asn Asn Leu Gln Lys Ala Ile Ile Glu Ala Tyr Cys
                405                 410                 415

Tyr Phe Gly Ser Lys Gly Cys Ile Gln Lys Phe Lys Glu Leu Phe Asp
            420                 425                 430

Lys Glu Val Val Gln Lys Cys Lys Gly Gly His Lys Ala Ser Lys Cys
            435                 440                 445

Val Asp Val Ala Ala Pro Leu Arg Ala Met Val Tyr Cys Tyr Gly Val
    450                 455                 460

Asn Glu Gly Gly Asp Asp Ala Tyr Asp Val Met Glu Leu Tyr Tyr
465                 470                 475                 480

Ala Glu Thr Val Gln Leu Glu Lys Asp Tyr Leu Leu Gly Ala Leu Ala
                485                 490                 495

Cys His Lys Asp Ile Thr Ala Leu Lys Gly Leu Leu Leu Leu Ala Leu
```

```
                    500             505             510
Asp Arg Asn Ser Ser Phe Val Arg Leu Gln Asp Met Ala Asn Val Ser
            515             520             525

(2) INFORMATION FOR SEQ ID NO:28:

(i) SEQUENCE CHARACTERISTICS:
        (A) LENGTH: 616 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Gly Ala Met Glu Asn Trp Gly Leu Ile Thr Tyr Arg Glu Asn Ser Leu
1               5                   10                  15

Leu Tyr Asp Glu Arg Tyr Tyr Ala Pro Leu Ser Lys Glu Arg Val Ala
            20                  25                  30

Ile Val Val Ala His Glu Leu Ala His Gln Trp Phe Gly Asn Leu Val
            35                  40                  45

Thr Leu Lys Trp Trp Asp Asp Leu Trp Leu Asn Glu Gly Phe Ala Thr
    50                  55                  60

Phe Val Glu Phe Ile Gly Ala Asp His Ile Ser Asn Gly Thr Phe Arg
65                  70                  75                  80

Met Lys Asp Tyr Phe Leu Leu Asp Ala Leu Val Asp Ala Leu Glu Ala
                85                  90                  95

Asp Ser Val Ala Ser Ser His Pro Leu Ser Phe Lys Ile Asp Lys Ala
            100                 105                 110

Ser Glu Val Tyr Glu Ala Phe Asp Ala Ile Thr Tyr Ser Lys Gly Ala
        115                 120                 125

Ser Val Leu Thr Met Leu Gln Ala Leu Ile Gly Glu Glu Asn Phe Lys
    130                 135                 140

Arg Ala Val Thr Gln Tyr Leu Asn Lys Phe Ser Phe Asp Asn Ala Lys
145                 150                 155                 160

Ala Ser Asp Leu Trp Gly Val Phe Asp Glu Val Val Lys Asp Val Lys
                165                 170                 175

Gly Pro Asp Gly Asn Pro Met Lys Ile Thr Glu Phe Ala Tyr Gln Trp
            180                 185                 190

Thr Thr Gln Met Gly Tyr Pro Ile Val Thr Val Glu Thr Phe Asn Ala
        195                 200                 205

Thr Ser Asp Lys Val Ser Gln Asn Arg Tyr Lys Thr Asn Lys Asp Ala
    210                 215                 220

Gln Glu Pro Glu Lys Tyr Arg His Pro Lys Tyr Gly Phe Lys Trp Asp
225                 230                 235                 240

Val Pro Leu Trp Tyr Gln Glu Gly Glu Ser Lys Glu Ile Lys Gln Thr
                245                 250                 255

Trp Leu Thr Arg Gly Glu Pro Leu Tyr Ser His Val Ser Ser Ser Asp
            260                 265                 270

Asp Ser Ile Val Val Asn Ala His Arg His Gly Phe Tyr Arg Gln Asn
        275                 280                 285

Tyr Asp Ala Asn Gly Trp Arg Lys Ile Ile Arg Gln Leu Lys Glu Asn
    290                 295                 300

His Glu Met Tyr Ser Pro Arg Thr Arg Asn Ala Ile Ile Ser Asp Ala
305                 310                 315                 320

Phe Ala Ala Ala Leu Leu Asp Asn Gly Leu Glu Tyr Glu Thr Val Phe
```

-continued

```
                325                 330                 335
Glu Leu Leu Glu Tyr Ala Lys Asn Glu Gln Glu Tyr Leu Pro Trp Asp
            340                 345                 350
Glu Ile Ile Ser Gly Phe Tyr Ser Ile Leu Glu Phe Phe Gly Asn Glu
            355                 360                 365
Pro Glu Ser Lys Trp Ala Lys Ala Tyr Thr Met Ser Ile Leu Lys Pro
370                 375                 380
Met Tyr Asp Asn Ser Ser Met Gln Tyr Ile Ala Glu Asn Tyr Lys Asn
385                 390                 395                 400
Asp Ser Leu Phe Phe Glu Asn Asn Leu Gln Lys Ala Val Ile Asp Ala
                405                 410                 415
Tyr Cys Arg Leu Gly Ser Lys Asp Cys Ile Gly Lys Tyr Lys Asp Leu
            420                 425                 430
Phe Val Lys Glu Val Met Glu Lys Cys Glu Asp Gly Glu Glu Ala Ser
            435                 440                 445
Lys Cys Val Thr Val Ala Ala Pro Leu Arg Ser Arg Val Tyr Cys Tyr
        450                 455                 460
Gly Val Lys Glu Gly Gly Asp Asp Ala Phe Asp Lys Val Met Gly Leu
465                 470                 475                 480
Tyr Ser Ala Glu Asn Val Gln Leu Glu Lys Asp Ile Leu Leu Arg Ala
                485                 490                 495
Leu Gly Cys His Arg Asp Ile Thr Ala Leu Lys Gly Leu Leu Leu Arg
            500                 505                 510
Ala Leu Asp Arg Asn Ser Ser Phe Val Arg Leu Gln Asp Val Ser Asp
            515                 520                 525
Val Phe Met Ala Val Ser Gly Asn Pro Val Gly Glu Glu Phe Met Phe
530                 535                 540
Asn Phe Leu Leu Glu Arg Trp Glu Glu Ile Ile Glu Ser Leu Pro Ser
545                 550                 555                 560
Glu His Thr Ser Val Glu Lys Val Ile Lys Asp Cys Ser Thr Gly Ile
                565                 570                 575
Arg Ser Glu Gln Gln Ile Glu Gln Leu Arg Asn Leu His Lys Asn Gly
            580                 585                 590
Arg Asn Ala Arg Asp Tyr Gly Ala Phe Asp Glu Gly Ile Glu Arg Ala
            595                 600                 605
Glu His Lys Val Asp Trp Tyr Lys
    610                 615

(2) INFORMATION FOR SEQ ID NO:29:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Ala Glu Glu Leu Arg Leu Pro Thr Thr Ile Lys Pro Leu Thr Tyr Asp
1               5                   10                  15
Leu Val (2) INFORMATION FOR SEQ ID NO:30:

(i) SEQUENCE CHARACTERISTICS:
        (A) LENGTH: 18 amino acids
```

(B) TYPE: amino acid
            (C) STRANDEDNESS:
            (D) TOPOLOGY: linear (ii) MOLECULE TYPE: peptide (xi) SEQUENCE DESCRIPTION: SEQ ID NO:30:

Ala Glu Glu Leu Leu Leu Pro Thr Asn Ile Lys Pro Val Ser Tyr Asp
1               5                   10                  15

Leu Asn (2) INFORMATION FOR SEQ ID NO:31:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Ala Ala Glu Leu Leu Leu Pro Ser Asn Ile Lys Pro Leu Ser Tyr Asp
1               5                   10                  15

Leu Thr (2) INFORMATION FOR SEQ ID NO:32:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Ala Glu Glu Leu Leu Leu Pro Thr Asn Ile Lys Pro Val Ser Tyr Asp
1               5                   10                  15

Leu Lys (2) INFORMATION FOR SEQ ID NO:33:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:33:

GACTCGAGTC GACATCGATT TTTTTTTTTT TTTTT                                35

(2) INFORMATION FOR SEQ ID NO:34:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: cDNA (iv) ANTI-SENSE: YES (xi) SEQUENCE DESCRIPTION: SEQ ID NO:34:

GACTCGAGTC GACATCGA                                                          18

(2) INFORMATION FOR SEQ ID NO:35:

(i) SEQUENCE CHARACTERISTICS:
        (A) LENGTH: 362 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:35:

```
Met Ala Lys Gly Phe Tyr Ile Ser Lys Thr Leu Gly Ile Leu Gly Ile
1               5                   10                  15

Leu Leu Gly Val Ala Ala Val Cys Thr Ile Ile Ala Leu Ser Val Val
            20                  25                  30

Tyr Ala Gln Glu Lys Asn Arg Asn Ala Glu Asn Ser Ala Ile Ala Pro
        35                  40                  45

Thr Leu Pro Gly Ser Thr Ser Ala Thr Thr Ser Thr Asn Pro Ala
    50                  55                  60

Ile Asp Glu Ser Lys Pro Trp Asn Gln Tyr Arg Leu Pro Lys Thr Leu
65                  70                  75                  80

Ile Pro Asp Ser Tyr Gln Val Thr Leu Arg Pro Tyr Leu Thr Pro Asn
                85                  90                  95

Glu Gln Gly Leu Tyr Ile Phe Lys Gly Ser Ser Thr Val Arg Phe Thr
                100                 105                 110

Cys Asn Glu Thr Thr Asn Val Ile Ile Ile His Ser Lys Lys Leu Asn
            115                 120                 125

Tyr Thr Asn Lys Gly Asn His Arg Val Ala Leu Arg Ala Leu Gly Asp
    130                 135                 140

Thr Pro Ala Pro Asn Ile Asp Thr Thr Glu Leu Val Glu Arg Thr Glu
145                 150                 155                 160

Tyr Leu Val Val His Leu Gln Gly Ser Leu Val Lys Gly His Gln Tyr
                165                 170                 175

Glu Met Asp Ser Glu Phe Gln Gly Glu Leu Ala Asp Asp Leu Ala Gly
            180                 185                 190

Phe Tyr Arg Ser Glu Tyr Met Glu Gly Gly Asn Lys Lys Val Val Ala
        195                 200                 205

Thr Thr Gln Met Gln Ala Ala Asp Ala Arg Lys Ser Phe Pro Cys Phe
    210                 215                 220

Asp Glu Pro Ala Met Lys Ala Ser Phe Asn Ile Thr Leu Ile His Pro
225                 230                 235                 240

Asn Asn Leu Thr Ala Leu Ser Asn Met Leu Pro Lys Asp Ser Arg Thr
                245                 250                 255

Leu Gln Glu Asp Pro Ser Trp Asn Val Thr Glu Phe His Pro Thr Pro
            260                 265                 270

Lys Met Ser Thr Tyr Leu Leu Ala Tyr Ile Val Ser Glu Phe Lys Tyr
        275                 280                 285

Val Glu Ala Val Ser Pro Asn Arg Val Gln Ile Arg Ile Trp Ala Arg
    290                 295                 300

Pro Ser Ala Ile Asp Glu Gly His Gly Asp Tyr Ala Leu Gln Val Thr
305                 310                 315                 320

Gly Pro Ile Leu Asn Phe Phe Ala Gln His Tyr Asn Thr Ala Tyr Pro
                325                 330                 335
```

```
Leu Glu Lys Ser Asp Gln Ile Ala Leu Pro Asp Phe Asn Ala Gly Ala
            340                 345                 350

Met Glu Asn Trp Gly Leu Val Thr Tyr Arg
            355                 360
```

(2) INFORMATION FOR SEQ ID NO:36:

(i) SEQUENCE CHARACTERISTICS:
        (A) LENGTH: 608 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

```
Ser Asp Gln Ile Ala Leu Pro Asp Phe Asn Ala Gly Ala Met Glu Asn
1               5                   10                  15

Trp Gly Leu Val Thr Tyr Arg Glu Ser Ala Leu Val Phe Asp Pro Gln
            20                  25                  30

Ser Ser Ser Ile Ser Asn Lys Glu Arg Val Val Thr Val Ile Ala His
            35                  40                  45

Glu Leu Ala His Gln Trp Phe Gly Asn Leu Val Thr Val Asp Trp Trp
 50                  55                  60

Asn Asp Leu Trp Leu Asn Glu Gly Phe Ala Ser Tyr Val Glu Phe Leu
 65                  70                  75                  80

Gly Ala Asp Tyr Ala Glu Pro Thr Trp Asn Leu Lys Asp Leu Ile Val
                85                  90                  95

Leu Asn Asp Val Tyr Arg Val Met Ala Val Asp Ala Leu Ala Ser Ser
                100                 105                 110

His Pro Leu Ser Ser Pro Ala Asn Glu Val Asn Thr Pro Ala Gln Ile
            115                 120                 125

Ser Glu Leu Phe Asp Ser Ile Thr Tyr Ser Lys Gly Ala Ser Val Leu
            130                 135                 140

Arg Met Leu Ser Ser Phe Leu Thr Glu Asp Leu Phe Lys Lys Gly Leu
145                 150                 155                 160

Ser Ser Tyr Leu His Thr Phe Gln Tyr Ser Asn Thr Ile Tyr Leu Asp
                165                 170                 175

Leu Trp Glu His Leu Gln Gln Ala Val Asp Ser Gln Thr Ala Ile Lys
            180                 185                 190

Leu Pro Ala Ser Val Ser Thr Ile Met Asp Arg Trp Ile Leu Gln Met
            195                 200                 205

Gly Phe Pro Val Ile Thr Val Asn Thr Ser Thr Gly Glu Ile Tyr Gln
 210                 215                 220

Glu His Phe Leu Leu Asp Pro Thr Ser Lys Pro Thr Arg Pro Ser Asp
225                 230                 235                 240

Phe Asn Tyr Leu Trp Ile Val Pro Ile Pro Tyr Leu Lys Asn Gly Lys
                245                 250                 255

Glu Asp His Tyr Trp Leu Glu Thr Lys Asn Gln Ser Ala Glu Phe
            260                 265                 270

Gln Thr Ser Ser Asn Glu Trp Leu Leu Leu Asn Ile Asn Val Thr Gly
            275                 280                 285

Tyr Tyr Gln Val Asn Tyr Asp Glu Asn Asn Trp Arg Lys Ile Gln Asn
            290                 295                 300

Gln Leu Gln Thr Asp Leu Ser Val Ile Pro Val Ile Asn Arg Ala Gln
305                 310                 315                 320
```

```
Ile Ile His Asp Ser Phe Asn Leu Ala Ser Ala Gly Lys Leu Ser Ile
            325                 330                 335

Thr Leu Pro Leu Ser Asn Thr Leu Phe Leu Ala Ser Glu Thr Glu Tyr
            340                 345                 350

Met Pro Trp Glu Ala Ala Leu Ser Ser Leu Asn Tyr Phe Lys Leu Met
            355                 360                 365

Phe Asp Arg Ser Glu Val Tyr Gly Pro Met Lys Arg Tyr Leu Lys Lys
            370                 375                 380

Gln Val Thr Pro Leu Phe Ala Tyr Phe Lys Ile Lys Thr Asn Asn Trp
385                 390                 395                 400

Leu Asp Arg Pro Pro Thr Leu Met Glu Gln Tyr Asn Glu Ile Asn Ala
            405                 410                 415

Ile Ser Thr Ala Cys Ser Ser Gly Leu Glu Glu Cys Arg Asp Leu Val
            420                 425                 430

Val Gly Leu Tyr Ser Gln Trp Met Asn Asn Ser Asp Asn Asn Pro Ile
            435                 440                 445

His Pro Asn Leu Arg Ser Thr Val Tyr Cys Asn Ala Ile Ala Phe Gly
            450                 455                 460

Gly Glu Glu Glu Trp Asn Phe Ala Trp Glu Gln Phe Arg Lys Ala Thr
465                 470                 475                 480

Leu Val Asn Glu Ala Asp Lys Leu Arg Ser Ala Leu Ala Cys Ser Asn
            485                 490                 495

Glu Val Trp Ile Leu Asn Arg Tyr Leu Ser Tyr Thr Leu Asn Pro Asp
            500                 505                 510

Tyr Ile Arg Lys Gln Asp Ala Thr Ser Thr Ile Val Ser Ile Ala Asn
            515                 520                 525

Asn Val Val Gly Gln Thr Leu Val Trp Asp Phe Val Arg Ser Asn Trp
530                 535                 540

Lys Lys Leu Phe Glu Asp Tyr Gly Gly Ser Phe Ser Phe Ala Asn
545                 550                 555                 560

Leu Ile Gln Gly Val Thr Arg Arg Phe Ser Ser Glu Phe Glu Leu Gln
            565                 570                 575

Gln Leu Glu Gln Phe Lys Glu Asp Asn Ser Ala Thr Gly Phe Gly Ser
            580                 585                 590

Gly Thr Arg Ala Leu Glu Gln Ala Leu Glu Lys Thr Lys Ala Asn Ile
            595                 600                 605
```

(2) INFORMATION FOR SEQ ID NO:37:

(i) SEQUENCE CHARACTERISTICS:
        (A) LENGTH: 359 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Met Asn Phe Ala Glu Glu Glu Pro Ser Lys Lys Tyr Cys Ile Lys Gly
1                   5                   10                  15

Lys His Val Ala Ile Ile Cys Gly Val Val Ala Val Gly Leu Ile
            20                  25                  30

Val Gly Leu Ser Val Gly Leu Thr Arg Ser Cys Glu Gln Asp Thr Thr
            35                  40                  45

Pro Ala Pro Ser Gln Pro Pro Pro Glu Ala Ser Thr Ala Leu Pro Pro
50                  55                  60
```

```
Gln Asp Gln Asn Val Cys Pro Asp Ser Glu Asp Glu Ser Gly Glu Trp
 65                  70                  75                  80

Lys Asn Phe Arg Leu Pro Asp Phe Ile Asn Pro Val His Tyr Asp Leu
                 85                  90                  95

Glu Val Lys Ala Leu Met Glu Glu Asp Arg Tyr Thr Gly Ile Val Thr
            100                 105                 110

Ile Ser Val Asn Leu Ser Lys Pro Thr Arg Asp Leu Trp Leu His Ile
            115                 120                 125

Arg Glu Thr Lys Ile Thr Lys Leu Pro Glu Leu Arg Arg Pro Ser Gly
        130                 135                 140

Glu Gln Val Pro Ile Arg Arg Cys Phe Glu Tyr Lys Lys Gln Glu Tyr
145                 150                 155                 160

Val Val Ile Gln Ala Ala Glu Asp Leu Ala Ala Thr Ser Gly Asp Ser
                165                 170                 175

Val Tyr Arg Leu Thr Met Glu Phe Lys Gly Trp Leu Asn Gly Ser Leu
                180                 185                 190

Val Gly Phe Tyr Lys Thr Thr Tyr Met Glu Asp Gly Gln Ile Arg Ser
            195                 200                 205

Ile Ala Ala Thr Asp His Glu Pro Thr Asp Ala Arg Lys Ser Phe Pro
        210                 215                 220

Cys Phe Asp Glu Pro Asn Lys Lys Ser Thr Tyr Ser Ile Ser Ile Ile
225                 230                 235                 240

His Pro Lys Glu Tyr Ser Ala Leu Ser Asn Met Pro Glu Glu Lys Ser
                245                 250                 255

Glu Met Val Asp Asp Asn Trp Lys Lys Thr Thr Phe Val Lys Ser Val
            260                 265                 270

Pro Met Ser Thr Tyr Leu Val Cys Phe Ala Val His Arg Phe Thr Ala
        275                 280                 285

Ile Glu Arg Lys Ser Arg Ser Gly Lys Pro Leu Lys Val Tyr Val Gln
        290                 295                 300

Pro Asn Gln Lys Glu Thr Ala Glu Tyr Ala Ala Asn Ile Thr Gln Ala
305                 310                 315                 320

Val Phe Asp Tyr Phe Glu Asp Tyr Phe Ala Met Glu Tyr Ala Leu Pro
                325                 330                 335

Lys Leu Asp Lys Ile Ala Ile Pro Asp Phe Gly Thr Gly Ala Met Glu
                340                 345                 350

Asn Trp Gly Leu Val Thr Tyr
            355

(2) INFORMATION FOR SEQ ID NO:38:

(i) SEQUENCE CHARACTERISTICS:
        (A) LENGTH: 593 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Ala Met Glu Asn Trp Gly Leu Val Thr Tyr Arg Glu Thr Asn Leu Leu
  1               5                  10                  15

Tyr Asp Pro Leu Leu Ser Ala Ser Ser Asn Gln Gln Arg Val Ala Ser
                 20                  25                  30

Val Val Ala His Glu Leu Val His Gln Trp Phe Gly Asn Thr Val Thr
            35                  40                  45
```

```
Met Asp Trp Trp Asp Asp Leu Trp Leu Asn Glu Gly Phe Ala Ser Phe
    50                  55                  60
Phe Glu Phe Leu Gly Val Asn His Ala Glu Lys Asp Trp Gln Met Leu
65              70                  75                  80
Ser Gln Val Leu Leu Glu Asp Val Phe Pro Val Gln Glu Asp Asp Ser
                85                  90                  95
Leu Met Ser Ser His Pro Val Val Thr Val Ser Thr Pro Ala Glu
            100                 105                 110
Ile Thr Ser Val Phe Asp Gly Ile Ser Tyr Ser Lys Gly Ala Ser Ile
            115                 120                 125
Leu Arg Met Leu Gln Asp Trp Ile Thr Pro Glu Lys Phe Gln Lys Gly
        130                 135                 140
Cys Gln Ile Tyr Leu Lys Lys Phe Gln Phe Ala Asn Ala Lys Thr Ser
145             150                 155                 160
Asp Phe Trp Asp Ser Leu Gln Glu Ala Ser Asn Leu Pro Val Lys Glu
                165                 170                 175
Val Met Asp Thr Trp Thr Ser Gln Met Gly Tyr Pro Val Val Thr Val
            180                 185                 190
Ser Gly Arg Gln Asn Ile Thr Gln Lys Arg Phe Leu Leu Asp Ser Lys
        195                 200                 205
Ala Asp Pro Ser Gln Pro Pro Ser Glu Leu Gly Tyr Thr Trp Asn Ile
    210                 215                 220
Pro Val Arg Trp Ala Asp Asn Asp Asn Ser Arg Ile Thr Val Tyr Asn
225                 230                 235                 240
Arg Leu Asp Lys Gly Gly Ile Thr Leu Asn Ala Asn Leu Ser Gly Asp
                245                 250                 255
Ala Phe Leu Lys Ile Asn Pro Asp His Ile Gly Phe Tyr Arg Val Asn
            260                 265                 270
Tyr Glu Gly Gly Thr Trp Asp Trp Ile Ala Glu Ala Leu Ser Ser Asn
        275                 280                 285
His Thr Arg Phe Ser Ala Ala Asp Arg Ser Ser Phe Ile Asp Asp Ala
    290                 295                 300
Phe Ala Leu Ala Arg Ala Gln Leu Leu Asn Tyr Lys Ile Ala Leu Asn
305                 310                 315                 320
Leu Thr Met Tyr Leu Lys Ser Glu Glu Asp Phe Leu Pro Trp Glu Arg
                325                 330                 335
Val Ile Ser Ser Val Ser Tyr Ile Ile Ser Met Phe Glu Asp Asp Arg
            340                 345                 350
Glu Leu Tyr Pro Met Ile Glu Thr Tyr Phe Gln Gly Gln Val Lys Pro
        355                 360                 365
Val Ala Asp Leu Leu Gly Trp Gln Asp Thr Gly Ser His Ile Thr Lys
    370                 375                 380
Leu Leu Arg Ala Ser Ile Leu Gly Phe Ala Cys Lys Met Gly Asp Arg
385                 390                 395                 400
Glu Ala Leu Gly Asn Ala Ser Gln Leu Phe Asp Ser Trp Leu Lys Gly
                405                 410                 415
Ser Ala Ser Ile Pro Val Asn Leu Arg Leu Leu Val Tyr Arg Tyr Gly
            420                 425                 430
Met Gln Asn Ser Gly Asn Glu Ala Ala Trp Asn Tyr Thr Leu Glu Gln
        435                 440                 445
Tyr Gln Lys Thr Ser Leu Ala Gln Glu Lys Glu Lys Leu Leu Tyr Gly
    450                 455                 460
```

```
Leu Ala Ser Val Lys Asp Val Lys Leu Leu Ala Arg Tyr Leu Glu Met
465                 470                 475                 480

Leu Lys Asp Pro Asn Ile Ile Lys Thr Gln Asp Val Phe Thr Val Ile
            485                 490                 495

Arg Tyr Ile Ser Tyr Asn Ser Tyr Gly Lys Thr Met Ala Trp Asn Trp
            500                 505                 510

Ile Gln Leu Asn Trp Asp Tyr Leu Val Ser Arg Phe Thr Ile Asn Asp
    515                 520                 525

Arg Tyr Leu Gly Arg Ile Val Thr Ile Ala Glu Pro Phe Asn Thr Glu
530                 535                 540

Leu Gln Leu Trp Gln Met Gln Ser Phe Phe Ala Lys Tyr Pro Asn Ala
545                 550                 555                 560

Gly Ala Gly Ala Lys Pro Arg Glu Gln Val Leu Glu Thr Val Lys Asn
                565                 570                 575

Asn Ile Glu Trp Leu Asn Val Asn Arg Gln Ser Ile Arg Glu Trp Phe
            580                 585                 590

Ala (2) INFORMATION FOR SEQ ID NO:39:

(i) SEQUENCE CHARACTERISTICS:
        (A) LENGTH: 350 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Met Thr Ser Gln Gly Arg Thr Arg Thr Leu Leu Asn Leu Thr Pro Ile
1               5                   10                  15

Arg Leu Ile Val Ala Leu Phe Leu Val Ala Ala Val Gly Leu Ser
            20                  25                  30

Ile Gly Leu Thr Tyr Tyr Phe Thr Arg Lys Ala Phe Asp Thr Ser Glu
            35                  40                  45

Lys Pro Gly Lys Asp Asp Thr Gly Gly Lys Asp Lys Asp Asn Ser Pro
    50                  55                  60

Ser Ala Ala Glu Leu Leu Leu Pro Ser Asn Ile Lys Pro Leu Ser Tyr
65                  70                  75                  80

Asp Leu Thr Ile Lys Thr Tyr Leu Pro Gly Tyr Val Asp Phe Pro Pro
                85                  90                  95

Glu Lys Asn Leu Thr Phe Asp Gly Arg Val Glu Ile Ser Met Val Val
            100                 105                 110

Ile Glu Pro Thr Lys Ser Ile Val Leu Asn Ser Lys Lys Ile Ser Val
            115                 120                 125

Ile Pro Gln Glu Cys Glu Leu Val Ser Gly Asp Lys Lys Leu Glu Ile
    130                 135                 140

Glu Ser Val Lys Glu His Pro Arg Leu Glu Lys Val Glu Phe Leu Ile
145                 150                 155                 160

Lys Ser Gln Leu Glu Lys Asp Gln Gln Ile Leu Leu Lys Val Gly Tyr
                165                 170                 175

Ile Gly Leu Ile Ser Asn Ser Phe Gly Gly Ile Tyr Gln Thr Thr Tyr
            180                 185                 190

Thr Thr Pro Asp Gly Thr Pro Lys Ile Ala Ala Val Ser Gln Asn Glu
    195                 200                 205

Pro Ile Asp Ala Arg Arg Met Val Pro Cys Met Asp Glu Pro Lys Tyr
```

-continued

```
                     210                 215                 220
Lys Ala Asn Trp Thr Val Thr Val Ile His Pro Lys Gly Thr Lys Ala
225                     230                 235                 240

Val Ser Asn Gly Ile Glu Val Asn Gly Asp Gly Glu Ile Ser Gly Asp
                245                 250                 255

Trp Ile Thr Ser Lys Phe Leu Thr Thr Pro Arg Met Ser Ser Tyr Leu
                260                 265                 270

Leu Ala Val Met Val Ser Glu Phe Glu Tyr Ile Glu Gly Glu Thr Lys
                275                 280                 285

Thr Gly Val Arg Phe Arg Ile Trp Ser Arg Pro Glu Ala Lys Lys Met
                290                 295                 300

Thr Gln Tyr Ala Leu Gln Ser Gly Ile Lys Cys Ile Glu Phe Tyr Glu
305                 310                 315                 320

Asp Phe Asp Ile Arg Phe Pro Leu Lys Lys Gln Asp Met Ile Ala
                325                 330                 335

Leu Pro Asp Phe Ser Ala Gly Ala Met Glu Asn Trp Gly Leu
                340                 345                 350

(2) INFORMATION FOR SEQ ID NO:40:

(i) SEQUENCE CHARACTERISTICS:
        (A) LENGTH: 620 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Phe Ser Ala Gly Ala Met Glu Asn Trp Gly Leu Ile Thr Tyr Arg Glu
1                   5                   10                  15

Asn Ser Leu Leu Tyr Asp Asp Arg Phe Tyr Ala Pro Met Asn Lys Gln
                20                  25                  30

Arg Ile Ala Arg Ile Val Ala His Glu Leu Ala His Gln Trp Phe Gly
                35                  40                  45

Asp Leu Val Thr Met Lys Trp Trp Asp Asn Leu Trp Leu Asn Glu Gly
50                  55                  60

Phe Ala Arg Phe Thr Glu Phe Ile Gly Ala Gly Gln Ile Thr Gln Asp
65                  70                  75                  80

Asp Ala Arg Met Arg Asn Tyr Phe Leu Ile Asp Val Leu Glu Arg Ala
                85                  90                  95

Leu Lys Ala Asp Ser Val Ala Ser Ser His Pro Leu Ser Phe Arg Ile
                100                 105                 110

Asp Lys Ala Ala Glu Val Glu Glu Ala Phe Asp Asp Ile Thr Tyr Ala
                115                 120                 125

Lys Gly Ala Ser Val Leu Thr Met Leu Arg Ala Leu Ile Gly Glu Glu
                130                 135                 140

Lys His Lys His Ala Val Ser Gln Tyr Leu Lys Lys Phe Ser Tyr Ser
145                 150                 155                 160

Asn Ala Glu Ala Thr Asp Leu Trp Ala Val Phe Asp Glu Val Val Thr
                165                 170                 175

Asp Val Glu Gly Pro Asp Gly Lys Pro Met Lys Thr Thr Glu Phe Ala
                180                 185                 190

Ser Gln Trp Thr Thr Gln Met Gly Phe Pro Val Ile Ser Val Ala Glu
                195                 200                 205

Phe Asn Ser Thr Thr Leu Lys Leu Thr Gln Ser Arg Tyr Glu Ala Asn
```

-continued

```
            210                 215                 220
Lys Asp Ala Val Glu Lys Glu Lys Tyr Arg His Pro Lys Tyr Gly Phe
225                 230                 235                 240

Lys Trp Asp Ile Pro Leu Trp Tyr Gln Glu Gly Asp Lys Lys Glu Ile
                245                 250                 255

Lys Arg Thr Trp Leu Arg Arg Asp Glu Pro Leu Tyr Leu His Val Ser
                260                 265                 270

Asp Ala Gly Ala Pro Phe Val Val Asn Ala Asp Arg Tyr Gly Phe Tyr
                275                 280                 285

Arg Gln Asn His Asp Ala Asn Gly Trp Lys Lys Ile Ile Lys Gln Leu
                290                 295                 300

Lys Asp Asn His Glu Val Tyr Ser Pro Arg Thr Arg Asn Val Ile Ile
305                 310                 315                 320

Ser Asp Ala Phe Ala Ala Ala Thr Asp Ala Ile Glu Tyr Glu Thr
                325                 330                 335

Val Phe Glu Leu Leu Asn Tyr Ala Glu Lys Glu Thr Glu Tyr Leu Pro
                340                 345                 350

Leu Glu Ile Ala Met Ser Gly Ile Ser Ser Ile Leu Lys Tyr Phe Pro
                355                 360                 365

Thr Glu Pro Glu Ala Lys Pro Ala Gln Thr Tyr Met Met Asn Ile Leu
                370                 375                 380

Lys Pro Met Tyr Glu Lys Ser Ser Ile Asp Phe Ile Ala Asn Asn Tyr
385                 390                 395                 400

Arg Asn Asp Lys Leu Phe Phe Gln Ile Asn Leu Gln Lys Asp Val Ile
                405                 410                 415

Asp Met Phe Cys Ala Leu Gly Ser Gln Asp Cys Arg Lys Lys Tyr Lys
                420                 425                 430

Lys Leu Phe Asp Asp Glu Val Met Asn Lys Cys Arg Asp Gly Gln Ala
                435                 440                 445

Ala Thr Glu Cys Val Arg Ile Ala Ala Pro Leu Arg Ser Ser Val Tyr
                450                 455                 460

Cys Tyr Gly Val Lys Glu Gly Gly Asp Tyr Ala Ser Asp Lys Val Met
465                 470                 475                 480

Glu Leu Tyr Thr Ala Glu Thr Leu Ala Leu Glu Lys Asp Phe Leu Arg
                485                 490                 495

Leu Ala Leu Gly Cys His Lys Asp Val Thr Ala Leu Lys Gly Leu Leu
                500                 505                 510

Leu Arg Ala Leu Asp Arg Asn Ser Ser Phe Val Arg Met Gln Asp Ile
                515                 520                 525

Pro Ser Ala Phe Asn Asp Val Ala Ala Asn Pro Ile Gly Glu Glu Phe
                530                 535                 540

Ile Phe Asn Phe Leu Ile Glu Arg Trp Pro Asp Ile Ile Glu Ser Ile
545                 550                 555                 560

Gly Thr Lys His Thr Tyr Val Glu Lys Val Ile Pro Ala Cys Thr Ser
                565                 570                 575

Gly Ile Arg Ser Gln Gln Gln Ile Asp Gln Leu Lys Asn Leu Gln Lys
                580                 585                 590

Asn Gly Met Asn Ala Arg Gln Phe Gly Ala Phe Asp Lys Ala Ile Glu
                595                 600                 605

Arg Ala Gln Asn Arg Val Asp Trp Ile Lys Lys His
610                 615                 620
```

-continued (2) INFORMATION FOR SEQ ID NO:41:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

```
Ala Glu Glu Leu Arg Leu Pro Ser Val Ile Pro Pro Leu Leu Tyr Asp
1               5                   10                  15
Leu Ser
```

(2) INFORMATION FOR SEQ ID NO:42:

(i) SEQUENCE CHARACTERISTICS:
        (A) LENGTH: 18 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:42:

```
Ala Glu Glu Leu Arg Leu Pro Thr Asn Ile Lys Pro Leu Leu Tyr Asn
1               5                   10                  15
Leu Thr
```

(2) INFORMATION FOR SEQ ID NO:43:

(i) SEQUENCE CHARACTERISTICS:
        (A) LENGTH: 8 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:43:

```
Gly Ala Met Glu Asn Trp Glu Leu
1               5
```

HELMINTH PARASITE ANTIGEN WITH AMINOPEPTIDASE-LIKE ACTIVITY

This application is a National Stage Application of PCT/GB94/02414.

This invention relates to novel helminth parasite antigens and their use in the control of disease caused by helminth parasites, particularly parasitic nematodes of the gastrointestinal tract of mammals.

Helminth parasites, particularly nematodes, infect or infest a wide range of animals, including man, and are a widespread and significant source of disease and ill-thrift, not only in animals, but also in man. Such parasites thus represent a considerable worldwide drain on economic resources. This is particularly true in animal husbandry, where parasite infections of grazing animals, such as sheep and cattle, are often difficult and expensive to control and may result in significant economic losses.

Particular mention may be made in this regard of the non-blood feeding nematodes *Ostertagia ostertagi* and *Ostertagia (Teladorsagia) circumcincta* (*O. circumcincta* has recently been reclassified as *T.circumcincta*, although the new name is not yet in wide usage).

Other parasitic helminths of economic importance include the various species of the following helminth families: Trichostrongylus, Nematodirus, Dictyocaulus, Cooperia, Trichuris, Oesophagostomum, Bunostomum and Metastrongylus. In addition to domestic livestock, pets and humans may also be infected, not infrequently with fatal results.

At present, control of helminth parasites of grazing livestock relies primarily on the use of anthelmintic drugs, combined with pasture management. Such techniques have not proved entirely satisfactory however, due to their expense and inconvenience and to a rapid increase in drug resistance. Anthelmintic drugs need to be administered frequently and appropriate pasture management is often not possible on some farms and even where it is, it can place constraints on the best use of available grazing.

To overcome these problems, attempts have been made to achieve immunological means of control. Although there has been some success in identifying certain protective antigens as potential vaccine candidates, most notably in Haemonchus, this approach has proved difficult and, other than for the cattle lungworm *Dictyocaulus viviparus*, has yet to come to commercial fruition.

The most success to date has been achieved with the protein doublet H110D, an integral membrane protein isolated from the gut of *H.contortus* and described by Munn in WO88/00835. H110D now represents the most promising vaccine candidate to date.

Munn has also described and proposed as a vaccine, contortin, a helical polymeric extracellular protein associated with the luminal surface of *H.contortus* intestinal cells (Munn et al., Parasitology 94: 385–397, 1987).

A third Haemonchus gut membrane protein with protective antigenic properties has also been discovered and termed H45 (Munn and Smith, WO90/11086).

Whilst proteins such as H110 D and H45 can be used as the basis for a vaccine against Haemonchus, there is nonetheless a continuing need for new and improved helminth parasite vaccines and in particular for a vaccine which may be used across a broad range of helminth genera. Most studies to date have concentrated on blood feeding nematodes such as Haemonchus and there is especially a need for vaccines against non-blood feeding helminths such as Trichostrongylus, Cooperia, Dictyocaulus, and particularly Ostertagia.

The present invention accordingly seeks to provide novel antigens for use as helminth parasite vaccines and in particular as protective immunogens in the control of diseases caused by non-blood feeding helminth parasites.

More specifically, the present invention is based on the finding that the gut of non-blood feeding nematodes such as Ostertagia and Cooperia contains an integral membrane protein having aminopeptidase activity which is believed to be an important protective antigen capable of conferring protective immunity against helminth parasites in animals. Such proteins, when liberated from the membranes in which they are integral, for example by the use of detergents, are novel and of use in the manufacture of vaccines against helminth infections.

According to one aspect, the present invention thus provides a protective helminth parasite antigen which is characterised by possessing aminopeptidase-like activity and which, in native form, is an integral membrane protein associated with the gut microvilli of a non-obligate blood feeding helminth parasite, or a functionally-equivalent variant, or antigenic fragment or precursor thereof.

A further aspect of the invention provides such protective antigens, and functionally-equivalent variants, antigenic fragments or precursors thereof, for use in stimulating an immune response against helminth parasites in a human or non-human, preferably mammalian, especially preferably ruminant, animal.

A precursor for the antigen in question may be a larger protein which is processed, eg. by proteolysis, to yield the antigen per se. Such precursors may take the form of zymogens ie. inactive precursors of enzymes, activated by proteolytic cleavage, for example analogous to the pepsin/pepsinogen system or the well known zymogens involved in the blood clotting cascade.

Non-obligate blood feeding parasites are defined for present purposes as those which imbibe host blood rarely and seemingly incidentally (in contrast to obligate blood feeders such as Haemonchus, which feed almost exclusively on host blood) and include both plug feeders and browsers. Plug-feeding worms have enlarged buccal capsules which they use to envelope a plug of host tissue e.g. the intestinal mucosa in the case of *Chabertia ovina*) from which they obtain nutrient. Browsing nematodes do not have mouthparts specialised for attachment. The composition of their diet is not known but is thought to consist either of host tissue, extracellular tissue fluid, mucus or, in the case of gastro-intestinal species, host digesta. Some gastrointestinal species, particularly those which live in close association with the mucosa (e.g. *Osteragia circumcincta* in the abomasal glands and certain Trichostrongylus species (e.g. other than T.axei) which tunnel under the intestinal epithelium may feed on a mixture of these.

Economically important helminth parasites which are not obligate blood feeders include the following genera and their subspecies: Ostertagia (which, for the avoidance of doubt, as used herein includes Teladorsagia), Trichostrongylus spp. (e.g. *T.colubriformis*, *T.vitrinus* and *T.axei*), Cooperia spp., Nematodirus, Chabertia and Oesophagostomum.

The novel antigens of the invention are not recognised by sera from naturally immune animals. In other words, they are not normally, in native form, accessible to the immune system of the infected host and are thus "hidden", "concealed" or "cryptic" antigens.

The term "protective antigens" or "protective antigenic activity" as used herein defines those antigens and their fragments or precursors, capable of generating a host-protective, ie. immunogenic, immune response, that is a response by the host which leads to generation of immune effector molecules, antibodies or cells which damage, inhibit or kill the parasite and thereby "protect" the host from clinical or sub-clinical disease and loss of productivity. Such a protective immune response may commonly be manifested by the generation of antibodies which are able to inhibit the metabolic function of the parasite, leading to stunting, lack of egg production and/or death.

As mentioned above, included within the scope of the invention are functionally-equivalent variants of the novel antigens and their fragments and precursors. "Functionally-equivalent" is used herein to define proteins related to or derived from the native protein, where the amino acid sequence has been modified by single or multiple amino acid substitution, addition and/or deletion and also sequences where the amino acids have been chemically modified, including by deglycosylation or glycosylation, but which nonetheless retain protective antigenic activity eg. are capable of raising host protective antibodies and/or functional immunity against the parasites. Within the meaning of "addition" variants are included amino and/or carboxyl terminal fusion proteins or polypeptides, comprising an additional protein or polypeptide fused to the aminopeptidase antigen sequence. Such functionally-equivalent variants mentioned above include natural biological variations (eg. allelic variants or geographical variations within a species) and derivatives prepared using known techniques. For example, functionally-equivalent proteins may be prepared either by chemical peptide synthesis or in recombinant form using the known techniques of site-directed mutagenesis, random mutagenesis, or enzymatic cleavage and/or ligation of nucleic acids. Functionally-equivalent variants according to the invention also include analogues in different parasite genera or species.

Aminopeptidase enzymes are believed to function as part of the nutrient assimilation process of helminths and blockage of enzymic activity may contribute to the protective effect of the antibodies induced in response to immunisation with the antigens of the invention. Aminopeptidase-like activity may be assayed using a range of substrates, for example alanine, leucine and α-glutamyl-p-nitroanilide.

Antigens of the invention have been shown to possess a range of aminopeptidase activities, most notably aminopeptidase M(ApM)-like and aminopeptidase A (ApA)-like activity, which may be demonstrated using e.g. alanine, leucine or methionine p-nitroanilide and α-glutamic acid p-nitroanilide respectively, for example in helminth extracts or on substrate-gels following polyacrylamide-gel electophoresis (PAGE) using corresponding β-methoxy naphthylamide substrates. In addition, inhibitor studies have shown the antigens to be metalloproteinases.

The aminopeptidase antigens of the invention are integral membrane proteins, as may be shown by detergent solubilization studies. For example, the antigens are insoluble in aqueous buffers, such as phosphate-buffered saline (PBS) and detergents such as polyoxyethylene-sorbitan-monolaurate (Tween) which solubilise membrane-associated proteins, but may be solubilised by non-ionic detergents, e.g. TRITON X-100, or dodecylpolyethylene glycolether (THESIT, from Desitin Werk, Hamburg, Germany) which solubilise integral membrane proteins.

Histochemical studies have shown the antigens of the invention to be associated with the intestinal microvilli of the parasites. Thus, for example in the non-obligate blood feeding helminths e.g. Ostertagia and Cooperia, staining of frozen sections reveals the presence of aminopeptidase activity in the area of the intestinal microvilli.

Lectin binding studies have further shown that the antigens of the invention bind to concanavalin A (ConA), indicating the presence of glycosylation, particularly mannose and/or fucose residues.

Preferred antigens according to the invention are those isolatable from Ostertagia. In particular, in both O.circumcincta and O.ostertagia aminopeptidase activity (including ApA- and ApM-like) has been shown to be associated with a band of material which may be separated by electrophoresis on polyacrylamide gel under denaturing conditions, and which has an apparent molecular weight (Mr) of about 124,000–126,000 (6–16% SDS-PAGE). Such proteins and their analogues in other non-blood feeders represent particularly preferred embodiments of the invention.

Antigens according to the invention may be obtained by extraction of non-obligate blood feeding helminth parasites using appropriate detergents.

A further aspect of the invention thus provides a method for preparing the above-mentioned antigens of the invention which comprises the step of subjecting a crude extract of a non-obligate blood feeding helminth parasite to detergent extraction, eg. using Tween 20 or a like detergent to remove membrane-associated proteins followed by Thesit or a like detergent, and recovering the solubilised integral membrane proteins.

The detergent extract may then be subjected to further purification using conventional procedures eg. centrifugation, selective precipitation, electrophoresis, chromatography and the like. Fractions containing the antigen of the invention may be identified by assaying for aminopeptidase activity using known techniques.

The antigen may be released from the membrane in a truncated form, which is soluble in water without addition of detergent, by treatment with a proteolytic enzyme such as trypsin.

Antigens obtainable by such methods form a further aspect of the invention.

The crude extract of the helminth parasite may be prepared using conventional biochemical and surgical techniques eg. by homogenisation of the whole or a portion of the parasite. Thus, for example the parasites may be subjected to homogenisation in a suitable buffer or medium such as phosphate buffered saline (PBS), and the insoluble material (ie. the pellet) may be recovered by centrifugation, whereby to form the required crude extract.

Thus, a suitable purification protocol for the antigens of the invention might comprise (i) homogenising adult parasite worms in PBS, recovering the PBS-insoluble material (eg. by centrifugation), optionally repeating the PBS-washing step one or more times, (ii) extracting the PBS-insoluble material (ie. the pellet) with aqueous Tween 20 (eg. in PBS), (iii) recovering the Tween-insoluble fraction e.g. by centrifugation, (iv) extracting the Tween-insoluble material with aqueous Thesit (e.g. in PBS), (v) recovering the solubilised fraction containing the Thesit-soluble proteins, (ie. the supernatent also known as ThHS) followed by (vi) ion exchange chromatography eg. on a Mono Q column, and/or gel filtration eg. using Superose. A ConA affinity chromatography step may optionally also be included e.g. before ion exchange.

An alternative preparation process may take advantage of the fact that the target antigens have particular selective binding activities by using an affinity chromatography system in which specific ligands are immobilised on a solid phase matrix.

Thus the invention also provides a process for preparing the above-mentioned antigens of the invention, said process comprising preparing an extract of said parasite containing at least one protective antigen as defined above, purifying said antigen therefrom by binding said antigen to an immobilized phase including a specific binding partner for the antigen and subsequently eluting said antigen from said immobilized phase. Suitable specific binding partners include substrate analogues, for example the inhibitor bestatin, and oligosaccharide specific lectins e.g. ConA.

The invention also provides use of a helminth parasite antigen as hereinbefore defined, and fragments, precursors and functionally-equivalent variants thereof, for the preparation of a vaccine composition for use in stimulating an immune response against helminth parasites in a human or non-human, animal.

Further provided according to the invention is a vaccine composition for stimulating an immune response against helminth parasites in a human or non-human animal comprising one or more antigens, antigenic fragments, precursors or functionally-equivalent variants thereof, as defined above, together with a pharmaceutically acceptable carrier or diluent, and a method of stimulating an immune response against helminth parasites in a human or non-human animal, comprising administering to said animal a vaccine composition as defined above.

The animal preferably is mammalian and more preferably a ruminant.

As mentioned above, antigens according to the invention may be obtained from a range of non-obligate blood feeding helminth parasite genera. Preferably, however the helminths will be nematodes, especially preferably gastro-intestinal nematodes including for example Ostertagia and Cooperia. As mentioned above, antigens from Ostertagia are especially preferred. Such antigens may be used to prepare vaccines against a range of helminth parasites including any of those mentioned above. Preferred are those antigens, so called "broad spectrum" antigens, which are capable of stimulating host protective immune responses against, in addition to the parasite from which they were isolated, a broad range of other parasites.

As mentioned above, one of the ways in which the antigens of the invention may exert their host protective effects is by raising inhibitory antibodies which inhibit the growth, maintenance and/or development of the parasite. Such antibodies and their antigen-binding fragments (eg. $F(ab)_2$, Fab and Fv fragments ie. fragments of the "variable" region of the antibody, which comprises the antigen binding site) which may be mono- or polyclonal, form a further aspect of the invention, as do vaccine compositions containing them and their use in the preparation of vaccine compositions for use in passively immunising hosts against parasites. Such inhibitory antibodies may be raised by use of idiotypic antibodies. Anti-idiotypic antibodies may be used as immunogens in vaccines.

In addition to the extraction and isolation techniques mentioned above, the antigens may be prepared by recombinant DNA technology using standard techniques, such as those described for example by Sambrook et al., 1989, (Molecular Cloning, a laboratory manual 2nd Edition, Cold Spring Harbor Press).

Nucleic acid molecules comprising a nucleotide sequence encoding the antigens of the invention thus form further aspects of the invention.

Nucleic acid molecules according to the invention may be single or double stranded DNA, cDNA or RNA, preferably DNA, and include degenerate, substantially homologous and hybridising sequences which are capable of coding for the antigen or antigen fragment or precursor concerned.

By "substantially homologous" is meant sequences displaying at least 60%, preferably at least 70% or 80% sequence homology. Hybridising sequences included within the scope of the invention are those binding under non-stringent conditions (6×SSC/50% formamide at room temperature) and washed under conditions of low stringency (2×SSC, room temperature, more preferably 2×SCC, 42° C.) or conditions of higher stringency eg. 2×SSC, 65° C. (where SSC=0.15M NaCl, 0.015M sodium citrate, pH 7.2), as well as those which, but for the degeneracy of the code, would hybridise under the above-mentioned conditions.

Derivatives of nucleotide sequences capable of encoding antigenically active antigens or antigen variants according to the invention may be obtained by using conventional methods well known in the art.

Antigens according to the invention may be prepared in recombinant form by expression in a host cell containing a recombinant DNA molecule which comprises a nucleotide sequence as broadly defined above, operatively linked to an expression control sequence, or a recombinant DNA cloning vehicle or vector containing such a recombinant DNA molecule. Synthetic polypeptides expressed in this manner form a further aspect of this invention (the term "polypeptide" is used herein to include both full-length protein and shorter length peptide sequences).

The antigen so expressed may be a fusion polypeptide comprising all or a portion of an antigen according to the invention and an additional polypeptide coded for by the DNA of the recombinant molecule fused thereto. This may for example be β-galactosidase, glutathione-S-transferase, hepatitis core antigen or any of the other polypeptides commonly employed in fusion proteins in the art.

Other aspects of the invention thus include cloning and expression vectors containing the DNA coding for an antigen of the invention and methods for preparing recombinant nucleic acid molecules according to the invention, comprising inserting nucleotide sequences encoding the antigen into vector nucleic acid, eg. vector DNA. Such expression vectors include appropriate control sequences such as for example translational (eg. start and stop codons, ribosomal binding sites) and transcriptional control elements (eg. promoter-operator regions, termination stop sequences) linked in matching reading frame with the nucleic acid molecules of the invention.

Vectors according to the invention may include plasmids and viruses (including both bacteriophage and eukaryotic viruses) according to techniques well known and documented in the art, and may be expressed in a variety of different expression systems, also well known and documented in the art. Suitable viral vectors include baculovirus and also adenovirus and vaccinia viruses. Many other viral vectors are described in the art.

A variety of techniques are known and may be used to introduce such vectors into prokaryotic or eukaryotic cells for expression, or into germ line or somatic cells to form transgenic animals. Suitable transformation or transfection techniques are well described in the literature.

The invention also includes transformed or transfected prokaryotic or eukaryotic host cells, or transgenic organisms containing a nucleic acid molecule according to the invention as defined above. Such host cells may for example include prokaryotic cells such as E.coli, eukaryotic cells such as yeasts or the baculovirus-insect cell system, transformed mammalian cells and transgenic animals and plants. Particular mention may be made of transgenic nematodes (see for example Fire, 1986, EMBO J., 5. 2673 for a discussion of a transgenic system for the nematode Caenorhabditis).

A further aspect of the invention provides a method for preparing an antigen of the invention as hereinbefore defined, which comprises culturing a host cell containing a nucleic acid molecule encoding all or a portion of said antigen, under conditions whereby said antigen is expressed and recovering said antigen thus produced.

The antigens of the invention and functionally equivalent antigen variants may also be prepared by chemical means, such as the well known Merrifield solid phase synthesis procedure.

Water soluble derivatives of the novel antigens discussed above form a further aspect of the invention. Such soluble forms may be obtained by proteolytic digestion, for example using the enzyme trypsin. Generally speaking enzymic digestion of the antigens yields two fractions, a detergent soluble fraction (which remains with the membrane) and a water-soluble fraction.

A vaccine composition may be prepared according to the invention by methods well known in the art of vaccine manufacture. Traditional vaccine formulations may comprise one or more antigens or antibodies according to the invention together, where appropriate, with one or more suitable adjuvants eg. aluminium hydroxide, saponin, quil A, or more purified forms thereof, muramyl dipeptide, mineral or vegetable oils, Novasomes or non-ionic block co-polymers or DEAE dextran, in the presence of one or more pharmaceutically acceptable carriers or diluents. Suitable carriers include liquid media such as saline solution appropriate for use as vehicles to introduce the peptides or polypeptides into an animal or patient. Additional components such as preservatives may be included.

An alternative vaccine formulation may comprise a virus or host cell eg. a microorganism (eg. vaccinia virus, adenovirus, bacteria such as the Bacillus Calmette-Guérin strain of *Mycobacterium bovis* (BCG) or Salmonella spp) which may be live, killed or attenuated, having inserted therein a nucleic acid molecule (eg. a DNA molecule) according to this invention for stimulation of an immune response directed against polypeptides encoded by the inserted nucleic acid molecule.

Administration of the vaccine composition may take place by any of the conventional routes, eg. orally or parenterally such as by intramuscular injection, optionally at intervals eg. two injections at a 7–35 day interval.

The antigens may be used according to the invention in combination with other protective antigens obtained from the same or different parasite species. Such a combined vaccine composition may contain smaller amounts of the various antigens than an individual vaccine preparation, containing just the antigen in question. Combined vaccines are beneficial where there is a likelihood that "adaptive selection" of the parasite may occur when a single antigen vaccine is used.

Animals which may benefit from the present invention may be any human or non-human animal, but companion animals, particularly dogs and cats and domestic animals, especially ruminants are preferred. Particular mention may be made of sheep, cattle, pigs, deer and goats.

Treatment of membrane preparations obtained from *O. ostertagi* with trypsin released aminopeptidase M activity in a water-soluble form which bound to ConA and after gel filtration yielded a fraction with high activity and showing a Coomassie blue staining band on SDS-PAGE around 116, 000. The N-terminal sequence of a band of similar size obtained by SDS-PAGE of a breakdown product of O12 was Ala Glu Asp Leu Arg Leu Pro Thr Asn Ile Arg Pro Leu Ile Tyr Asp Leu Thr (AEDLRLPTNIRPLIYDLT, SEQ ID NO:1). This shows 67% identity and 89% similarity to the sequence of the corresponding region of microsomal aminopeptidases H110D-1, -2 and -3 from *Haemonchus contortus* deduced from their DNA sequences and 67% identity to the observed N-terminal amino acid sequence of a water soluble fragment released from H110D by trypsin cleavage. The amino acids Leu, Pro, Pro and Tyr at positions 6, 7, 12 and 15 respectively of this peptide are conserved in human, pig, rat and mouse microsomal aminopeptidases.

The full sequence of the O12 microsomal aminopeptidase was obtained by sequencing cloned PCR products generated from *Ostertagia ostertagi* first strand cDNA and primers based on a) the sequence GAMENWGL (SEQ ID NO: 2) common to the H110D microsomal aminopeptidases, b) at the 5' end, the helminth spliced leader sequence SL1 and c) a vector sequence at the 3' end.

Antibodies to O12 do not form in the course of infection but the protein is shown to be highly immunogenic in sheep and cattle when injected in purified form. Antibodies raised against O12 from *O. ostertagi* cross-react with periodate-treated O12 from *O. circumcincta* as do antibodies raised in sheep to CamQH110D.

This invention will now be described in more detail with particular reference to the protein O12 from *Ostertagia ostertagi*. However, by a variety of techniques such as histochemistry and Western blotting, O12 equivalents have been demonstrated in the parasites *Ostertagia circumcincta* and *Cooperia oncophora*. It is believed that the O12 protein is a multigene complex and that in addition, the nucleotide sequences encoding it, may exhibit sequence variations between different strains and different life cycle stages of the helminth. Moreover there may exist multiple enzyme forms (isoenzymes) which may be differentially expressed at different stages, or in different strains. In this study DNA sequences, and thus the predicted amino acid sequences, have been determined from cDNA clones and PCR products obtained from mRNA corresponding to the O12 gene by recombinant DNA technology from 12-days old (early fifth stage) *Ostertagia ostertagi*.

Sequencing of PCR products has enabled us to identify closely related O12 sequences which are here designated O12-1 (SEQ ID NO:19), O12-2 (SEQ ID NO:20), O12-3 (SEQ ID NO:21), O12-4 (SEQ ID NO:22) and O12-5 (SEQ ID NO:23). O12-1 and O12-2 are 5' sequences of about 1 kb terminating at their 3' ends in the primer based on the conserved sequence GAMENWGL (SEQ ID NO:2); O12-3, O12-4 and O12-5are 3' sequences of about 2.5 kb originating at their 5' ends with this primer.

The relationships of O12-1 and -2 with O12-3, -4 and -5 may be determined by PCRing between primers towards the 3' ends of O12-1 and -2 and the 5' ends of O12-3, -4 and -5 to include the common GAMENWGL (SEQ ID NO:2) sequence.

Differences and variations in the sequences obtained from the PCR products have been observed, as can be seen in particular from FIGS. 19 and 20 (SEQ ID NO:23) and as summarised below.

Homologies of the deduced amino acid sequences (SEQ ID NO:24–28) obtained by translation of the nucleotide sequences shown in FIGS. 19 and 20 (SEQ ID NO:19–23).

|  | % Similarity | % Identity |
|---|---|---|
| O12-1: O12-2 | 86.1 | 76.3 |
| O12-3: O12-4 | 77.3 | 77.3 |

-continued

| | % Similarity | % Identity |
|---|---|---|
| O12-3: O12-5 | 95.6 | 95.5 |
| O12-4: O12-5 | 76.8 | 76.8 |

The differences can be attributed to different mRNAs multigene family.

Comparison of the sequences of various of the clones mentioned above, against computer databases of known sequences, reveals substantial homology with the family of microsomal aminopeptidase enzymes (EC. 3.4.11.-). Enzymological activity and inhibitor studies performed with the O12 protein and subfractions thereof confirm that the protein is in fact microsomal aminopeptidase (α-amino acyl peptide hydrolase (microsomal)). Using the enzyme trypsin, it was found that O12 may be partially cleaved, forming two fractions, a detergent-soluble fraction (which remained with the membrane) and a water-soluble fraction (which is designated O12S); it was found that aminopeptidase M-like activity is associated with the water-soluble O12S fraction.

An eighteen amino acid N-terminal sequence (designated Pep A, SEQ ID NO:1) from a proteolytic fragment of O12 has 67% identity and 89% similarity to the corresponding fragments of H110D-1, -2 and -3 deduced from their DNA sequences. The sequences are PepA: AEDLRLPTNIRPLIYDLT (SEQ ID NO:1)
H11-1: AEELRLPTTIKPLTYDLV (SEQ ID NO:29)
PepA: AEDLRLPTNIRPLIYDLT (SEQ ID NO:1)
H11-2: AEELLLPTNIKPVSYDLN (SEQ ID NO:30)
PepA: AEDLRLPTNIRPLIYDLT (SEQ ID NO:15)
H11-3: AAELLLPSNIKPLSYDLT (SEQ ID NO:16)

Over this region the three deduced H11 sequences are 72–77% identical (13 or 14 amino acids) and 83–100% similar.) Nine amino acids are conserved in all four sequences:

A12L3LP45I6P7XYDLX

For the other residues, 1 is either E or A, 2 is D in PepA and E in H11, 3 is L or R, 5 is N or T, 6 is R in PepA and K in E11, and 7 is L or V (LP P Y are conserved in human, pig, rat and mouse microsomal aminopeptidases.)

Comparing the amino acid sequences of PepA (SEQ ID NO:1) and H110D (H11) as determined we have:

PepA ARDLRLPTNIRPLIYDLT (SEQ ID NO:1)
(N-terminus of a breakdown product.)
H11 AEELLLPTNIKPVSYDLK (SEQ ID NO:32)
(N-terminus of a trypsin fragment.) this has 67% identity and 83% similarity.

PCR from *O. ostertagi* first strand cDNA using an oligonucleotide corresponding to the H110D conserved sequence GAMENWGL (SEQ ID NO:2) has yielded products of the expected sizes, about 1 kb with the 5' primer and about 2.5 kb with the 3' primer. Two closely related but distinguishable 5' sequences designated O12-1 and O12-2 have been obtained (see FIG. 19, SEQ ID NOS: 19 AND 20). Over the region above, the deduced sequences for O12-1 and O12-2 are 72% identical.

O12-1 AEELRLPSVIPPLLYDLS (SEQ ID NO:41)
O12-2 AEBLRLPTNIKPLLYNLT (SEQ ID NO:42)
PepA AEDLRLPTNIRPLIYDLT (SEQ ID NO:1)
O12-1 AEELRLPSVIPPLLYDLS (SEQ ID NO:41)

There is 72% identity of the determined amino acid sequence of PepA (SEQ ID NO:1) with the sequence deduced from clone O12-1 and 67% identity with the sequence from clone O12-2.

The invention will now be described further in the following non-limiting Examples in which:

FIG. 1 Shows light micrographs of frozen sections of parasitic nematodes stained for microsomal aminopeptidase activities. The activity is revealed by the deposition of reddish blue reaction product seen as a dark band (arrowed) in these black and white photographs; (a) *O.ostertagi*, ApM-like activity (b) *O.circumcincta* ApM-like activity; (c) *O.ostertagi*, ApA-like activity (d) *O.circumcincta*, ApA-like activity.

Figure 3:
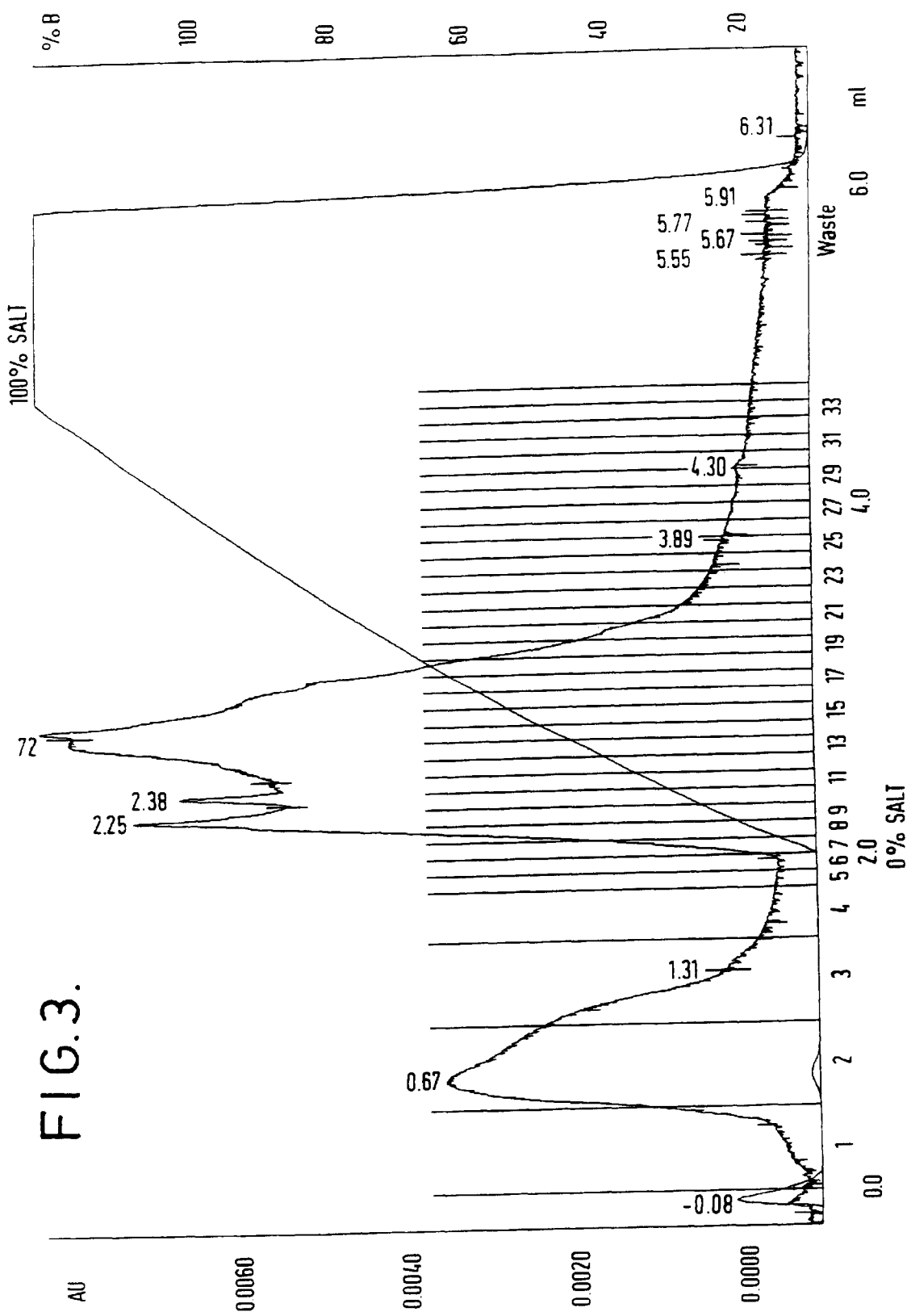
FIG. 3 Shows fractionation of integral membrane proteins from *Ostertagia ostertagi* ThHS by chromatography on an anion exchange column (Compare FIG. 4.); protein absorbance 280 nm, elution 0–100% salt gradient.
Figure 4:
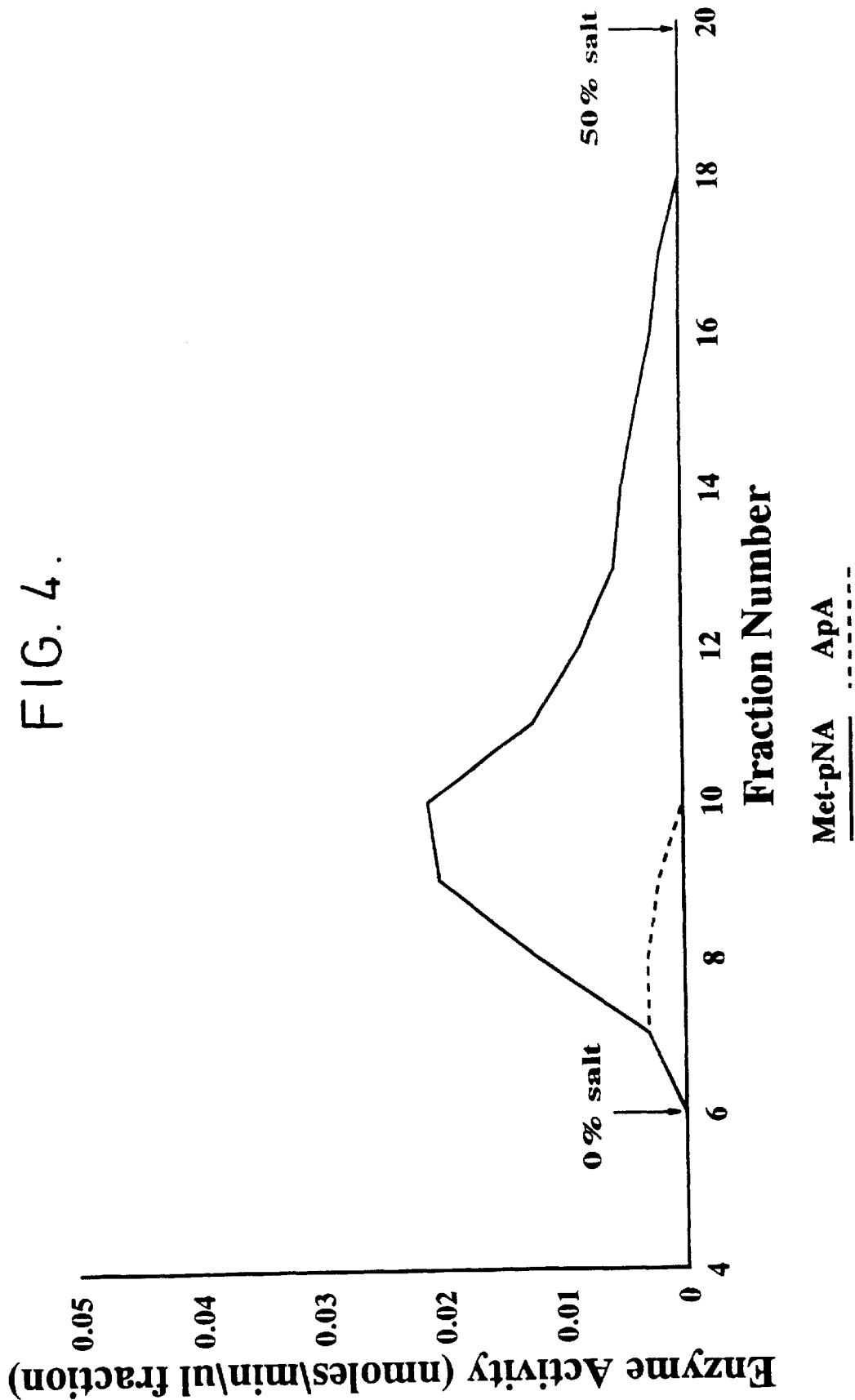

FIG. 4 Shows the distribution of enzyme activities in fractions from anion exchange chromatography shown in FIG. 3. Met-pNA, aminopeptidase M-like activity; ApA, aminopeptidase A-like activity.

Figure 5:
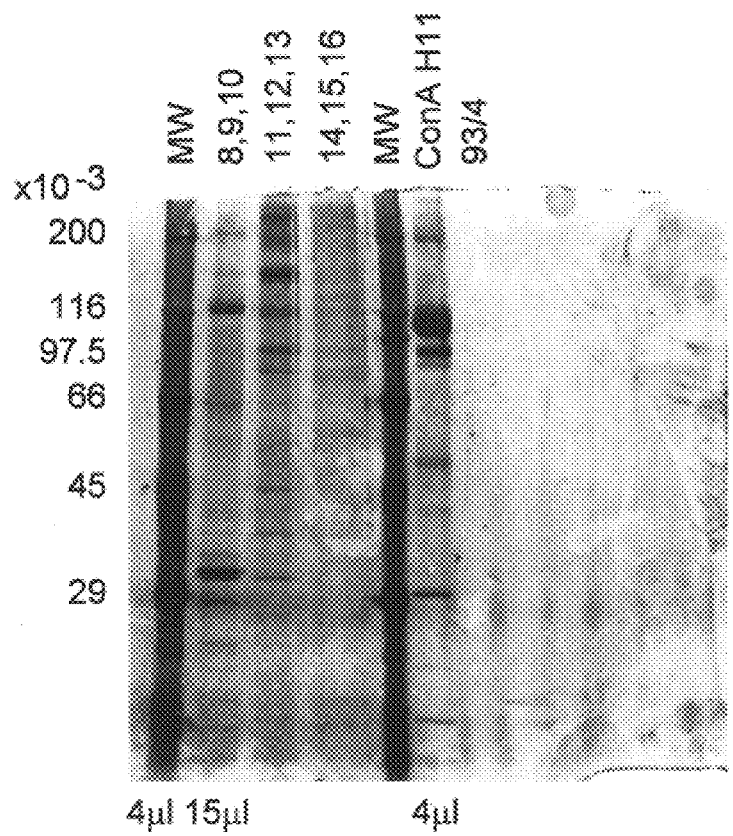

FIG. 5 Shows 6–16% SDS-PAGE under reducing conditions of pooled fractions from anion exchange chromatography shown in FIGS. 3 and 4. i), v), molecular weight markers; ii) Fractions 8, 9 and 10; iii) Fractions 11, 12 and 13; iv) Fractions 14, 15 and 16; vi) an H110D-enriched preparation for comparison. Oo12 is arrowed in track ii).

Figure 6:
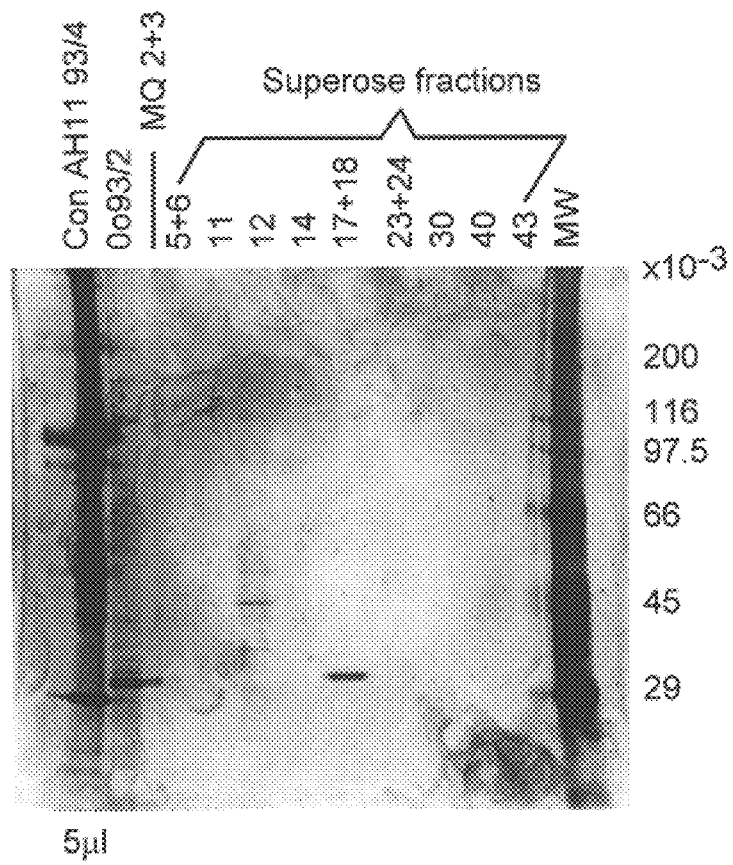

FIG. 6 Shows 6–16% SDS-PAGE under reducing conditions of pooled fractions from anion exchange column likely to contain aminopeptidase activity and further fractioned by gel exclusion using superose 12 (mw exclusion of $2 \times 10^6$). Aminopeptidase activity was only present in Fraction 12, the only fraction with a band at 125,000 (arrowed). Molecular weight markers and an H110D-enriched fraction were also run for comparison.

Figure 7:
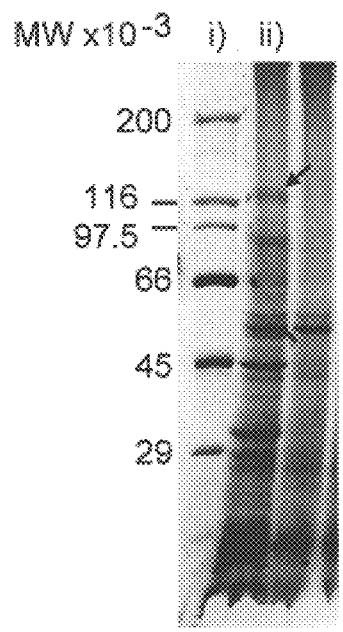
Figure 8A:
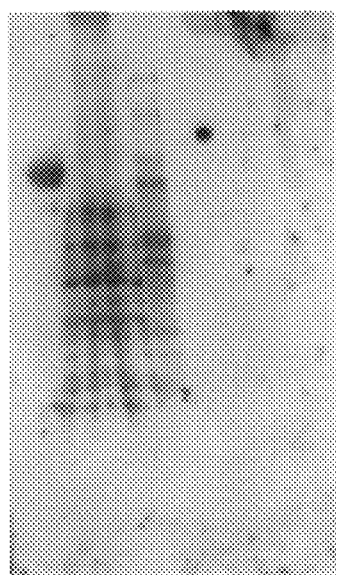
Figure 8B:
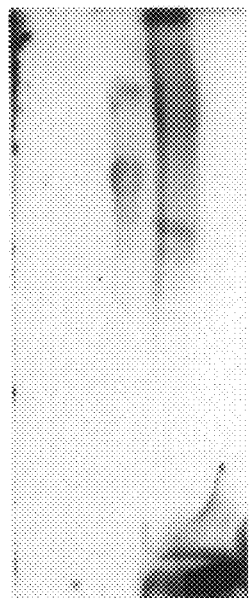
Figure 8C:
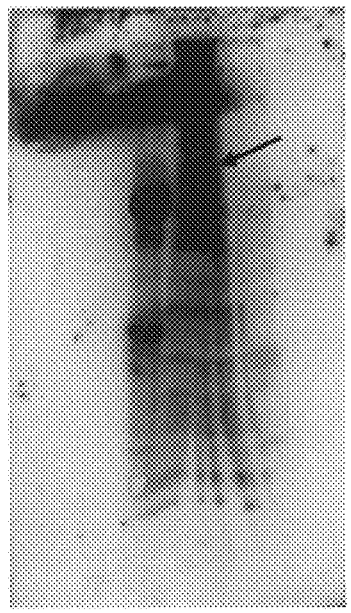
Figure 8D:
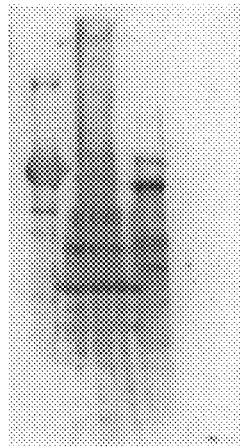

FIG. 7 Shows 6–16% SDS-PAGE under reducing conditions of integral membrane proteins from *Ostertagia circumcincta*. Track i) molecular weight markers; ii) proteins soluble in Thesit after pre-extraction with PBS and Tween 20, the band with $M_r$ 124,000 (Oc12) is arrowed.

FIG. 8 Shows western blots treated with biotinylated lectins a) *Ulex europaeus;* b) *Triticum vulgaris;* c) Concanavalin A; d) *Dolichos bifluorus;* of i) H110D-enriched preparation compared with; ii) OcThHS and iii) molecular weight markers. The arrow on (c) indicates Oc12.

Figure 9:
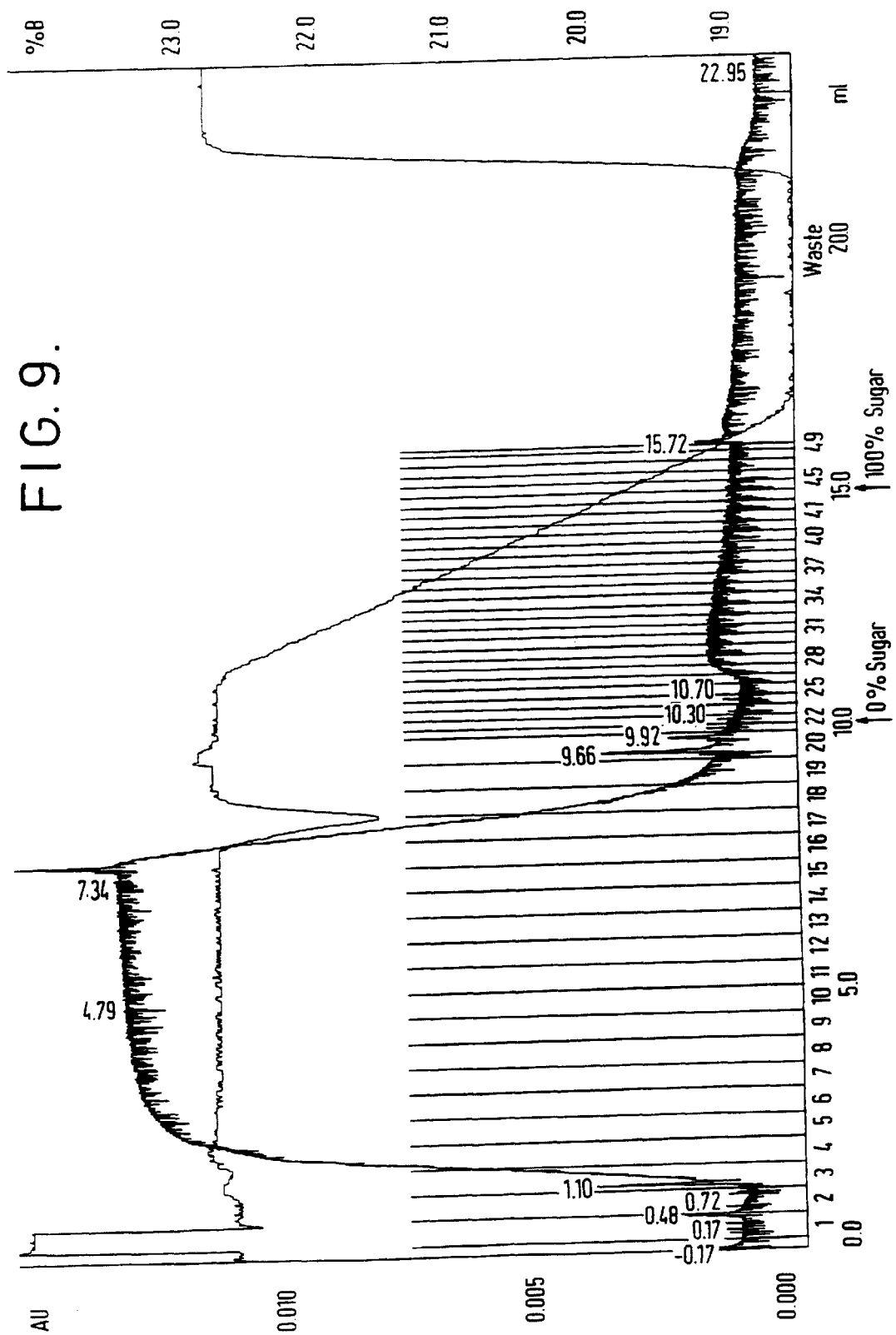

FIG. 9 Shows fractionation of OcThHS initially passed through an *Ulex europaeus* lectin column to remove low molecular weight contaminants, by affinity chromatography on a Con A column. Protein absorbance 280 nm, Elution 0 to 100% 0.5M sugar (α-methylglucopyranoside) gradient.

Figure 10:
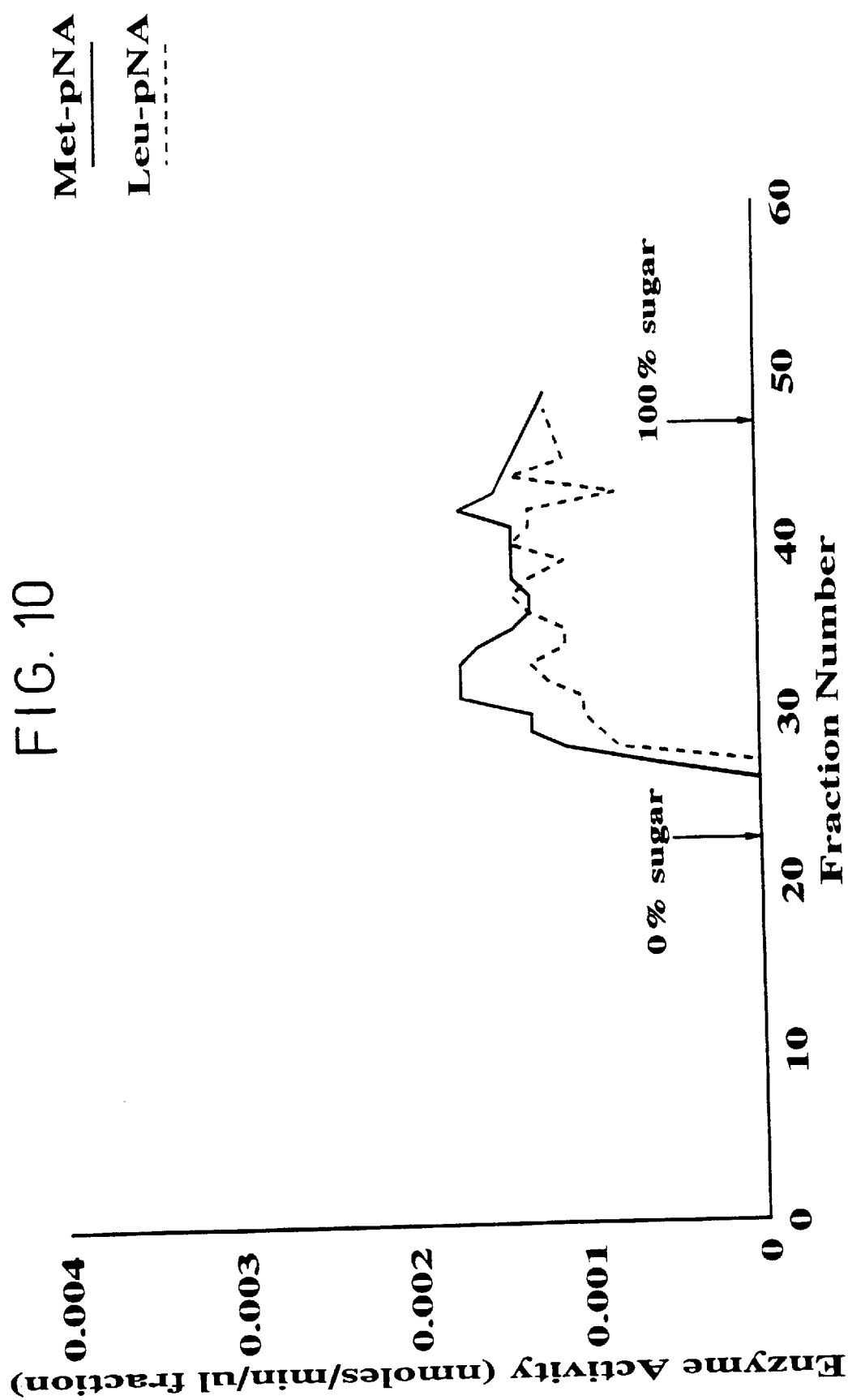

FIG. 10 Shows distribution of enzyme activities in fractions of OcThHS obtained from the Con A column chromatography shown in FIG. 9. Met-pNA, Leu-pNA, aminopeptidase M-like activities.

Figure 11:
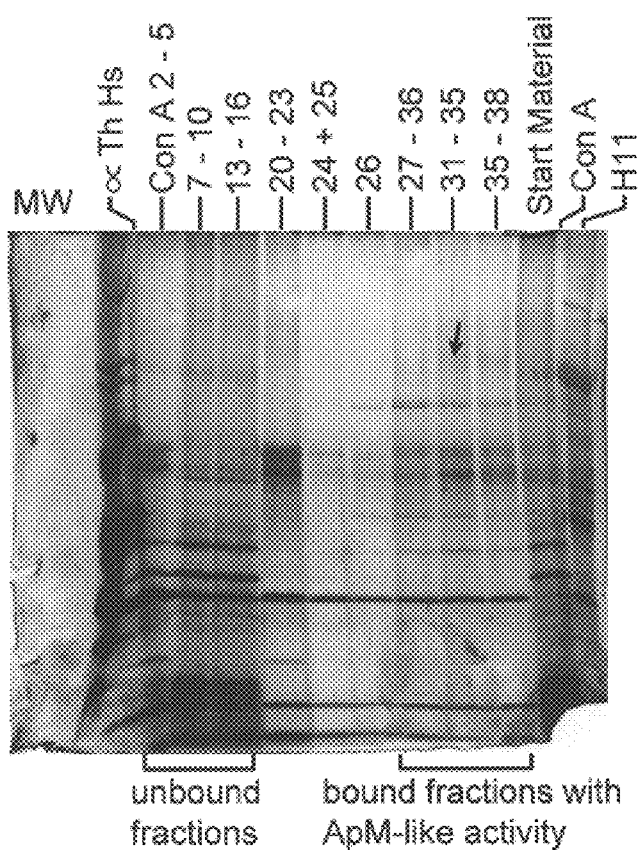

FIG. 11 Shows 6–16% SDS-PAGE under reducing conditions of fractions from Con A affinity chromatography, initially passed through a *Ulex europaeus* column. Only the binding fractions with aminopeptidase M-like activity contained a band of Mr 124,600 (arrowed).

Figure 12:
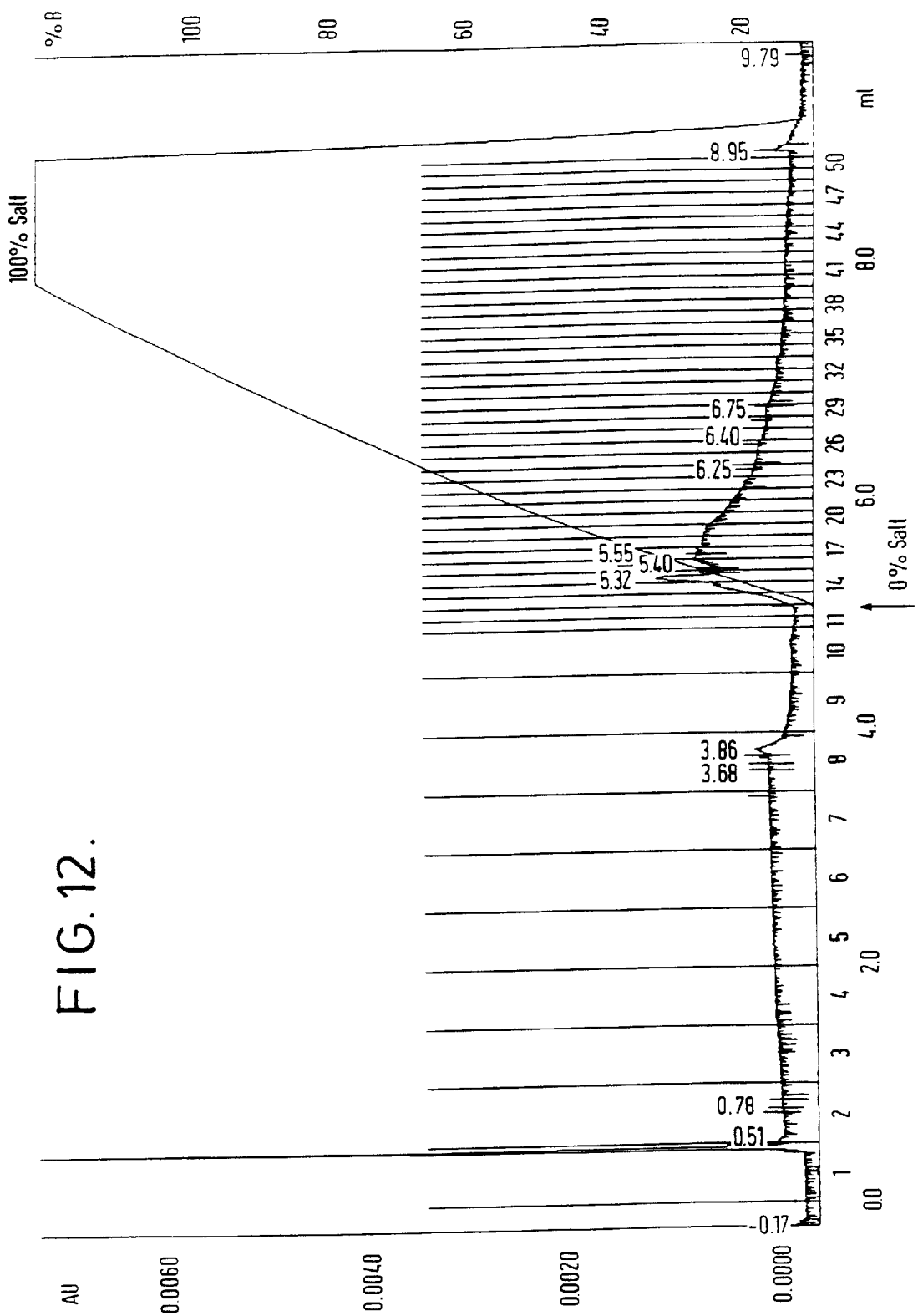

FIG. 12 Shows ion exchange chromatography of pooled fractions from Con A chromatography that bound to the column and which contained aminopeptidase activity; Protein absorbance at 280 nm, salt gradient from 0 to 100%.

Figure 13:
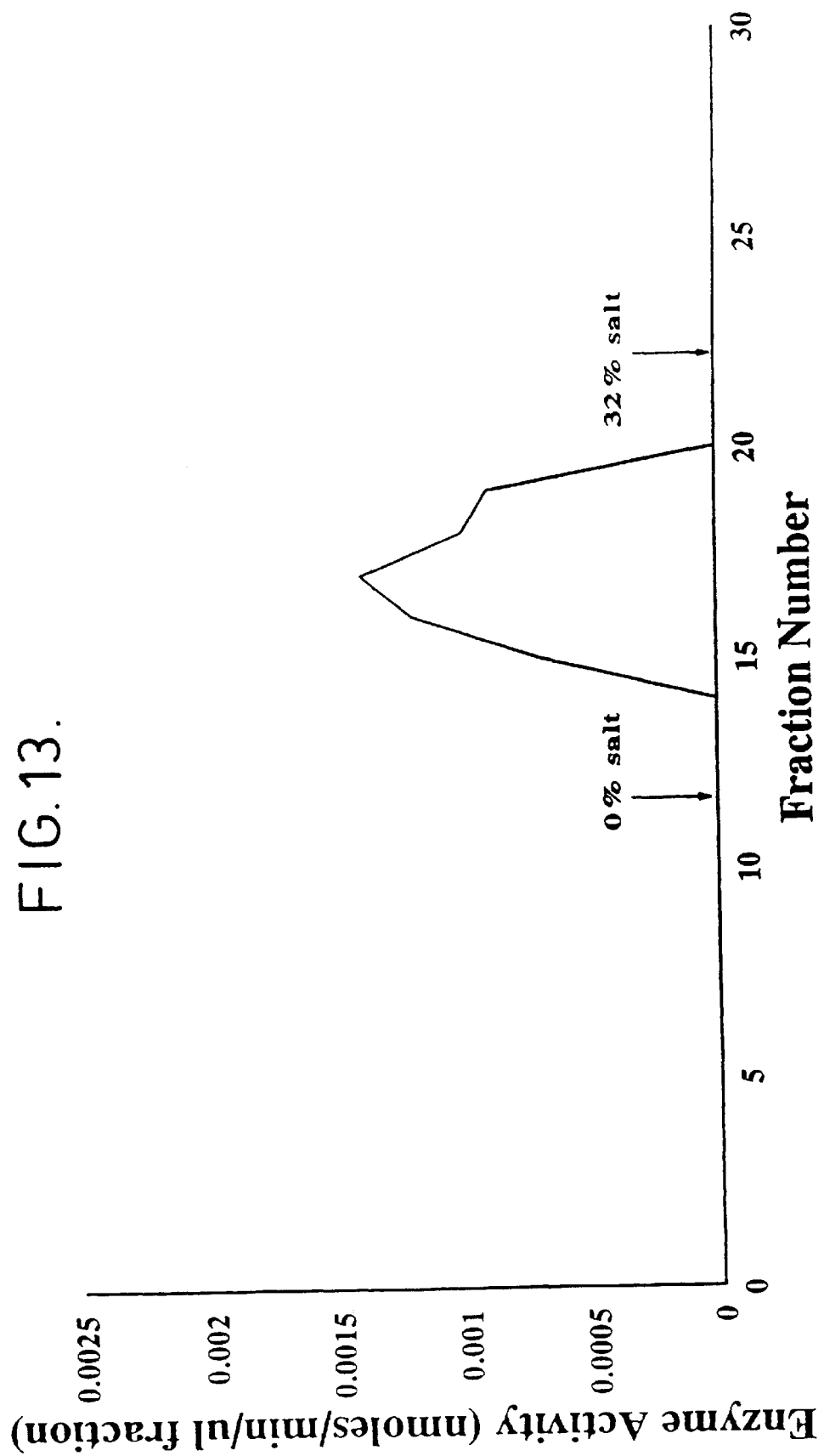

FIG. 13 Shows the distribution of aminopeptidase M-like (Met-pNA) activity in fractions obtained by anion exchange chromatography.

Figure 14:
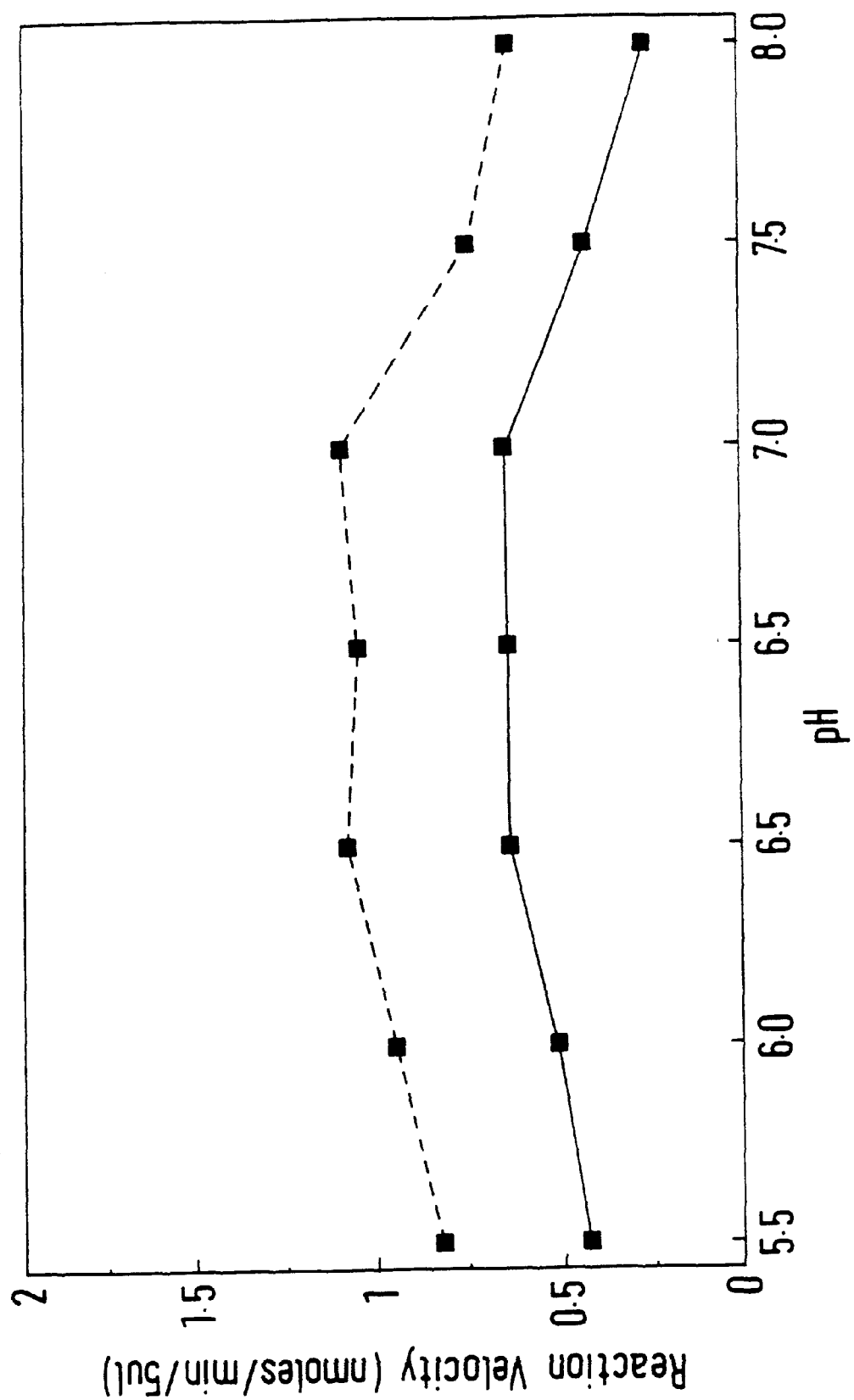

FIG. 14 Shows pH profiles of the aminopeptidase activity of Oo12 compared to H11 with leucine p-nitroanilide as substrate. The solid and dashed lines indicate the results obtained for O12 and H11, respectively. In the assays, MES and MOPS were used to cover the pH ranges 5.5 to 6.5 and 6.5 to 8.0, respectively. Aminopeptidase activity was assayed using 5 μl O12 in PBS/0.1% thesit at a concentration of 0.378 mg/ml and 5 μl H11 in ConA Buffer B at a concentration of 1.25 mg/ml, and assayed over 21 minutes.

Figure 15:
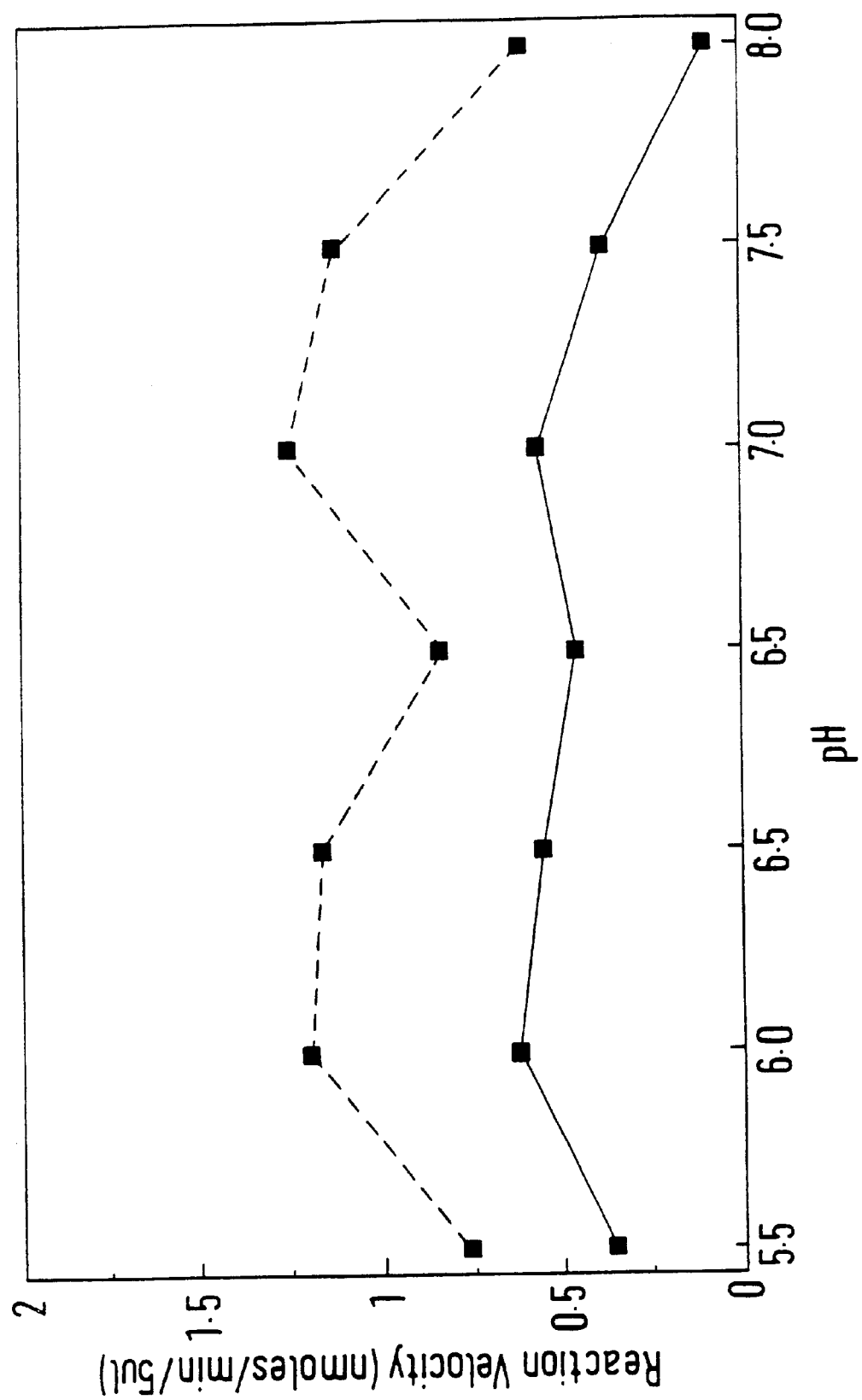

FIG. 15 Shows pH profiles of the aminopeptidase activity of Oo12 compared to H11 with methionine p-nitroanilide as substrate. The solid and dashed lines indicate the results obtained for O12 and H11, respectively. The assays were performed as described in the legend to FIG. 14 over a period of 13.6 minutes.

Figure 16:
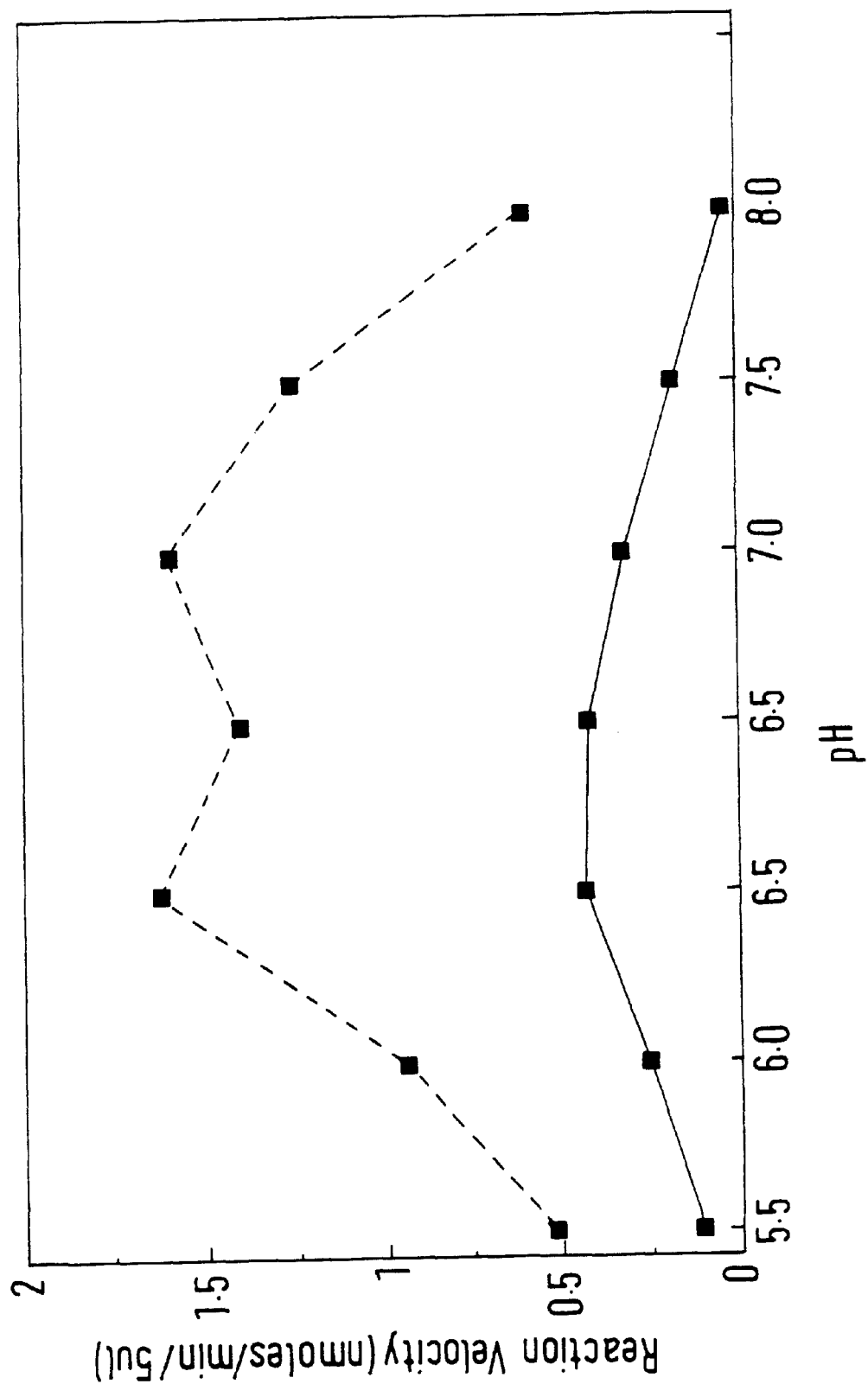

FIG. 16 Shows pH profiles of the aminopeptidase activity of Oo12 compared to H11 with α-glutamic p-nitroanilide as substrate. The solid and dashed lines indicate the results obtained for O12 and H11, respectively. The assays were performed as described in the legend to FIG. 14 using 5 μl O12 in ConA Buffer A at a concentration of 0.529 mg/ml and 5 μl H11 in ConA Buffer B at a concentration of 2.5 mg/ml over a period of 25 minutes.

Figure 17:
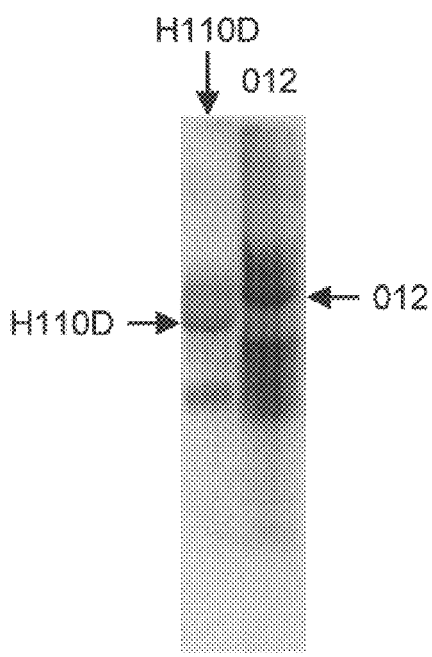

FIG. 17 Shows a sodium periodate treated Western blot of ConA Oo12 and ConA H11 probed with sheep α-Oo12E serum.

Figure 18:
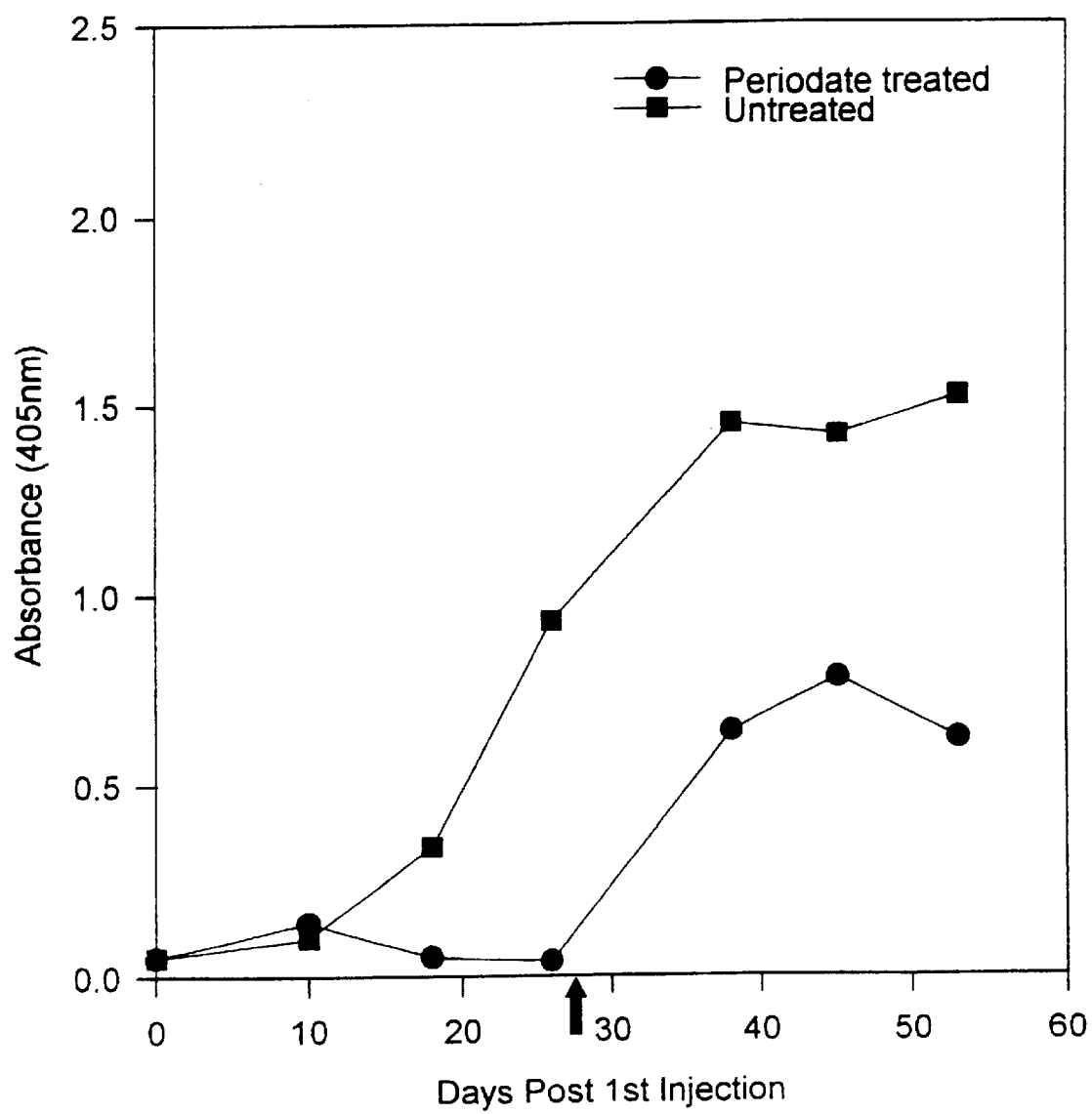

FIG. 18 Shows the recognition of Oo12E by serum from sheep injected with Oo12E, as measured by ELISA. The antiserum titre increased with time after antigen injection illustrating the antigenicity of Oo12. Antiserum titres against periodate treated antigen were lower than against untreated antigen. The arrow indicates the time of the second injection.

FIG. 19 Shows the nucleotide sequences of 19 a) O12-1 (SEQ ID NO:19) and 19 b) O12-2 (SEQ ID NO:20) derived from cloned PCr products.

FIG. 20 Shows the nucleotide sequences of 20 a) O12-3 (SEQ ID NO:21), 20 b) O12-4 (SEQ ID NO:22), and 20 c) O12-5 (SEQ ID No:23) derived from cloned PCR products.

Figure 21B:
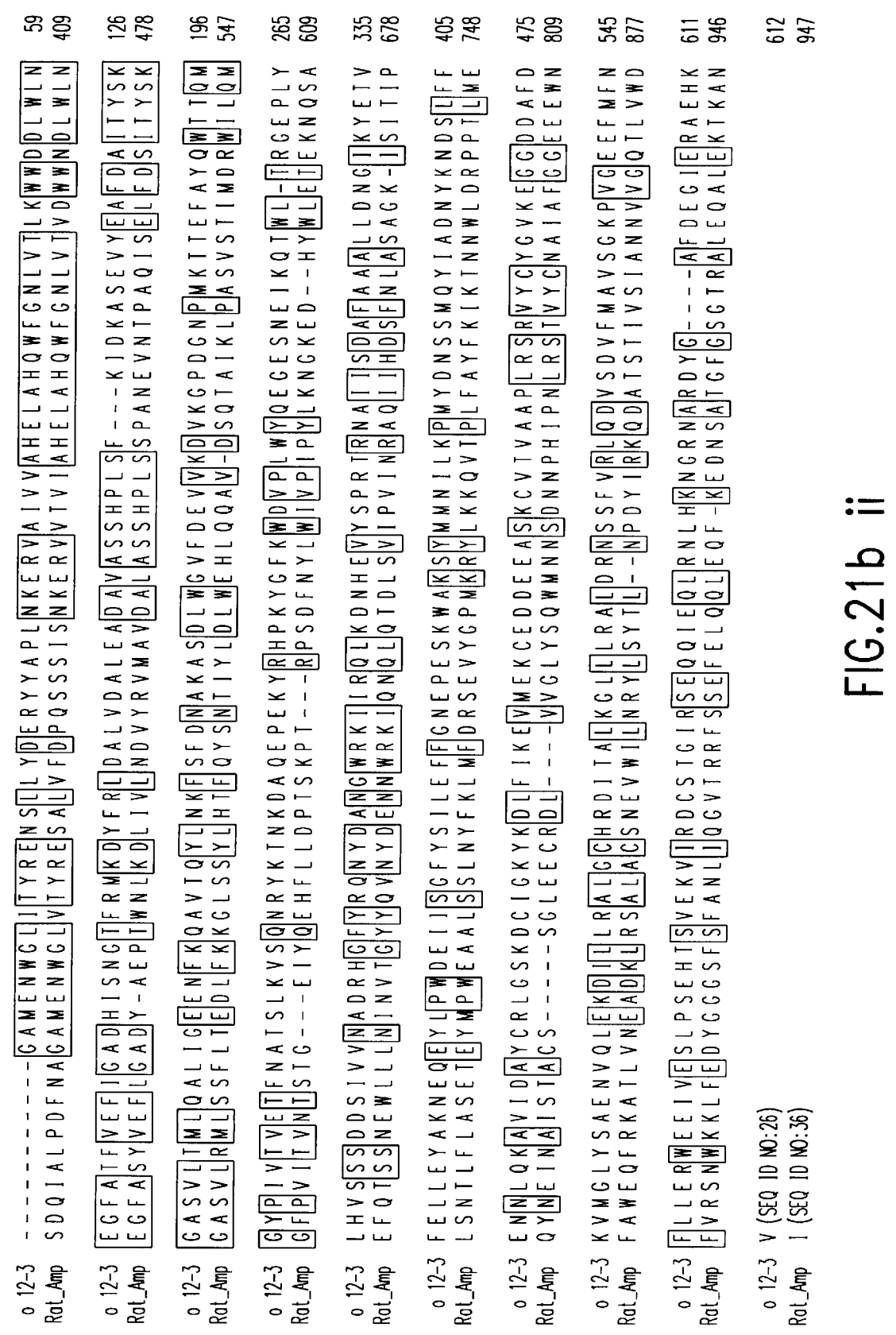
Figure 21B:
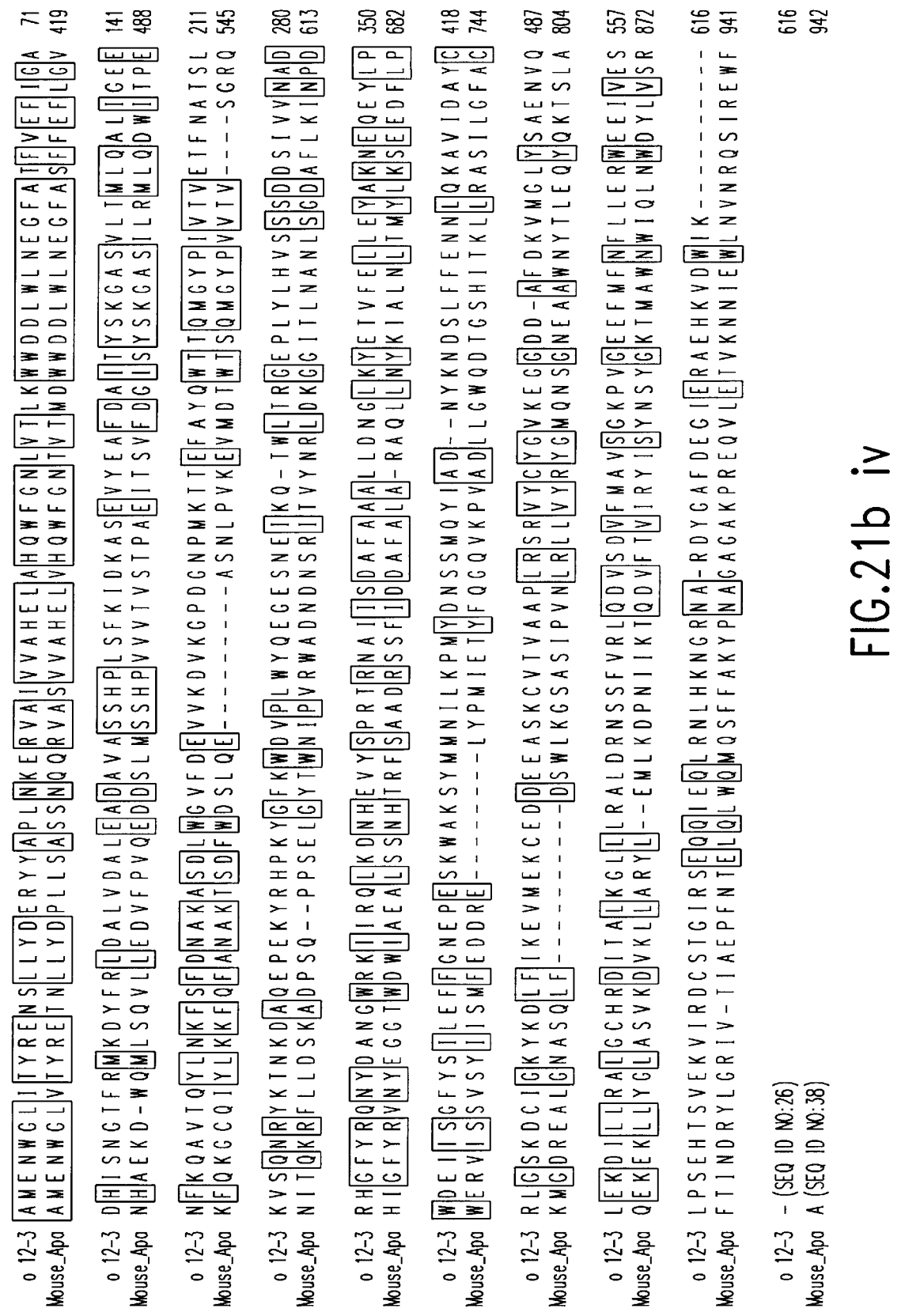

FIGS. 21 a(i)–a(v) (SEQ ID NOS:24–28) show the predicted amino acid sequences derived from the DNA sequences O12-1, O12-2, O12-3, O12-4 and O12-5, respectively, shown in FIGS. 19 and 20 (SEQ ID NOS:19–23);

b(i)–b(vi) show the predicted amino acid sequences of O12-1 and O12-3 compared with the published amino acid sequences of (i) and (ii) rat microsomal aminopeptidase M (Watt et al., 1989), (iii) and (iv) mouse microsomal aminopeptidase A (Wu et al., 1990) and (v) and (vi) Haemonchus H11-3 respectively; identities are enclosed in boxes, dashes indicate spaces introduced to maximise the level of homology between the compared sequences. The conventional single letter code for amino acids is used. The horizontal line above the sequence indicates the position of the transmembrane region and the asterisks show the position of the zinc-binding motif.

FIG. 22 Shows the alignments of the amino acid sequence (designated PepA, SEQ ID NO:1) with partial predicted amino acid sequences (SEQ I.D. NO:41) derived from O12-1 (SEQ ID NO:19), and (SEQ ID NO. 42) derived from O12-2 (SEQ. I.D. NO:20).

Figure 23:
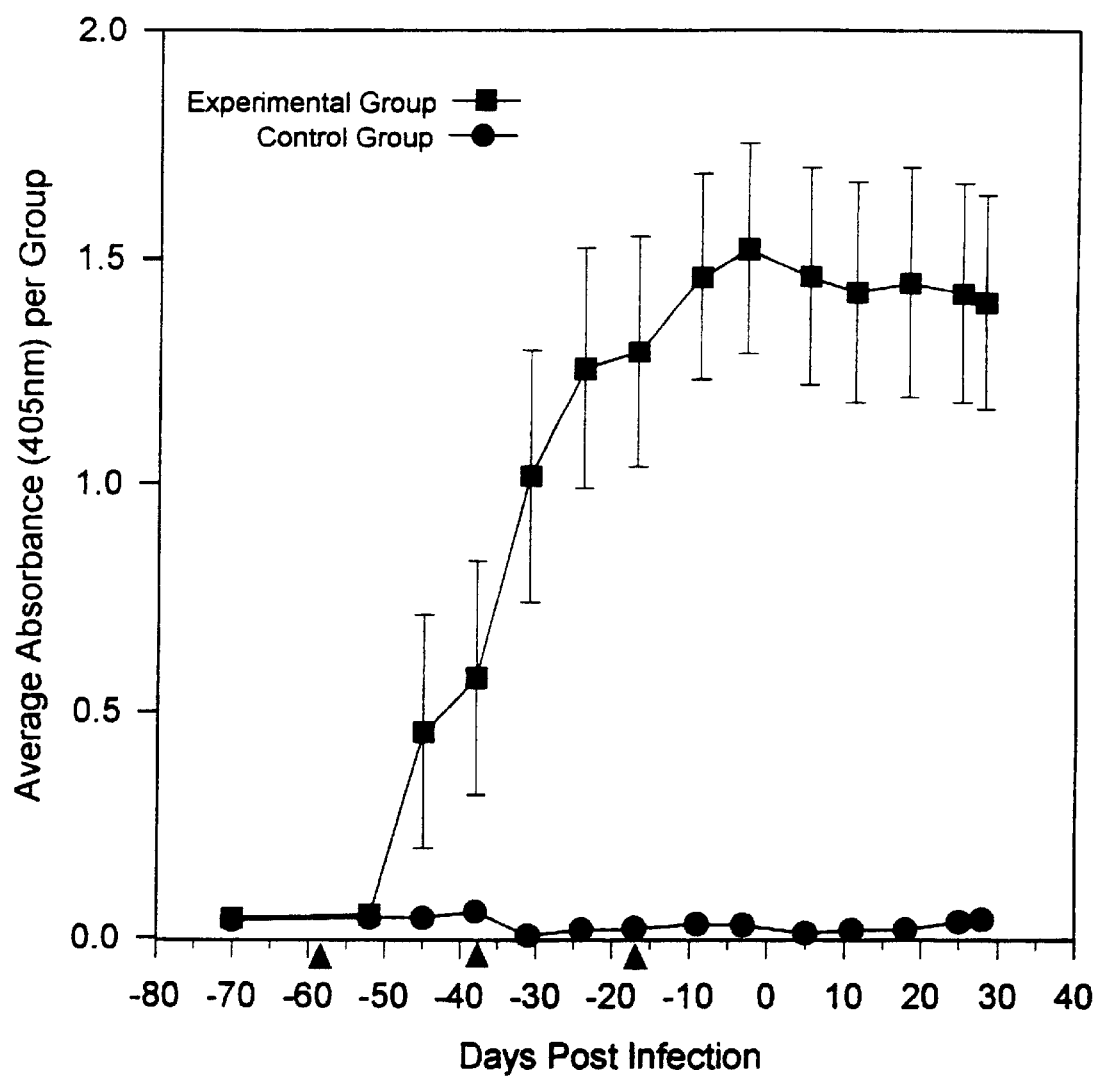

FIG. 23 Shows the recognition of ConA Oo12 by serum from cattle injected with ConA Oo12 (experimental group, squares) or ferritin (control group, circles), as measured by ELISA. The antiserum titre increased with time after injection of ConA Oo12 but not ferritin, illustrating the antigenicity of Oo12. The arrows indicates the time of the first, second and third injections of ConA Oo12 or ferritin. Thirty days after infection with O. ostertagi larvae, the control group did not show an increased antiserum titre against ConA Oo12 illustrating the hidden nature of the antigen in the source worm.

Figure 24A:
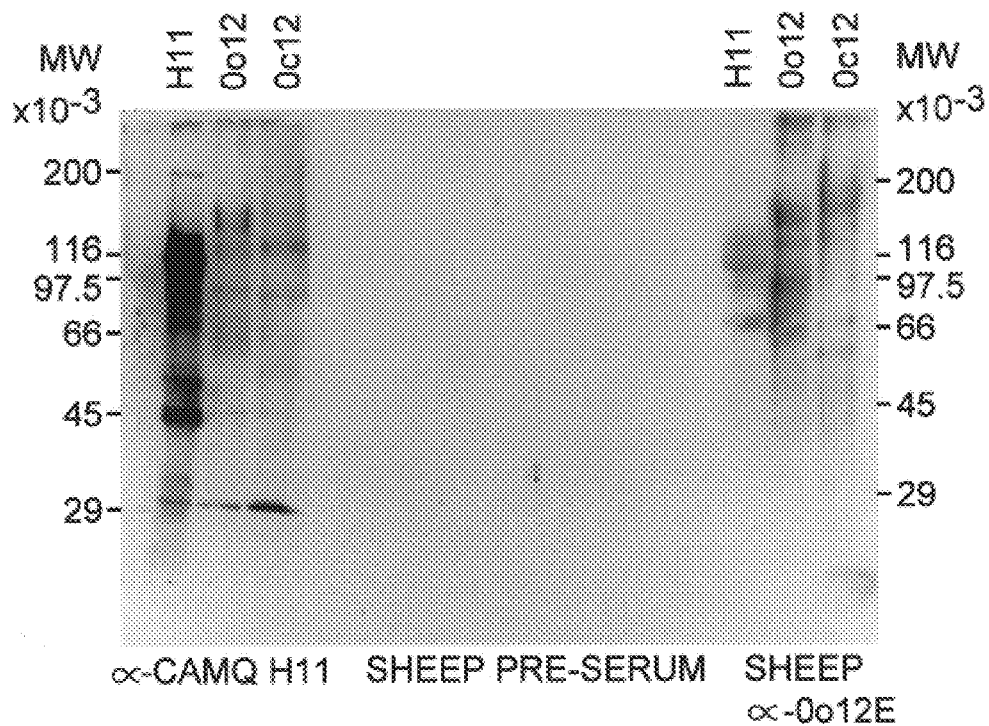
Figure 24B:
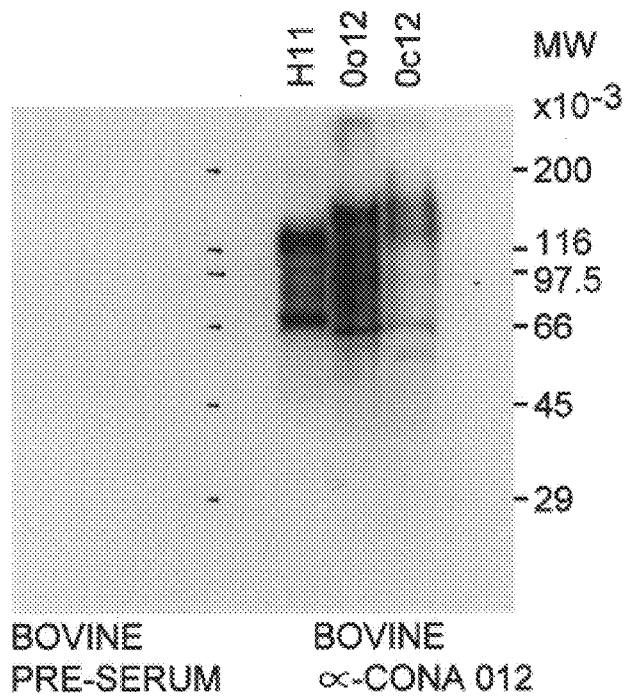

FIG. 24 Shows a Western blot of ConA Oo12, ConA H11 and ConA Oc12 probed with sheep anti-Oo12E (1:1000), bovine anti-ConA O12 (1:1000) and sheep anti-CamQ H11 IgG (1:100) sera.

Figure 25:
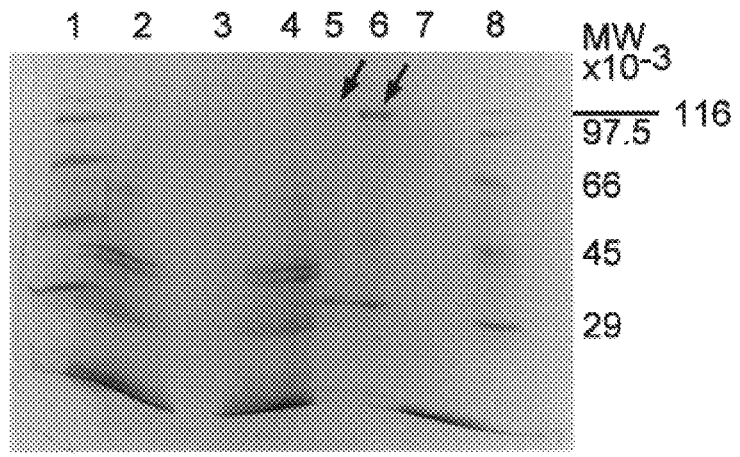

FIG. 25 shows a 6–16% denaturing, reducing SDS-PAGE gel of chymotrypsin digested PHP separated on ConA sepharose. Lanes 1 and 8 contain molecular weight markers, lane 2 contains starting material, lane 4 contains material which did not bind to the column, lanes 5 and 6 contain material having ApM activity and lane 7 contains 500 μg chymotrypsin alone. The arrows indicate bands at approximately 116000.

Figure 26:
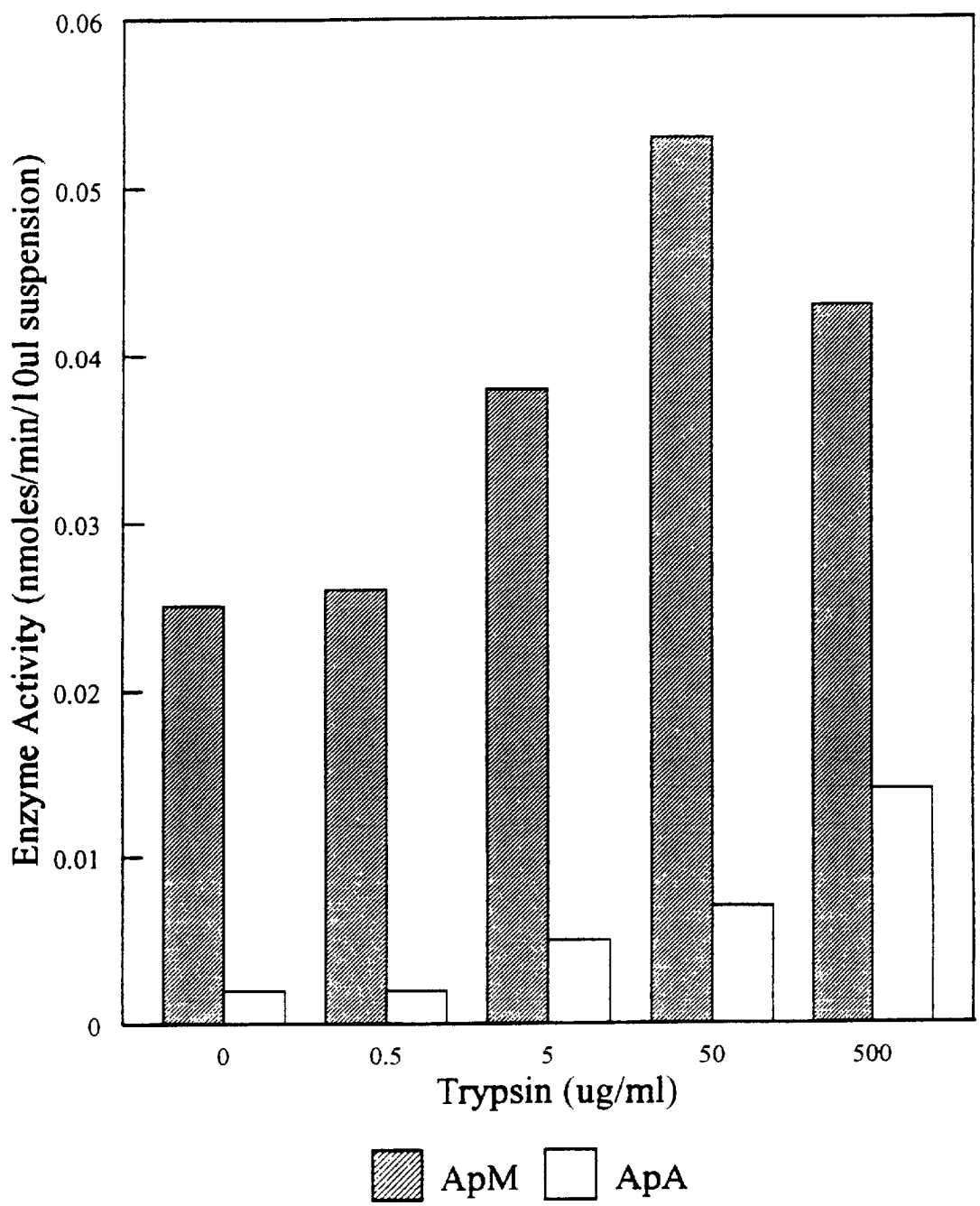

FIG. 26 shows the release of aminopeptidase activity from *Ostertagia ostertagi* after trypsin digestion at various concentrations of the protease.

Figure 27:
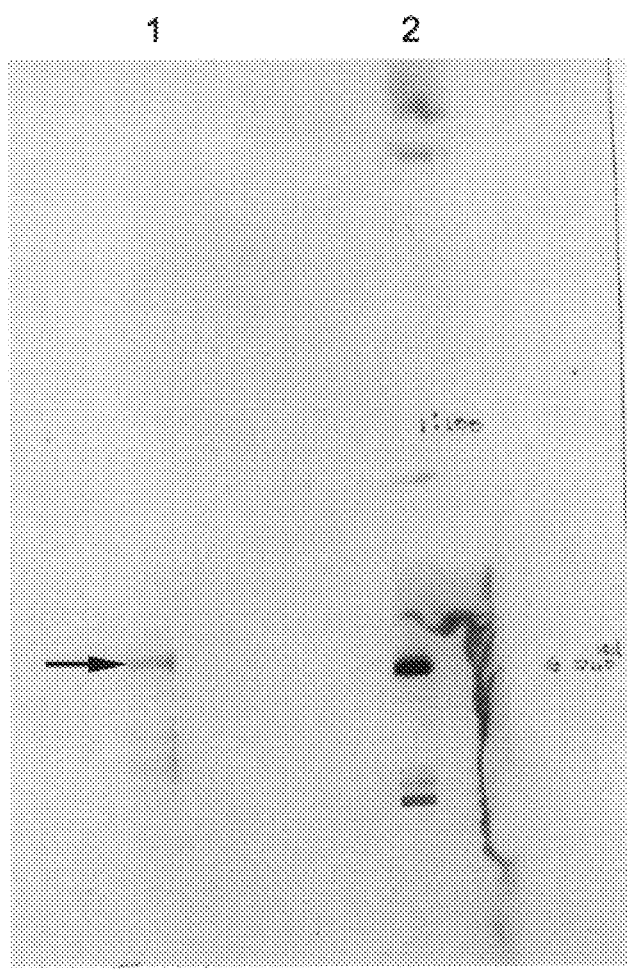

FIG. 27 shows a Western blot of ConA Oo12 after trypsin digestion and gel filtration on Superdex (lane 1) and ConA H11 (lane 2) run on a 6–16% denaturing, reducing gel, probed with a CamQH11 IgG at a dilution of 1:100 or 1:1000. The ConA Oo12 fraction from the Superdex fractionation contained ApM activity. Serum used at a concentration of 1:100 was found to cross-react with Oo12. The arrow indicates the band of approximately 116000.

Figure 28A:
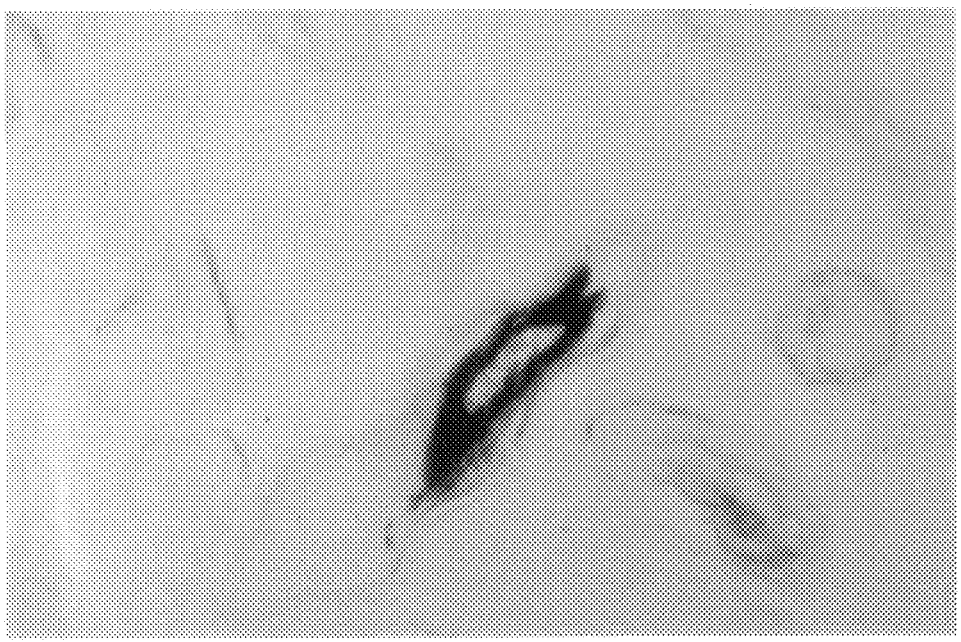
Figure 28B:
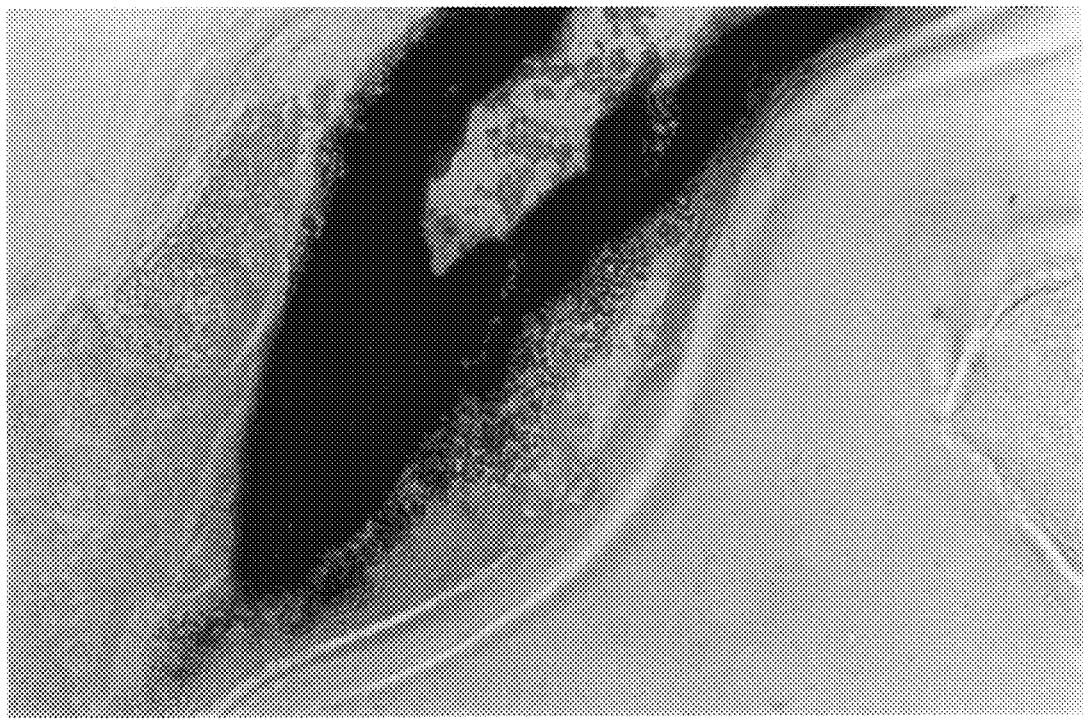

FIG. 28 shows the histochemical localisation of microsomal aminopeptidase activity within the intestine of Cooperia Oncophora using leucine-βMNA as substrate at a) low power, and b) high power, magnification.

EXAMPLE 1

Histochemistry

*O.ostertagi* and *O.circumcincta* adults were frozen in embedding compound for frozen sections and 10 μm cryosections were cut on a cryostat. Sections were then assayed using histochemical techniques for ApM-like and ApA-like activity as follows:

Aminopeptidase M

Based on methods by Nachlas, Crawford & Seligman (1957, J. Histochemistry and Cytochemistry 5, 264–278) and Lojda, Gossrau & Schiebler (1979, Enzyme Histochemistry. A Laboratory Manual, Springer Verlag, Berlin).

| Substrate | |
|---|---|
| L-alanine 4-methoxy-β-naphthylamide (Sigma) or | 0.7 mM |
| L-leucine 4-methoxy-β-naphthylamide (Sigma) | 0.7 mM |
| Dissolved in absolute ethyl alcohol | 0.05 ml |
| Distilled water | 0.45 ml |
| 0.1M acetate buffer pH 6.5 | 5 ml |
| Normal saline (0.85%) | 4 ml |
| 0.13% potassium cyanide | 0.5 ml |
| Fast Blue B (just before use) | 5 mg |

| Method | |
|---|---|
| 1. Dry sections at room temperature | 2 hr |
| 2. Fix in formal calcium at 4° C. | 10 min |
| 3. Rinse in normal saline at 4° C. (×2) | 2–3 min each |
| 4. Incubate at 37° C. in substrate | 5–10 min |
| 5. Rinse in normal saline | 2 min |
| 6. Rinse in 0.1M copper sulphate | 2 min |
| 7. Rinse in saline | 2 min |
| 8. Mount in glycerin jelly | |
| 9. Inhibit enzyme activity with the addition of 5 mM 1,10 phenanthroline to the incubation medium. | |

Enzyme activity appears bluish red.
Aminopeptidase A
(Lojda & Gossrau, 1980, Histochemistry 67, 267–290).

| Substrate | |
|---|---|
| L-Glutamic acid α-4-methoxy-β-naphthylamide (Sigma) | 0.94 mM |
| Dissolve in dimethyl formamide | 0.5 ml |
| 0.1M Phosphate buffer (pH 7.0) | 10 ml |
| Fast Blue B | 5 mg |
| CaCl | 10 mg |

Warm and filter
1% formalin in 3.58 CaCl

| Method | |
|---|---|
| 1. Dry sections at room temperature | 2 hr |
| 2. Fix in formal calcium (4° C.) | 10 min |
| 3. Rinse in phosphate buffer | 2 × 2 min |
| 4. Incubate in substrate | 10 min |
| 5. Rinse distilled water (4° C.) | 10 min |
| 6. Post fix (room temp) | 1 hr |
| 7. Rinse distilled water | |
| 8. Mount glycerine jelly | |

Enzyme activity appears red.

Figure 1A:
Figure 1B:
Figure 1C:
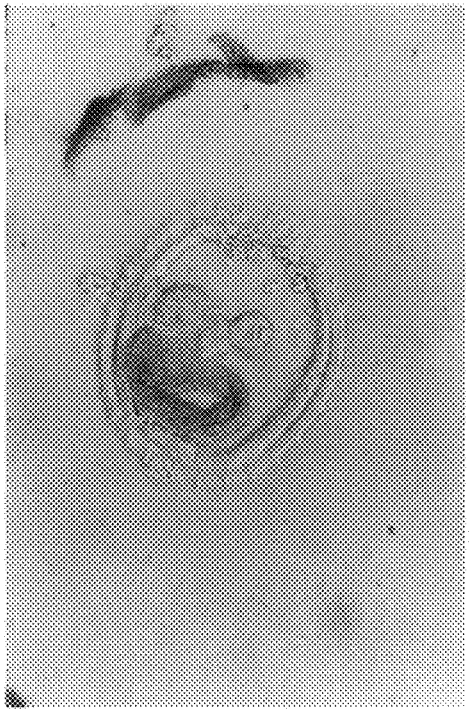
Figure 1D:

The results are shown in FIG. 1, which clearly shows both ApM-like and ApA-like activity associated with the intestinal microvilli of O. ostertagi (FIG. 1(a), ApM-like; FIG. 1(c), ApA-like) and O. circumcincta (FIG. 1(b); ApM-like; FIG. 1(d) ApA-like).

EXAMPLE 2

Ostertagi ostertagi

O.ostertagi was differentially extracted with PBS (to yield PHS extract), 1% Polyoxyethylene-sorbitan-monolaurate (Tween 20, a Registered trademark of IX+CI Americas Inc, Wilmington, USA) (TwHS extract) and Thesit (ThHS extract). The extracts were centrifuged at high speed (Beckman Airfuge, maximum speed, angle rotor) and the supernatant liquids were assayed for aminopeptidase M-like enzyme activity (see Table 1). Aminopeptidase A-like activity is also present in this extract but with a much lower specific and total activity. The ratio of aminopeptidase M (leu/met-pNA) to aminopeptidase A-like (α-glu-pNA) activity was approximately 4:1.

Figure 2:
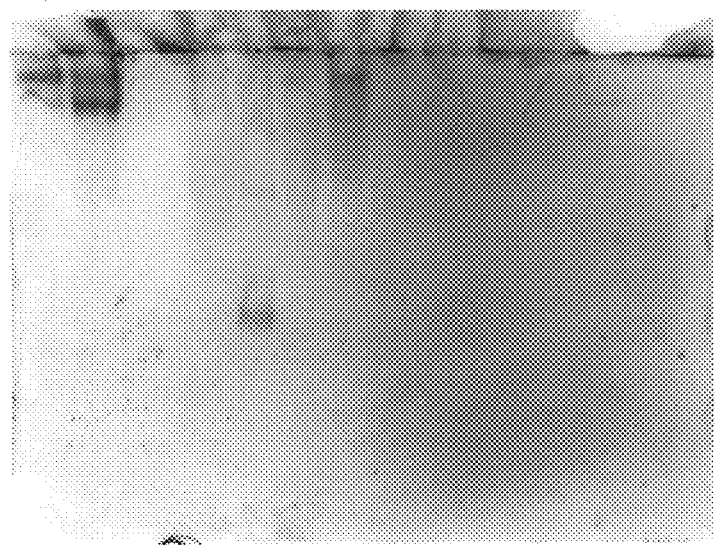
FIG. 2 Shows non-denatured 6–16% PAGE stained with L-alanine histochemical reagent for aminopeptidase activity. Track i) H10D-enriched preparation; ii) Thesit extract of Haemonchus contortus; iii) Blank; iv) Tween extract of Haemonchus; v), vi) and vii) PBS, Tween and Thesit extracts respectively of *Ostertagia ostertagi*; the arrow points to ApM-like activity in OoThHS.

The centrifuged O. ostertagi extracts (PHS, TwHS, ThHS) were run on 6–16% non-denaturing PAGE. For comparison H110D-enriched extracts from Haemonchus contortus were also run on the same gel. Aminopeptidase M activity was demonstrated on the gel using the alanine histochemical substrate. Activity was localised to a single band in the Thesit extract (designated OoThHS) of Ostertagia ostertagi which migrated the same distance as the slower of two bands having aminopeptidase M activity in the Haemonchus extract (FIG. 2). (A faster moving band was also visualised in the PBS extract of Ostertagia which may be cytoplasmic (non-integral membrane) leucine aminopeptidase).

The centrifuged Thesit extract (OoThHS) was dialysed in 10 mM Tris pH 7.2, 0.1% Thesit and applied to an anion exchange column (Pharmacia: SMART MonoQ column). The wash-through fractions and those binding fractions released by application of a sodium chloride gradient were collected (FIG. 3). Individual fractions were assayed for aminopeptidase M, and aminopeptidase A-like activities. Most aminopeptidase activity eluted at the start of the salt gradient (FIG. 4). Samples of the fractions were run on a 6–16% SDS-PAGE under reducing conditions and the separated proteins were visualised by silver staining (FIG. 5). The fractions containing most of the aminopeptidase activity had two particularly strong bands, one with an $M_r$ of about 125,000 (arrowed, FIG. 5) and a doublet with $M_r$ of about 32,000. These components were separated by gel filtration (on a SMART Superose 12 column), as shown by SDS-PAGE (FIG. 6). Fractions were assayed for aminopeptidase M-like activity. The activity was found only in the fractions containing the band with an $M_r$ of 125,000. This protein is designated Oo12.

Trypsin digestion of the pelleted material from O.ostertagi obtained after extraction with PBS released aminopeptidase activity in the ratio M/A-like of 8:1. The released protein may be separated by SDS-PAGE, the band excised from the gel and the protein transferred to membrane for N-terminal sequence analysis.

EXAMPLE 3

Ostertagia circumcincta

Homogenates of adult O.circumcincta were extracted successively in PBS, 1% Tween 20 and 1% Thesit. The extracts were centrifuged at high speed. The centrifuged Thesit extract (OcThHS) contained aminopeptidase M and aminopeptidase A-like activities (Table 2) and as found in O.ostertagi the aminopeptidase A-like specific and total activity is much lower than that of aminopeptidase M. The total aminopeptidase activities are lower than those found in O.ostertagi preparations, A band with $M_r$ of 124,000 (Oc12) is present in OcThHS (FIG. 7).

The O.circumcincta extracts were electroblotted alongside a sample of H110D and probed with several biotinylated lectins to determine which, if any, would bind to Oc12. (FIG. 8). Biotinylated Concanavalin A, Ulex europaeus, Triticum vulgaris, Dolichos biflorus and Arachis hypogea lectins were used at dilutions optimised for use with H110D. As shown in FIG. 8, biotinylated ConA lectin binds strongly to Oc12 (and to many other bands); D.biflorus lectin binds very weakly. There was virtually no binding of A. hypogea and T.vulgaris lectins. U.europaeus lectin bound to several low molecular weight bands and may be used as an affinity chromatography column for removing low molecular weight protein from OcThHS. The wash-through fractions from such a column were applied to a Con A affinity column and the bound proteins were eluted with a gradient of 0–100% 0.5M methylglucoside (FIG. 9). Fractions were assayed for aminopeptidase-like activity (FIG. 10). Aminopeptidase M-like activity was present in the binding fractions. When run on 6–16% SDS-PAGE under reducing conditions, only fractions demonstrating aminopeptidase M activity have a band with $M_r$ of 124,000 (FIG. 11).

The fractions with aminopeptidase activity were pooled and applied to an anion exchange column. The wash-through fractions and fractions released by a salt gradient were collected (FIG. 12). Aliquots were assayed for aminopeptidase M-like activities (FIG. 13). Aminopeptidase M activity was present in the fractions eluted with between 11% and 25% NaCl. Fractions were then run on 6–16% denaturing PAGE, but even after silver staining there was too little protein present to detect clear bands. As indicated for *Ostertagia ostertagi*, the aminopeptidase and proteins may be further purified by gel exclusion chromatography.

4. Resuspend pellet in PBSa+1% Thesit and mix overnight at 4° C. Centrifuge as above. Resuspend pellet on PBSa/thesit and mix for 1.5 hours at 4° C., centrifuge and repeat. Thesit low speed supernatants (ThLS 1–3) are pooled and ultracentrifuged at 100,000 g to give Thesit High Speed Supernatant (ThHS).

5. ThHS is buffer exchanged using a Pharmacia PD10 column or dialysed with ConA buffer A+0.1% thesit and run on a Conconavilin A (ConA) sepharose column.

6. ThHs is applied to the ConA column of either the FPLC or Pharmacia SMART system and unbound protein washed off with ConA buffer A. Bound material is eluted using 100% ConA buffer B, with a pause at the

TABLE 1

ENZYME ACTIVITIES OF *OSTERTAGIA OSTERTAGI* EXTRACTS

| EXTRACT | PROTEIN CONC mg/ml | TOTAL PROTEIN mg | VOLUME ml | ENZYME SPECIFIC ACTIVITIES (nmoles/mg protein/min) AND TOTAL ACTIVITIES (nmoles/min/total sample) ||||||||
|---|---|---|---|---|---|---|---|---|---|---|---|
| | | | | Leu-pNA || Met-pNA || Ala-pNA || α-Glu-pNA ||
| | | | | SA | TA | SA | TA | SA | TA | SA | TA |
| PHS | 3.15 | 62.68 | 19.9 | 2 | 129 | 6 | 384 | 12 | 726 | 0.3 | 18 |
| TwHS | 0.71 | 6.67 | 9.4 | 3 | 23 | 6 | 41 | 5 | 33 | 0.6 | 4 |
| ThHS | 0.55 | 3.08 | 5.6 | 62 | 189 | 74 | 227 | 10 | 31 | 17 | 51 |

TABLE 2

ENZYME ACTIVITIES OF *OSTERTAGIA CIRCUMCINCTA* EXTRACTS

| EXTRACT | PROTEIN CONC mg/ml | TOTAL PROTEIN mg | VOLUME ml | ENZYME SPECIFIC ACTIVITIES (nmoles/mg protein/min) AND TOTAL ACTIVITIES (nmoles/min/total sample) ||||||||
|---|---|---|---|---|---|---|---|---|---|---|---|
| | | | | Leu-pNA || Met-pNA || Ala-pNA || α-Glu-pNA ||
| | | | | SA | TA | SA | TA | SA | TA | SA | TA |
| PHS | 4.3 | 57.62 | 13.4 | 4 | 221 | 10 | 573 | 18 | 1061 | 0.1 | 4 |
| TwHS | 1.45 | 10 | 6.9 | 3 | 27 | 5 | 49 | 6 | 65 | 0.1 | 1 |
| ThHS | 0.8 | 2.96 | 3.7 | 36 | 108 | 41 | 122 | 10 | 30 | 7 | 21 |

EXAMPLE 4

Characterisation of Oo12 from *O. ostertagi*

The following studies were performed using Oo12 prepared as described in the following protocol in which Con A buffer A is 5 mM sodium acetate 1 mM manganese chloride, 1 mM anhydrous calcium chloride, 0.1M sodium chloride, 0.02% sodium azide, pH 5.2 and Con A Buffer B is a buffer A with the addition of 0.5M methyl-α-D-glucopyranoside and 0.2M methyl mannoside.

1. Homogenize worms in 10 vols. ice cold PBS+0.02% sodium azide (PBSa), centrifuge at low speed (17,000 g).
2. Resuspend pellet in 10 vols. PBSa and recentrifuge. Repeat PBSa resuspension and centrifugation once more. PBS low speed supernatant (PLS) can be ultracentrifuged at 100,000 g to give a high speed PBS supernatant (PHS) and high speed pellet (PHP).
3. Resuspend low speed pellet in 10 vols. PBSa+1% Tween 20 and mix for 1.5 hours at 4° C., spin at 17,000 g as above. Repeat washes and spins, twice.

start of elution of 15–20 minutes to maximise the yield of bound protein. Fractions eluted and containing ApM activity (as determined by microtitre plate enzyme assay) are run on 6–16% denaturing, reducing PAGE to ensure the presence of an O12 band and pooled to give ConA O12.

7. ConA O12 can then be dialysed or buffer exchanged into MonoQ buffer A (20 mM tris, pH7.2)+0.1% thesit before application to the Pharmacia MonoQ ion exchange column. Material is loaded onto the column in MonoQ buffer A and eluted using a gradient of 1%/ml MonoQ buffer B (Mono Q buffer A and 1M NaCl) and after reaching 30%, 3%/ml up to 100% buffer B. Eluted fractions containing ApM activity and an O12 band are pooled to give CamQ O12.

Inhibitor studies
Method

The effect of various protease inhibitors on Oo12 activity was assayed and included amastatin (aminopeptidase inhibitor), actinonin (aminopeptidase inhibitor), bestatin (aminopeptidase inhibitor), EDTA (metallo-protease inhibitor), E64 (cysteine protease inhibitor), pepstatin (aspartic protease inhibitor), 1,10 phenanthroline (metalloprotease inhibitor) and 3,4-dichloroisocoumarin (DCI, serine protease inhibitor). 10 μl Con A Oo12 and 100 μl 50 mM Mops buffer, pH 7.0 was added to a microtitre plate well and 2–4 μl of enzyme inhibitor added, to give a final concentration of 0.5 mM and 1 mM actinonin, 50 μM and 100 μM bestatin, 1 mM and 15 mM EDTA, 50 μM and 100 μM E64, 10 and 50 μM pepstatin, 1 mM and 10 mM 1,10 phenanthroline, 100 μM and 500 μM DCI. The plate was preincubated at 37° C. for 20–28 minutes and then assayed for ApM and ApA activity. 100 μl 2 mM leucine p-nitroanilide (ApM) or α-glutamic p-nitroanilide (ApA)/ Mops was added per well and the optical density (OD) at 405 nm read using an Elisa plate reader. The plates were incubated at 37° C. for 45–48 minutes and the final OD reading was then taken. The OD change per minute per 10 μl sample was calculated. All assays were carried out in triplicate.

Results

See Table 3. As expected, only metallo-protease and aminopeptidase inhibitors had any inhibitory effect on aminopeptidase activity with 10 mM phenanthroline giving the greatest inhibition. The differential effects of amastatin on ApM and ApA activity are similar to those described previously for H11 (Graham, et al., WO 93/23542), distinguishing Oo12 Ap activity from mammalian Ap. Aoyagi et al. (J. Antibiotics, 43(2): 143–148) demonstrated amastatin as a better inhibitor of pig ApA than of ApM and the opposite is found with H11 and Oo12.

Substrate Specificity

Method

ConA Oo12 was assayed for enzyme activity in triplicate, on a microtitre plate using a range of substrates. 5 μl of ConA Oo12 (buffer exchanged into PBS/0.1% thesit) or ConA H11 (in ConA buffer B) was added to each well together with 100 μl of 50 mM Mops pH 7.0 (or 90 mM citrate buffer+10 mM NaCl, pH 5.0 for acid phosphatase and 50 mM Tris, pH 9.0 for γ-GTP. The plate was preincubated for 15 minutes and then 100 μl 2 mM substrate added (in the appropriate buffer) before the OD was measured. The plate was incubated at 37° C. for 26 minutes and the OD measured again. For acid phosphatase, the reaction was stopped by adding 75 μl 1.66M NaOH/well. The ratio of enzyme activity was calculated with methionine taken as having an OD of 1.

Results

See Table 4. ConA Oo12 shows greatest specificity for methionine and the greatest difference between ConA Oo12 and ConA E11 is the lower specificity of Oo12 for lysine and very low γ-GTP activity.

pH Optima of Oo12 Ap Activity

Method

ConA Oo12 in either ConA buffer A/0.01% Thesit or PBS/0.1% Thesit was assayed for aminopeptidase activity using either α-glutamic-pNa (ApA substrate), methionine-pNa or leucine-pNA (ApM substrates). 50 mM MRS (pH 5.5–6.5) and 50 mM MOPS (pH 6.5–8.0) were chosen as buffers, covering a broad pH range and overlapping at pH 6.5. Buffers were prepared using volumetric flasks and MilliQ ultra pure water and the assays were carried out in triplicate on microtitre plates (as described above). 5 μl of ConA Oo12 or 5 μl ConA H11 (in ConA Buffer B, for comparison) were added per well and the OD change was measured over 13.6–25 minutes.

Results

See FIGS. 14–16. Differences in the pH profiles between substrates and between O12 and H11 are found, although generally the optimum pH for Aminopeptidase activity is between 6.5–7.0. There is also some variability in activity when using MOPS and MES at pH 6.5, indicating that buffer composition also influences activity.

TABLE 3

CON A O12 (OO) AMINOPEPTIDASE INHIBITION ASSAYS

| INHIBITOR | CONC INHIBITOR/ 10 μl ConA O12 | ENZYME ACTIVITY (nmoles/min/10 μl ConA O12) and ENZYME INHIBITION | | | |
|---|---|---|---|---|---|
| | | Leu-pNA | | α-Glu-pNA | |
| | | Activity | Inhibition | Activity | Inhibition |
| None | — | 1.224 | — | 0.334 | — |
| Actinonin | 0.5 mM | 0.621 | 49% | 0.016 | 95% |
| " | 1 mM | 0.448 | 63% | 0.029 | 91% |
| Bestatin | 50 μM | 0.045 | 96% | 0.174 | 48% |
| " | 100 μM | 0.022 | 98% | 0.119 | 64% |
| EDTA | 1 mM | 0.994 | 19% | 0.161 | 52% |
| " | 15 mM | 0.784 | 36% | 0.112 | 66% |
| E64 | 50 μM | 1.241 | 0 (+1%) | 0.323 | 3% |
| " | 100 μM | 1.278 | 0 (+4%) | 0.327 | 2% |
| Pepstatin | 10 μM | 1.297 | 0 (+6%) | 0.326 | 2% |
| " | 50 μM | 1.263 | 0 (+3%) | 0.315 | 6% |
| 1,10 Phenanthroline | 1 mM | 0.005 | 99% | 0 | 100% |
| 1,10 Phenanthroline | 10 mM | 0 | 100% | 0 | 100% |
| DCI | 100 μM | 1.229 | 0% | 0.252 | 24% |
| " | 500 μM | 1.129 | 8% | 0.216 | 35% |
| — | — | 1.591 | — | 0.320 | — |
| Amaststin | 10 μM | 0.218 | 86% | 0.282 | 12% |
| " | 50 μM | 0.074 | 95% | 0.205 | 36% |

TABLE 4

Substrate Specificity of ConA Oo12 and ConA H11

| | ENZYME ACTIVITIES (nmoles/min/5 μl) AND RATIO of ACTIVITY (Met-pNA = 1) | | | |
|---|---|---|---|---|
| | ConA Oo12 | | ConA H11 | |
| SUBSTRATE | Activity | Ratio | Activity | Ratio |
| Met-pNA | 0.635 | 1 | 1.271 | 1 |
| Leu-pNA | 0.529 | 0.83 | 0.985 | 0.77 |
| Lys-pNA | 0.059 | 0.09 | 0.465 | 0.36 |
| Ala-pNA | 0.093 | 0.15 | 0.311 | 0.24 |
| Pro-pNA | 0.021 | 0.03 | 0.015 | 0.01 |
| Arg-pNA | neg | 0 | 0.142 | 0.11 |
| Gly-Pro-pNA | neg | 0 | neg | 0 |
| 2nd Plate | | | | |
| Met-pNA | 0.554 | 1 | 1.208 | 1 |
| α-Glu-pNA | 0.18 | 0.32 | 0.569 | 0.47 |
| γ-Glut-pNA | 0.019 | 0.03 | 1.640 | 1.36 |
| Acp | 1.673 | 3.02 | 3.412 | 2.82 |

Assays carried out in 50 mM Mops, pM 7.0 except for AcP (90 mM citrate buffer, pH 5.0) and γGTP (50 mM Tris, pH 9.0). Assays carried out over 26 min.

EXAMPLE 5

Polymerase Chain Reactions

Preparation of mRNA 80 mg. of 12 day old *Ostertagia ostertagi* (UK strain) flash frozen and stored in liquid nitrogen were ground to a power under liquid nitrogen and the mRNA extracted using a micro mRNA extraction kit (Pharmacia) according to the manufacturer's instructions. Briefly, the powdered nematodes were solubilised in a solution containing guanidinium thiocyanate and N-lauroyl sarcosine and then the mRNA extracted from the aqueous solution with oligo (dT)-cellulose. The mRNA was stored under ethanol at −80° C. until use.

Preparation of First Strand cDNA mRNA, from the equivalent of 10 mg. of *O. ostertagi,* as prepared above was used for the preparation of first strand cDNA. The mRNA was dissolved in 11.5 µl of sterile water and 1 µl of a T17 adaptor-primer, 0.5 µg/µl, (5' GACTC-GAGTCGACATCGATTTTTTTTTTTTTTTTT 3') (SEQ ID NO:33) added. This mixture was heated to 65° C. for 10 minutes, left at room temperature for 2 minutes, then placed on ice. To synthesize cDNA the following components from a cDNA cycle kit (Invitrogen) were added, RNase Inhibitor to 0.5 units/µl, Reverse transcriptase buffer to 1× concentration, dATP, dGTP, dCTP and dTTP to 1.25 mM, Sodium pyrophosphate to 4 mM and AMV Reverse Transcriptase to 0.5 units/µl (all given as final concentrations). The reaction mix was incubated at 42° C. for 65 minutes and then heated at 98° C. for 2 minutes. The reaction mix was diluted by addition of 100 µl water, then extracted with phenol and the cDNA purified by spun column chromatography. (Maniatis et al, 1982). The cDNA was stored at 4° C.

PCR Amplification of the cDNA using Aminopeptidase-Specific Primers

The Primers

DNA sequence data from the nematodes *H. contortus* (WO 93/23542) and *Caenorhabditis elegans* with homology to mammalian aminopeptidase were compared and a conserved region coding for the amino acids: Gly Ala Met Glu Asn Trp Glu Leu (SEQ ID NO:43), was obtained. Both sense and anti-sense primers were manufactured based on this sequence. The sense primer was 5' GGWGCNATGGA-RAAYTGGGGNCT 3' (SEQ ID NO:3) and the anti-sense 5' AGNCCCCARTTYTCCATNGCWCC 3' (SEQ ID NO:4).

The sense primer described above can be used with the adaptor sequence from the T17 adaptor-primer, 5' GACTC-GAGTCGACATCGA 3' (SEQ ID NO:34), to PCR with the first strand cDNA from *O. ostertagi.*

Some 5' ends of cDNAs of various helmrinths have been shown to have a conserved region of 22 base pairs before the initiating methionine (Huang 1990). This region, known as Spliced leader 1 (SL1), has the sequence 5' GGTTTAAT-TACCCAAGTTTGAG 3' (SEQ ID NO:5). This spliced leader has been identified at the 5' end of microsomal aminopeptidase of *H. contortus* (WO 93/23542). This spliced leader paired with the anti-sense primer described above can be used to perform PCR with the first strand cDNA from *O. ostertagi.*

Polymerase Chain Reactions

The reactions were carried out using a Programmable Thermal Cycler (M. J. Research Inc). The first reaction mix contained 1 µl of *O. ostertagi* first strand cDNA, 1 pmol of T17 adaptor-primer, 25 pmol of the adaptor, 25 pmol of the sense primer, 1× Taq buffer (Boehringer Mannheim), 0.2 mM each of dATP, dCTP, dGTP and dTTP, in a reaction volume of 100 µl. The second reaction mix contained 1 µl of cDNA, 25 pmol of SL1 primer, 25 pmol of the anti-sense primer and then as for the first reaction mix. The reaction mixes were heated to 95° C. for 2 minutes and then held at 80° C. whilst 3 units of Taq Polymerase (Boehringer Mannheim) were added to each. The following programme was then performed:

Step 1 53° or 56° C. for 5 minutes
Step 2 72° C. for 20 minutes
Step 3 94° C. for 45 seconds
Step 4 53° or 56° C. for 2 minutes
Step 5 72° C. for 2.5 minutes
Step 6 39 times to Step 3
Step 7 72° C. for 15 minutes
Step 8 Hold at 4° C.

Purification and Cloning of PCR Products

The reaction products were separated by electrophoresis through a 1% agarose gel in TAB buffer (Maniatis 1982). The banding pattern was the same for reactions at 53° C. or 56° C. for both primer combinations and so the reaction products for each pair of primers were mixed. These combined reaction products were electrophoresed on a TAE gel and bands of interest were excised and the DNA purified with glassmilk (Geneclean, BIO 101).

The purified DNAs were ligated into the plasmid vector pT7Blue (Novagen) and then used to transform competent Novablue (Novagen) *E. coli* cells. The transformed *E. coli* were plated out to allow colour selection of colonies containing an insert plus the vector. DNA from putative positive colonies was prepared and electrophoresed in a TBE gel (Maniatis 1982), to allow selection of clones with an insert of the desired size.

Sequencing of Clones

Clones were sequences by 'oligonucleotide walking' of the double-stranded DNA with T7 DNA polymerase using GTP and ITP labelling from a Sequenase 2.0 Sequencing kit (Amersham).

EXAMPLE 6

Oo12E Sheep Antiserum 1.242 mg ConA Oo12 was run on a 0.7 mm 8% denaturing, reducing PAGE, adjacent to high molecular weight protein standards. Thin strips were cut from either side of the gel and stained with Coomassie blue to locate the O12 band. These strips were then re-aligned with the gel and the unstained O12 band position estimated and cut out. The gel was homogenised and mixed with Freund's adjuvant and injected into a single sheep, to raise antibodies to Oo12E (Oo12—after electrophoresis). A second injection was administered after 4 weeks using the above method and with the amount of protein run on the gel increased to 1.863 mg. Blood was collected from the sheep, and serum prepared, at regular intervals. The α-Oo12E serum was used to probe 10 mM sodium periodate treated western blots of ConA Oo12 and ConA H11. ConA Oo12 demonstrated strongly immunoreactive bands at about 120,000 and 170,000 and slightly weaker bands at 97 and 55 kDa (FIG. 17). In ConA H11 an immunoreactive band was present at about 70 kDa with H11 appearing very faint. The appearance of an immunoreactive band at 170,000 kDa in ConA O12 requires further investigation.

Serum antibody titres were also measured using the Elisa method, Dynatech Immulon 4 Elisa plates were coated with 50 µl/well 3 µg/ml ConA Oo12 at 4° C. overnight. Plates were washed in 3× PBS and blocked for 1 hour at 37° C. in PBS/lot foetal calf serum (FCS). Half the plate was treated with 150 µl/well 10 mM sodium metaperiodate in 0.1M sodium acetate buffer pH 5.5 for 30 minutes and then 150 µl 50 mM sodium borohydrate in PBS for 30 minutes at room temperature. The other half of the plate was treated with acetate buffer then PBS alone. Wells were rinsed 3× PBS and 100 µl/well primary antiserum (serum from the sheep pre- and post-injection) diluted 1:1000 in PBS/10% FCS added. Each serum was assayed in triplicate and applied to both sodium metaperiodate treated and untreated wells. The plate was incubated for 1 hour at 37° C., rinsed 3× PBS/0.05% Tween 20 and 50 µl/well donkey a-sheep IgG peroxidase conjugate added, diluted 1:1000 in PBS/10% FCS. The plate was incubated at 37° C. for 1 hour, rinsed 3× PBS/Tween and developed using Tetramethyl Benzidine (TMB) by the addition of 150 µl/well of the following developing solution: 18 ml MilliQ water, 2 ml 1M sodium acetate pH 6.0, 200 µl TMB (10 mg/ml in DMSO) and 20 µl 6% $H_2O_2$. Development was left for 10 minutes and stopped with 30 µl/well 3M $H_2SO_4$. The OD was read on an ELISA plate reader at 450 nm.

Results

See FIG. 18. Oo12E is antigenic in the sheep with antiserum titres rising with time. Sodium periodate treatment of the antigen results in decreased OD's suggesting that the majority of the immune response is directed towards carbohydrate and less so to protein epitopes.

EXAMPLE 7

Con A Oo12 Bovine Antiserum

Con A Oo12 was prepared from thesit extracted *O. ostertagia* according to the protocol given at the beginning of Example 4. 6 calves, aged between 12 and 27 weeks old, were given 3 injections of ConA Oo12 in Freund's adjuvant. 250 µg/calf was administered for the first two doses and 200 µg in the final injection with injections given at 3 week intervals. 6 calves in the control group were each given three injections of 150 µg ferritin in Freund's adjuvant (Type 1, from horse spleen). Calves were then challenged with 40000 infective *O. ostertagi* larvae. Serum was prepared from samples of blood collected weekly and serum antibody titres were measured using the Elisa method as follows.

Dynatech Immulon 4 Elisa plates were coated with 50 µl/well 3 µg/ml ConA Oo12 at 4° C. overnight. Plates were washed in 3X PBS and blocked for 1 hour at 37° C. in PBS/5% foetal calf serum (PCS). Wells were rinsed 3X with PBS/0.05% Tween 20 and 100 µl/well primary antiserum diluted 1:1000 in PBS/5% FCS added. Each serum was assayed in triplicate. The plate was incubated for 1 hour at 37° C., rinsed 3X with PBS/0.05% Tween and 50 µl/well rabbit α-bovine IgG peroxidase conjugate added, diluted 1:1000 in PBS/5% FCS. The plate was incubated at 37° C. for 1 hour, rinsed 3X with PBS/Tween and developed using tetramethyl Benzidine (TMB) by the addition of 150 µl/well of the following developing solution: 18 ml MilliQ water, 2 ml 1M sodium acetate pH 6.0, 200 µl TMB (10 mg/ml in DMSO) and 20 µl 6% $H_2O_2$. Development was left for 15 minutes and stopped with 30 µl/well 3M $H_2SO_4$. The OD was read at 450 nm.

Results

See FIG. 23. Con A Oo12 is antigenic in cattle with antiserum titres rising with time.

EXAMPLE 8

Immunoreactivity of Bovine and Sheep Oo12 Anti-Serum

ConA Oc12 was prepared from *O. circumcincta* using the standard thesit extraction protcol with a freshly packed ConA sepharose column and bound material was eluted from the column with 0.5M methylglucopyranoside and 0.2M methylmannoside in ConA buffer. ConA Oc12 was run on two 6–16% denaturing, reducing gels together with ConA Oo12 and ConA H11. About 4 µg of each preparation was run per lane. The proteins were then western blotted onto Immobilon P and probed with the following sera: sheep anti-CamQ H11 IgG (1:100), sheep anti-Oo12E (as prepared in Example 6, 1:1000), bovine anti-ConA Oo12 sera (as prepared in Example 7, 1:1000) and pre-immune sheep and bovine sera (1:1000) as negative controls.

Results

See FIG. 24. ConA H11, ConA Oo12 and ConA Oc12 demonstrated immunoreactivity to all three immune sera. Oo12 appeared smaller than Oc12, which may have resulted from degradation of the former. Oc12 cross-reacts with antisera to Oo12 and together with the evidence that Oo12 elicits an immune response in sheep, this suggests that Oo12 may have utility as a bivalent vaccine, acting against *O. circumcincta* as well the source worm.

EXAMPLE 9

Proteolytic Digestion of O12

Protease Digestion of Oo12 PhP

Method: Oo PhP was resuspended in 50 mM Mops buffer, pH 7.0 to give 0.1 mg pellet/ml. 50 µl aliquots were prewarmed at 37° C. for 39 minutes. 5 µl of either α-Chymotrypsin (Sigma type VII, 50 units/mg solid), Subtilisin (Sigma type VIII, 11.6 units/mg solid), Trypsin (Sigma, TPCK-treated type XIII, 9700 units/mg solid) or Thermolysin (Sigma, 37 units/mg solid dissolved in 1 mM KCl/2 mM CaCl) was added to give final protease concentrations of 5, 50, 500, 1000 and 2000 µg/ml. Aliquots containing chymotrypsin, trypsin or subtilisin were then incubated at 37° C. for 1 hour and protease activity inhibited by the addition of 1 µl 10 mM 3,4-dichloroisocoumarin (DCI). Aliquots containing thermolysin were incubated for 2 hours at 37° C. and activity inhibited by the addition of 1 µl 0.25M EDTA. Samples were spun at high speed on the airfuge at 20 psi for 20 minutes at room temperature. 5 µl samples were assay for ApM activity, using the microtitre plate method, over 29.6 minutes with methionine-pNA as substrate.

Results

See Table 5. All four proteases released ApM from the PhP, but thermolysin proved to be the least effective.

Chymotrypsin Digestion of PHP

The above experiment was performed on a larger scale to further purify the released ApM activity.

Oo PHP 2 and 3 were resuspended in 50 mM Mops pH 8.0 to give 0.1 mg pellet/ml and 4.5 ml was prewarmed at 37° C. for 20 minutes. The digestion was carried out as above with α-chymotrypsin added to give 500 µg protease/ml suspended PHP. Protease activity was inhibited by the addition of 15 µl/ml 10 mM DCI. The digests were then spun twice on a Beckman ultracentrifuge using a SW60 swing-out rotor at 31000 rpm for 1 hour 20 minutes. Enzyme assays demonstrated the release of ApM and ApA activity from the PHP (0.734 nmoles/min/10 µl with Met-pNA; 0.414 nmoles/min/10 µl with Leu-pNA and 0.304 nmoles/min/10 µl with α-Glu-pNA). The remaining supernatant was buffer exchanged using a Pharmacia PD10 column into ConA Buffer A and this was loaded onto a freshly packed ConA sepharose column for the SMART system. Material was loaded onto the column in ConA buffer A and eluted in one step using 100% ConA buffer B containing 0.5M methylglucopyranoside and 0.2M methylmannoside. Only eluted fractions contained ApM activity and these were pooled and run on 6–16% PAGE. A strong band was apparent at around 116000 in these fractions (FIG. 25). Pooled fractions were concentrated in a centricon 10 and run on a 6–16% denaturing, reducing minigel together with undigested PHP, chymotrypsin only, ConA Oo12 and ConA H11 for comparison. This was western blotted (using the BioRad semi-dry system) onto Immobilon P, treated with 10 mM sodium metaperiodate and probed with Sheep α-Oo12E (1:1000). A strongly immunoreactive band was apparent at about 116000–120000 in the digested pellet. Supernatant from digested PEP was run on a second gel using tank buffer containing 0.192M tricine instead of glycine. The gel was blotted and probed as above and the immunoreactive band excised from the blot and the amino acid sequence analysed. No matches to any known sequences were found.

Trypsin digestion of O12

The residue obtained by centrifuging an homogenate of O. ostertagi in phosphate-buffered saline containing 0.02% sodium azide (PBSa) at 26,500 g (max) for 20 minutes in a swing-out rotor was re-extracted 3 times with PBSa, once with 1% polyoxyethylenesorbitan monolaurate (Tween 20) in PBSa and once with 50 mM 3-[N-morpholino]propane-sulphonic acid (MOPS) pH 8.0. The extracted residue was resuspended in 50 mM MOPS to give the equivalent of 0.17 g worm starting material per ml. Aliquots were digested with 0.5, 5, 50 or 500 µg TPCK-trypsin (trypsin treated with L-1-tosylamide-2-phenylethylchloromethyl ketone)/ml. Digestions were stopped by the addition of 10 mM DCI (15 µl/ml). Treatment with 50 µg TPCK-trypsin (485 units) released the greatest amount of microsomal aminopeptidase M activity (FIG. 26). Release of microsomal aminopeptidase A activity was negligible from pellets digested with 0–50 µg TPCK-trypsin/ml.

In another experiment material from 5 g O. ostertagi was digested twice with 50 µg/ml TPCK-trypsin. About 33% of the original amount of ApM was released after a second digest. Both digests were pooled and subjected to affinity chromatography on Concanavilin A. Microsomal aminopeptidase M activity bound to the column, but only 32% of the applied activity was eluted with 0.5M methylglucopyranoside. Fractions were run on SDS-PAGE on a 6–16% minigel. After Coomassie blue staining, a band located around the 116,000 region, about the size expected from tryptic digestion of O12 was located in the fractions having the microsomal aminopeptidase activity. (Amino acid sequences from this and the adjacent bands did not match any sequence in the data bases.)

A further 4.3 g of O. ostertagi was digested twice with TPCK-trypsin as above. The total aminopeptidase activity solubilised equalled 455 nmoles/min (Table 6). The high speed supernatants from the first and second digests (Trypsin HS1 & HS2) were buffer exchanged with ConA buffer A and run on a ConA sepharose column. The start material applied to the column was enriched for ApM activity, having a ratio of ApM:ApA of 18:1. All the ApM activity bound to the column (there was none in the wash-through); and 67% of this was recovered by elution with 0.5M methylglucopyranoside+0.2M methylmannoside. (Thus the use of two sugars in the eluting buffer more than doubled ApM recovery from the ConA column.) Fractions containing ApM activity were pooled, concentrated and subjected to gel filtration (on an FPLC Superdex 75 HR10/30 (Pharmacia) column). Fractions were concentrated, assayed for ApM activity and run on 6–16% SDS PAGE. Several protein bands were present. After Western blotting and probing with anti-CamQEH11 antibody, a band at between 110,000–116,000 proved immunoreactive (FIG. 27). ConA and Superdex fractions were re-run on a 6–16% reducing/denaturing minigel, with tank buffer containing 0.192 M tricine instead of glycine and electroblotted onto Problott. Several bands were cut out and sequenced (but did not yield sequences which matched any sequence in the data bases.)

The sequences obtained after proteolytic digestion are as follows:

EPLAPGAANP KGVANDTMQF (SEQ ID NO:6)

DXEEEXQPEN GXRTRGRXPX (SEQ ID NO:7)

DEXCAVPEEA XGVDXPVXGE (SEQ ID NO:8)

XVFPGTEYGA LLQFAQANAQ RQNLR (SEQ ID NO:9)

DVPGADDDNG QDNDGEFVGE (SEQ ID NO:10)

APFEDDAPPA GGPKGLLEXL SAGLA (SEQ ID NO:11)

LQNQLPAF (SEQ ID NO:12)

KXDPGDGNYG GGXGGFQGHL (SEQ ID NO:13)

SIPNGDTGPX XNGYXAENYN QGGXE (SEQ ID NO:14)

DXEPGPREPG GSEGERQPEE G (SEQ ID NO:15)

XAEDLRLPTN IRPLIYDLTR (SEQ ID NO:16)

RGVVXPVDXX QTPVPGQPVN (SEQ ID NO:17)

XXQGSPYDXX (SEQ ID NO:18)

ApM activity has been successfully extracted from pellets recovered from ultracentrifuged PBSa and 1% Tween 20 extracts of O. ostertagi using either 1% thesit or 500 µg TPCK-trypsin/0.15 g pellet. Trypsin digests were western blotted probed with anti-CamQH11 IgG and immunoreactive bands cut out for amino acid sequencing, however no usable sequence could be determined.

TABLE 5

AMINOPEPTIDASE m ACTIVITY RELEASED BY PROTEASE DIGESTION OF OSTERTAGIA OSTERTAGI PHP

| µg Protease/ 0.1 mg PHP/ml | ENZYME ACTIVITY (nmoles/min/5 µl high speed supernatant) Met-pNA |
|---|---|
| 0 | 0.08 |
| α-Chymotrypsin | |
| 5 | 0.08 |
| 50 | 0.15 |
| 500 | 0.37 |
| 1000 | 0.54 |
| 2000 | 0.88 |
| Subtilisin | |
| 5 | 0.06 |
| 50 | 0.10 |
| 500 | 0.35 |
| 1000 | 0.66 |
| 2000 | 0.95 |
| Trypsin | |
| 5 | 0.118 |
| 50 | 0.246 |
| 500 | 1.075 |
| 1000 | 1.273 |
| 2000 | 1.068 |
| Thermolysin | |
| 0 | 0.06 |
| 5 | 0.06 |
| 50 | 0.07 |
| 500 | 0.08 |
| 1000 | 0.11 |
| 2000 | 0.19 |

TABLE 6

AMINOPEPTIDASE ACTIVITY FROM TRYPSIN DIGESTED *OSTERTAGIA OSTERTAGI*

| EXTRACT | PROTEIN CONC µg/ml | TOTAL PROTEIN mg | VOLUME ml | ENZYME SPECIFIC ACTIVITY (mnoles/min/mg) and TOTAL ACTIVITY (nmoles/min/total sample) | | | |
|---|---|---|---|---|---|---|---|
| | | | | Het-pNA | | α-Glu-pNA | |
| | | | | SA | TA | SA | TA |
| Trypsin HS1 | 1147 | 24 | 21.12 | 14 | 350 | 1 | 27 |
| Trypsin HS2 | 252 | 5.6 | 22.35 | 19 | 105 | 0 | 0 |

EXAMPLE 10

ApM Localisation in *Cooperia oncophora*

10 µm frozen sections of *Cooperia oncophora* were stained histochemically for ApM activity using leucine-βMNA (as performed in Example 1). ApM activity was found to be localised to the intestinal microvilli (see FIG. 28).

EXAMPLE 11

Antibody Response to Injection of O12 and Vaccination Trial in Cattle

Twelve worm-naive calves were housed indoors and were allocated to 2 groups, C and E, each comprising 6 calves matched for age, breed and sex. All calves received a primary vaccination on day −63. Those in group E were vaccinated with 250 µg ConA Oo12; those in group C with 150 µg horse spleen ferritin (purchased from Sigma Chemical Co. Ltd., Poole, Dorset, UK) in order to act as negative (adjuvant) controls. Primary immunisation was with aluminium hydroxide and Freund's Complete adjuvant (FCA). Twenty one days later (day −42) all calves received a secondary vaccination, with a tertiary vaccination being administered after a further 21 days (both of 200 µg ConA Oo12 or 150 µg ferritin), both using Freund's incomplete adjuvant (FIA).

On day 0 all calves received an exogenous challenge of ca 40,000 L3 larvae of *O. ostertagi*. The levels of nematode infection were monitored by faecal egg counts, and determination of worm burden at necropsy twenty seven to twenty eight days post challenge.

Results

The mean worm burden of calves vaccinated with O12 was reduced relative to control animals vaccinated with horse spleen ferritin.

EXAMPLE 12

Inhibition of O12 Microsomal Aminopeptides Activity by Bovine Serum Containing Antibodies to ConA Oo12

An enyzme assay was carried out using the ELISA plate method (Example 7) to determine the effect of i) pre-immune, ii) anti-ferritin (control) and iii) bovine anti-ConA Oo12 (immune) sera on the microsomal aminopeptidase activity of ConA Oo12 in vitro. The pre-immune serum (i) was the pooled serum taken from the experimental group of calves (Group E, Example 7) 70 days pre-infection, the anti-ferritin serum (ii) was the pooled serum taken from the control group of calves (Group C, Example 7) and the bovine anti-ConA Oo12 serum (iii) was the pooled serum taken from the experimental group of calves (Group E, Example 7) at 27/28 days post infection.

10 µl ConA Oo12 (337 µg/ml) and 70 µl 50 mM MOPS buffer, pH 7.0 was added per well of a microtitre plate. 20 µl serum was added per well to bring the total volume per well to 100 µl. Control incubations included a buffer blank (MOPS buffer only) and ConA Oo12 without the addition of serum. The plate was preincubated for 30 minutes at 37° C. then 100 µl/well 2 mM methionine p-nitroanilide or leucine p-nitroanilide in MOPS buffer were added. The OD was read on an Elisa plate reader at 405 nm and the plate incubated for a further 30 min at 37° C. The OD was read again and the change in absorbance and percentage reduction in microsomal aminopeptidase activity calculated.

Results

| Sample | % Reduction in ApM Activity |
|---|---|
| Methionine-pNA as substrate | |
| ConAOo12 + 20 µl preimmune serum (group E) | 8.0 |
| ConAOo12 + 20 µl control serum (group C) | 21.4 |
| ConAOo12 + 20 µl immune serum (group E) | 41.7 |
| Leucine-pNA as substrate | |
| ConAOo12 + 20 µl preimmune serum (group E) | 17.1 |
| ConAOo12 + 20 µl control serum (group C) | 18.3 |
| ConAOo12 + 20 µl immune serum (group E) | 40.2 |

The serum from calves vaccinated with ConA Oo12 inhibited the aminopeptidase activity of O12 significantly compared to serum from the calves prior to vaccination (Pre-immune serum), on serum from control calves injected with horse spleen ferritin.

What is claimed is:

1. An isolated and purified antigen conferring protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia and being derived from and capable of conferring protective immunity against a non-obligate blood feeding helminth, wherein said antigen is obtainable from Ostertagia and has an apparent molecular weight (Mr) of about 124,000 to 126,000, as determined by SDS-PAGE on a 6–16% gel under denaturing conditions.

2. An isolated and purified antigen conferring protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia and being derived from and capable of conferring protective immunity against a non-obligate blood feeding helminth, wherein the amino acid sequence of the antigen contains the sequence: A E D L R L P T N I R P L I Y D L T (SEQ. ID. NO. 1).

3. An antigen as defined in claim 2, wherein the antigen has a sequence as defined in any one of SEQ ID Nos. 24, 25, 26, 27 or 28.

4. A method of preparing an antigen as claimed in claim 1 or 2, comprising the step of subjecting a crude extract of a non-obligate blood feeding helminth parasite of the genus Ostertagia or Cooperia to extraction with a detergent.

5. A method of preparing an antigen as claimed in claim 4, comprising the steps of subjecting a crude extract of a non-obligate blood feeding helminth parasite of the genus Ostertagia or Cooperia to extraction with a first detergent to remove membrane-associated proteins followed by solubilization with a second detergent to recover integral membrane proteins.

6. A method of preparing an antigen as claimed in claim 1 or 2, said process comprising preparing an extract of said parasite containing at least one protective antigen as defined in claim 1 or 2, purifying said antigen therefrom by binding said antigen to an immobilized phase including a specific binding partner for the antigen and subsequently eluting said antigen from said immobilized phase.

7. A vaccine composition for stimulating an immune response against helminth parasites in a non-human animal comprising one or more antigens as claimed in claim 1 or 2 together with a pharmaceutically acceptable carrier or diluent.

8. A method of stimulating an immune response against helminth parasites in a non-human animal, comprising administering to said animal a vaccine composition as claimed in claim 7.

9. An isolated and purified antigen conferring protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia, wherein the amino acid sequence of the antigen contains the sequence: A E D L R L P T N I R P L I Y D L T (SEQ. ID. NO. 1).

10. A method of preparing an antigen as claimed in claim 9 comprising the step of subjecting a crude extract of a non-obligate blood feeding helminth parasite of the genus Ostertagia or Cooperia to extraction with a detergent.

11. A method of preparing an antigen as claimed in claim 10, comprising the steps of subjecting a crude extract of the non-obligate blood feeding helminth parasite to extraction with a first detergent to remove membrane-associated proteins followed by solubilization with a second detergent to recover integral membrane proteins.

12. A method of preparing an antigen as claimed in claim 9, comprising preparing an extract of said parasite containing at least one said protective antigen, purifying said antigen therefrom by binding said antigen to an immobilized phase including a specific binding partner for the antigen and subsequently eluting said antigen from said immobilized phase.

13. A method as defined in claim 5 or 11 wherein the first detergent is Tween 20 and the second detergent is Thesit.

14. A method of preparing an antigen as claimed in any one of claims 4, 5, 10 or 11, wherein the method additionally comprises at least one chromatographic purification step.

15. An antigen prepared by any one of the methods defined in claim 4, 5, 14, 10, 11, or 12.

16. A synthetic polypeptide or fragment thereof expressed by a host cell or organism transformed with or containing a nucleic acid molecule comprising a nucleotide sequence encoding an antigen conferring protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia and being derived from and capable of conferring protective immunity against a non-obligate blood feeding helminth, wherein said nucleic acid molecule comprises a nucleotide sequence as set forth in any one of SEQ. ID. NOs. 19, 20, 21, 22 or 23, or a sequence which hybridizes with said sequence under conditions of high stringency, binding at 6× SSC/50% formamide and washing at 2× SSC, 65° C., wherein SSC is 0.15M NaCl, 0.15M sodium citrate, pH 7.2, and those sequence which would hybridize but for the degeneracy of the genetic code.

17. A method of preparing an antigen as claimed in claim 16 or 3, wherein said method comprises chemical synthesis.

18. A method of preparing a truncated form of a parasite antigen, said method comprising releasing the truncated form of the antigen from membranes by treatment with a proteolytic enzyme, wherein said antigen confers protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia and being derived from and capable of conferring protective immunity against a non-obligate blood feeding helminth.

19. A method of preparing a truncated form of a parasite antigen, said method comprising releasing the truncated form of the antigen from membranes by treatment with a proteolytic enzyme, wherein said antigen confers protective immunity against a non-obligate blood feeding helminth and which is characterized by possessing aminopeptidase M-like activity which can be assayed using an alanine, leucine or methionine p-nitroanilide substrate or aminopeptidase A-like activity which can be assayed using an α-glutamic acid nitroanilide substrate and which, in native form, is an integral membrane protein associated with the gut microvilli of a non-obligate blood feeding helminth parasite of the genus Ostertagia or Cooperia.

* * * * *